US009233825B2

(12) United States Patent
Madigan

(10) Patent No.: US 9,233,825 B2
(45) Date of Patent: Jan. 12, 2016

(54) HEATABLE PERSONAL LUBRICANT DISPENSOR

(71) Applicant: Stephen J. Madigan, Flower Mound, TX (US)

(72) Inventor: Stephen J. Madigan, Flower Mound, TX (US)

(73) Assignee: Stephen J. Madigan, Flower Mound, TX (US)

( * ) Notice: Subject to any disclaimer, the term of this patent is extended or adjusted under 35 U.S.C. 154(b) by 535 days.

(21) Appl. No.: 13/759,005

(22) Filed: Feb. 4, 2013

(65) Prior Publication Data

US 2013/0146614 A1    Jun. 13, 2013

Related U.S. Application Data

(60) Continuation-in-part of application No. 13/289,890, filed on Nov. 4, 2011, now Pat. No. 8,365,738, which is a division of application No. 12/447,255, filed as application No. PCT/US2007/081946 on Oct. 19, 2007, now Pat. No. 8,074,653.

(60) Provisional application No. 60/930,558, filed on May 17, 2007, provisional application No. 60/854,281, filed on Oct. 25, 2006.

(51) Int. Cl.
*B67D 3/00* (2006.01)
*A61F 6/00* (2006.01)
(Continued)

(52) U.S. Cl.
CPC .............. *B67D 3/0022* (2013.01); *A61F 6/005* (2013.01); *B05B 11/304* (2013.01); *B05B 11/3032* (2013.01); *B05C 5/001* (2013.01);
(Continued)

(58) Field of Classification Search
CPC ........ B65D 23/06; B65D 47/40; B65D 49/10; B65D 49/08; B65D 47/38; B65D 5/746; B65D 5/747; B65D 83/265; A61F 6/005; B05B 11/304; B05B 11/3032; B67D 3/0022; B05C 11/042; B05C 5/001; B05C 11/1042
See application file for complete search history.

(56) References Cited

U.S. PATENT DOCUMENTS 5,117,841 A    6/1992    McBeth
5,163,448 A    11/1992   Foldesy
(Continued)

FOREIGN PATENT DOCUMENTS

WO    95/02379 A1    1/1995

OTHER PUBLICATIONS

European Search Report EP 07872327.7 dated Feb. 2, 2010.
(Continued)

*Primary Examiner* — Frederick C Nicolas
(74) *Attorney, Agent, or Firm* — Daniel J. Chalker; Chalker Flores, LLP

(57) ABSTRACT

A personal lubricant dispenser includes an enclosure, a pre-delivery chamber, one or more heating elements proximate to the pre-delivery chamber, an electrical connector disposed on an exterior of the enclosure and electrically connected to the heating elements, an inlet cavity disposed above the pre-delivery chamber, a piercing element attached to the inlet cavity, a inlet valve (normally closed) connecting the inlet cavity to the pre-delivery chamber, a inlet actuator disposed on the exterior of the enclosure and operably connected to the inlet valve to open the inlet valve, an outlet cavity disposed below the pre-delivery chamber, an outlet valve (normally closed) connecting the outlet cavity to the pre-delivery chamber, an outlet actuator disposed on the exterior of the enclosure and operably connected to the outlet valve to open the outlet valve, and a spout disposed on or within the exterior of the enclosure and connected to the outlet cavity.

60 Claims, 28 Drawing Sheets

(51) Int. Cl.
  *B05C 5/00* (2006.01)
  *B05C 11/10* (2006.01)
  *B05B 11/00* (2006.01)
  *B65D 47/38* (2006.01)
  *B65D 83/26* (2006.01)

(52) U.S. Cl.
  CPC ............ *B05C 11/1042* (2013.01); *B65D 47/38* (2013.01); *B65D 83/265* (2013.01)

(56) References Cited

U.S. PATENT DOCUMENTS

| | | | |
|---|---|---|---|
| 5,190,191 A * | 3/1993 | Reyman | B05B 9/0838 222/256 |
| 5,730,327 A * | 3/1998 | Stern | A47K 5/1209 222/105 |
| 6,036,022 A | 3/2000 | Young | |
| 6,176,394 B1 | 1/2001 | Shimko et al. | |
| 6,213,424 B1 | 4/2001 | Helfer-Grand | |
| 6,311,868 B1 | 11/2001 | Krietemeier et al. | |
| 6,484,514 B1 | 11/2002 | Joseph et al. | |
| 6,581,775 B1 | 6/2003 | Hagopian | |
| 6,612,427 B2 | 9/2003 | Woodhouse | |
| 6,694,980 B2 | 2/2004 | Anderson | |
| 6,742,521 B2 | 6/2004 | McCleskey et al. | |
| 6,911,010 B2 | 6/2005 | Dirks et al. | |
| 7,021,064 B2 | 4/2006 | Wohland et al. | |
| 8,074,653 B2 | 12/2011 | Madigan et al. | |
| 8,220,666 B2 * | 7/2012 | Abe | A47K 5/1204 222/181.2 |
| 8,365,738 B2 | 2/2013 | Madigan et al. | |
| 2005/0045497 A1 | 3/2005 | Sample | |

OTHER PUBLICATIONS

International Search Report and Written Opinion for PCT/US2007/81946 dated Jun. 18, 2008.

* cited by examiner

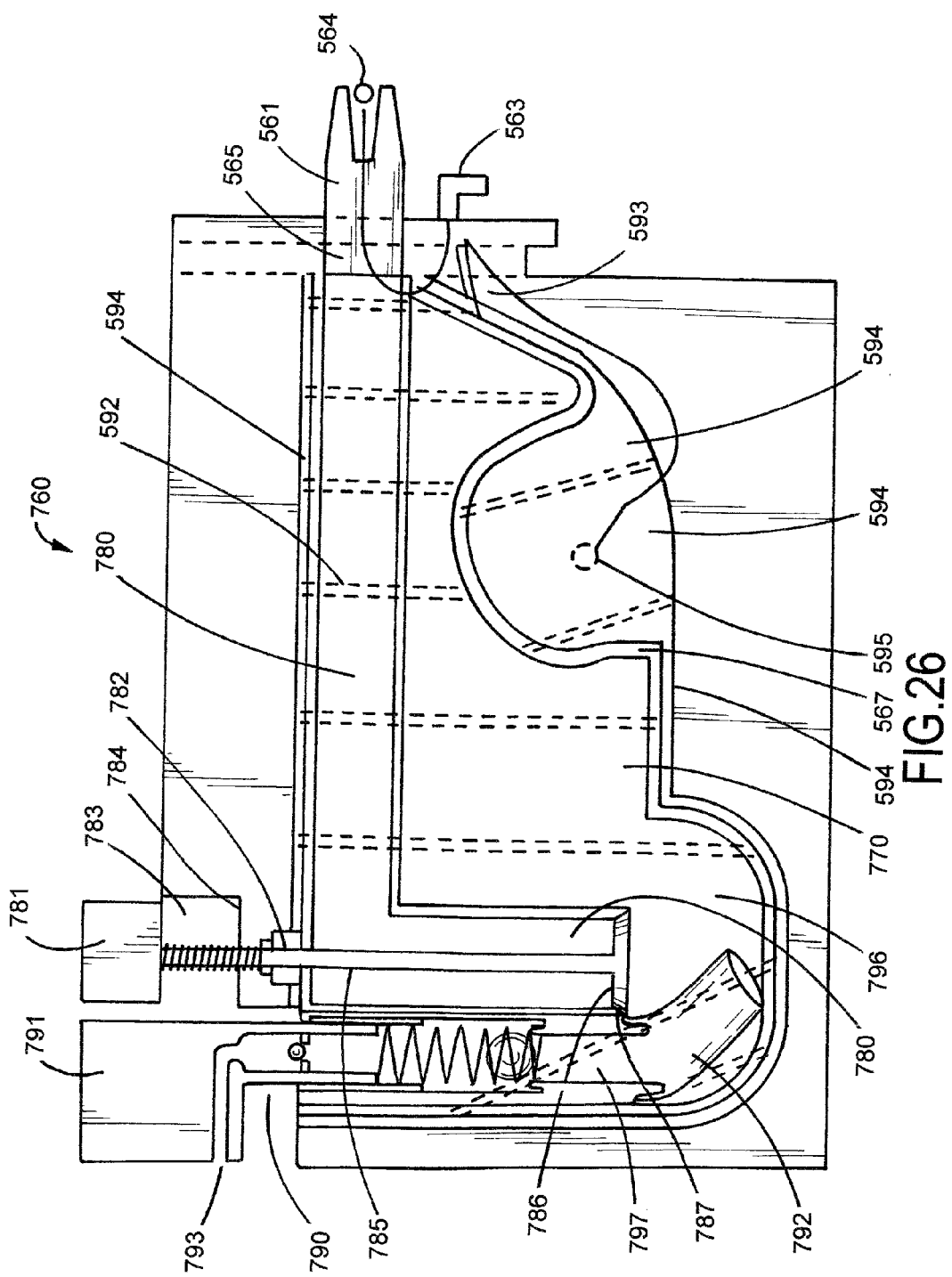

HEATABLE PERSONAL LUBRICANT DISPENSOR

PRIORITY CLAIM

This patent application is a continuation-in-part application of U.S. patent application Ser. No. 13/289,890 filed on Nov. 4, 2011, now U.S. Pat. No. 8,365,738, and entitled "Combination Condom and Personal Lubricant Container," which is a divisional patent application of U.S. patent application Ser. No. 12/447,255 filed on Apr. 25, 2009, now U.S. Pat. No. 8,074,653, and entitled "Combination Condom and Personal Lubricant Container," which is a Section 371 U.S. national phase application of PCT/US07/81946 filed on Oct. 19, 2007, which claims priority to U.S. provisional patent application Ser. Nos. 60/930,558 filed on May 17, 2007 and 60/854,281 filed on Oct. 25, 2006, all of which are hereby incorporated by reference in their entirety.

The patent application is related to U.S. patent application Ser. No. 12/989,647, filed on Apr. 8, 2011 and entitled "Device for Heating Products Used in Sexual Activities," which is hereby incorporated by reference in its entirety.

FIELD OF THE INVENTION

This invention relates to a dispenser and more specifically to a device for heating and dispensing a personal lubricant used in sexual activities.

BACKGROUND OF THE INVENTION

Containers or kits have been configured to house a condom and/or liquid material used prior to, in, or after sexual activities. A device has been developed to house a condom and liquid material said device comprising a means to dispense the liquid material. Devices have been developed comprised of an element that heats liquid material contained therein prior to extraction using an exothermic or electric heat source. A device has been developed comprised of an element that heats a liquid material contained therein but only after the liquid material is dispensed on a target area. A device has been developed to house articles to be dispensed but only after a liquid material contained within the device is applied to an article and heated prior to dispensing the moistened, heated article. The prior art hereinafter discussed is limited to articles of manufacture that house one or more condoms, a liquid material used in sexual activities or a condom and a liquid material used in sexual activities and devices that heat a liquid material contained therein either prior to or after removal of the liquid material or heat a pre-moistened article contained within the device prior to removal of the article from the device.

U.S. Pat. No. 6,742,521 B2 issued in June of 2004 to McCleskey et al., entitled "Combination Prophylactic and Sanitizer," principally describes an invention combining a packaged prophylactic with a packaged sanitizer. The McCleskey invention claims a combination prophylactic and sanitizer comprising at least one disposable package containing at least one prophylactic and at least one disposable package containing at least one sanitizer said packages may be removably secured to each other. An alternative embodiment of the McCleskey invention claims a separate package used as a receptacle into which used/contaminated prophylactics or sanitizers are placed.

The McCleskey invention combines at least one disposable package containing at least one prophylactic and at least one disposable package containing at least one sanitizer. The term "sanitizer" is defined in the McCleskey specification. A sanitizer is a disposable towelette, napkin, wipe, and/or swab pre-moistened with a sterilizing agent, lubricant, or spermicidal. The specification further provides that although a sanitizer is preferably a pre-moistened towelette, it is contemplated in an alternate embodiment that a sanitizer may be a self-contained liquid/gel sterilizing agent (without towelette). However, the specification does not provide that a sanitizer may be a self-contained liquid used in sexual activities (without towelette) other than a self-contained liquid/gel antiseptic or sterilizing agent.

Moreover, the McCleskey specification provides that a prophylactic or sanitizer within a package is manually removed after tearing open the package. The McCleskey invention discloses a means to manually reseal a package that contains or contained at least one sanitizer or a receptacle designed to hold used/contaminated prophylactics or sanitizers/towelettes. The McCleskey invention does not provide a means to reseal a package containing at least one prophylactic. The package containing a prophylactic or sanitizer may be formed from any suitable packaging material including aluminum, plastic, or paper. The package comprises multiple two-sided packages—only two walls.

The McCleskey invention comprises a package containing at least one prophylactic. The specification makes no mention of a liquid material enclosed within the package other than that contained in a conventional package.

U.S. Pat. No. 6,581,775 B1 issued in June of 2003 to Hagopian, entitled "Method of External Genital Cleansing and Prophylactic Kit," describes a kit comprised of a sealed container housing one or more packaged condoms and one or more packaged wipes having topical microbicides, personal lubricants, sterile water, or sterile water-based solution disposed on or impregnated therein. The articles comprising the kit are principally used to avoid the transmission of disease during sexual intercourse, to provide a lubricating aid during sexual intercourse, and to externally cleanse the genitals prior to or after sexual intercourse. The articles comprising the kit are available over the counter.

U.S. Pat. No. 6,652,427 B2 issued in September of 2003 to Woodhouse, entitled "Method and Apparatus for Containing Prophylactic Articles," describes a sanitary non-disposable container for storing one or more prophylactics. The container is comprised of a convex compartment, a recessed compartment, and a hinge that permits the compartment to mate forming an airtight seal. An unpackaged prophylactic is situated between the two compartments when the container is in a closed position. Although not claimed, the specification provides that a sanitary compartment may be added that houses a personal lubricant.

U.S. Pat. No. 6,694,980 B2 issued in February of 2004 to Anderson, entitled "Prophylactic Garment System for Safer Sex," describes an undergarment worn while performing sexual activities comprising an opening in the crouch area facilitating intercourse and one or more pockets used to store sexual aids, including a packaged condom or packaged personal lubricant. The sexual aids are intended to be individually purchased over the counter.

U.S. Pat. No. 6,036,022 issued in March of 2000 to Young, entitled "Combination Condom Case and Fragrance Dispenser," describes a combination condom case and fragrance dispenser. The Young invention comprises a portable non-disposable container comprising a compartment that contains a condom or condoms and a compartment that contains a fragrance or perfume tube. The fragrance or perfume contained in the tube is dispensed through an opening in the front wall by means of depressing a plunger located on the top wall.

The condom or condoms housed in the device are individually purchased over the counter.

U.S. Pat. No. 5,163,448 issued in November of 1992 to Foldesy, entitled "Condom Comprising Dispensing Structure and Method of Making and Using the Same," describes a condom comprising openings on its proximal portion said condom rolled onto a roll ring containing a liquid material and as the roll ring is squeezed the liquid material exudes out through the openings of the condom.

U.S. Pat. No. 6,484,514 B1 issued in November of 2002 to Joseph et al., entitled "Product Dispenser Having Internal Temperature Changing Element," describes a temperature modifying system for heating a product within a flexible container using an exothermic element also contained within the flexible holder. The heat from the exothermic element is released when pressure is applied to the outside of the flexible container causing the internal element to rupture. The product dispensed is heated as a result.

U.S. Patent App. No. 2004/0194472 A1 published in October 2004 by Wohland et al., entitled "Multi-Compartment Pack for Cooling or Heating of Products," describes a multi-compartment pack comprising a product contained within a compartment that is exothermically heated before being removed and two other compartments containing the components that create the chemical reaction resulting in exothermic heat.

U.S. Pat. No. 6,311,868 B1 issued in November of 2001 to Krietemeier et al., entitled "Dispenser Which Incrementally Heats Fluids with Substantial Non-Volatile Constituent Parts," describes a device that houses a large quantity of liquid material then transfers a portion of the liquid material to a pre-delivery chamber where it is heated to a desired temperature finally dispensing the liquid material by means of a dispensing spout. The device is AC or DC powered.

U.S. Pat. No. 6,911,010 B2 issued in June of 2005 to Dirks et al., entitled "Heated Massager with Massaging Liquid Dispenser," describes a hand-held battery powered vibrating massager comprising a heated vibrating body contacting element, and a sealed container of massaging liquid. The dispensed massaging liquid is heated on the target surface by means of the body contacting element.

U.S. Pat. No. 6,213,424 B1 issued in April of 2001 to Helfer-Grand, entitled "Towelette Dispenser Apparatus," describes a portable device that dispenses pre-moistened heated towelettes. The towelettes may be housed originally in the dispenser dry and moistened as dispensed or originally housed in the dispenser in a pre-moistened state. In either case the towelette is heated as dispensed. The portable dispenser if AC or DC powered.

U.S. Pat. No. 8,061,918 B2 issued in November of 2011 to Skalitzky et al., entitled "Heated Flowable Dispenser," describes a portable bottle comprising heat generating means used to heat a portion of personal lubricant contained therein. The bottle comprises a pumping mechanism used to drive the portion of the product to be heated into a heating chamber comprising the bottle. The bottle may be activated when positioned within a docking station which is comprised of the remaining electrical circuitry, including a PCB, and contains or is in communication with a power source.

U.S. Patent Application Publication No. 20120003025 A1 published on Jan. 5, 2012 and filed by Skalitzky et al., titled "Heating Personal lubricantDispenser," describes a portable bottle comprising heat generating means used to heat a portion of personal lubricant contained therein. With the aid of a pumping system, the portion of the product to be heated is urged into a heating chamber comprising the bottle by squeezing the bottle or otherwise tormenting the bottle.

U.S. Pat. No. 6,454,127 B1 issued in September of 2002 to Suomela et. al., entitled "Self-Contained Liquid Dispenser with Heating Means," describes a portable liquid heating and dispensing system comprising a container housing a main reservoir of liquid a portion of which is heated prior to extraction and a docking station within which the container is positioned providing the electrical power to heat the liquid. A pump assembly is used to lift liquid out of the main reservoir into a chamber of the pump comprising heat generating means and eventually through a spout.

U.S. Patent Application Publication No. 20120125950 A1 published on May 24, 2012 and filed by Bouix et. al., entitled "Reusable Pump Dispenser for Heated Personal Care Compositions," describes a portable hand-held device housing a main reservoir of personal lubricants portion of which is heated prior to extraction. A pump assembly is used to lift the product out of the main reservoir into a chamber of the pump comprising heat generating means and eventually through a spout.

U.S. Pat. No. 7,909,044 B2 issued in March of 2011 to Franchant et. al., entitled "Applicator Device for Applying a Cosmetic and the Use of such a Device," describes a hand-held battery operated cosmetic applicator having an internal cavity comprising an inlet into which a stick of mascara is manually loaded, a chamber comprising heat generating means in which said mascara is heated and softened and outlets through which said mascara is excreted onto the applicator bristles. The stick of mascara is heated and dispensed in its entirety.

Similarly, U.S. Pat. No. 8,142,090 B2 issued in March of 2012 to Kamada et. al., entitled "Cosmetic Product and Method of Applying Mascara Composition," describes a hand-held battery operated cosmetic applicator having an internal cavity comprising an inlet into which a stick of mascara is loaded by a mechanical carrier of mascara sticks, a chamber comprising heat generating means in which said mascara is heated and softened and outlets through which said mascara is excreted onto the applicator bristles. The stick of mascara is heated and dispensed in its entirety.

U.S. Pat. No. 7,975,879 B2 issued in July of 2011 to Grossbeck et. al., entitled "Temperature Controlled Liquid Dispenser Containers therefore, and Bag-in-Box Container Construction," describes an article of manufacture that cools and heats water for human consumption. In one embodiment water cooled within the apparatus is dispensed through the main spout or diverted to an auxiliary heating unit through tubing running from the main spout to the heating unit where it is heated and dispensed through a second spout.

U.S. Pat. No. 8,056,764 B2 issued November of 2011 to Paasch et. al, entitled Metered Volume Liquid Dispensing Device," describes a liquid food product dispenser assembly with heat generating means. The dispenser assembly includes a dispenser comprising the means to dispense the personal lubricant from a reservoir within which the personal lubricants heated and a base comprising the heat generating means within which the dispenser is positioned when the product is being heated.

SUMMARY OF THE INVENTION

The present invention encourages the use of condoms in sexual activities thereby reducing the spread of disease, including the human immunodeficiency virus (HIV), which may result in AIDS, and reducing the risk of pregnancy. In one embodiment, the present invention discloses a disposable container comprising a condom compartment enclosing one or more condoms immersed in a liquid material such as personal lubricant, removably adjoined to at least one personal lubricant compartment enclosing a liquid material such as personal lubricant, and a kit comprising at least one condom compartment and at least one associated personal lubricant compartment. Prior to their removal, the contents of the condom compartment are heated by a device in which the compartment is seated. A condom substantially more lubricated than a typical packaged condom is easier to don. Also, the donning of a warm condom that has been a heated by a liquid material in which it is immersed is more sensually pleasing than donning a typical packaged condom. The portion of personal lubricant contained in the opened compartment, now warm, may be applied to the penis further facilitating the donning of the condom. The condom is preferably a male condom. Personal lubricants include a lubricant sold under the brand name KY, Durex, Astroglide, Liquid Silk, among others, and is not limited to water-based lubricants.

In another embodiment, the present invention packages a condom and a liquid material such as personal lubricant in a single compartment or container comprising multiple compartments. By packaging a condom with a popular sexual aid, such as personal lubricant, use of condoms will be encouraged as both are immediately available.

The present invention also provides post-menopausal women who use personal lubricants in their sexual activities with an option. Currently, these women use lubricants that are either applied to the skin at ambient temperature or a chemically induced temperature approaching body temperature. The application of these lubricants at these temperatures may negatively affect the sexual experience. Personal lubricant heated to a temperature equaling or exceeding body temperature results in greater pore penetration and, therefore, less friction and irritation when participating in sexual activities. Chemical burn associated with certain warming lubricants is avoided.

In addition, the present invention provides an article of manufacture containing items used in sexual activities that is tamper-proof and meets the highest of standards for personal hygiene. As regards tampering, the compartments are hermetically sealed. The condom compartment comprises a seal located on the top wall. When the seal is opened, the contents of the condom compartment are exposed and manually accessible. The personal lubricant compartment comprises a discharge element comprising multiple seals. The contents within the personal lubricant compartment are accessed and mechanically discharged after rupturing a protective seal within the discharge element presumably with the piercing element of a removable dispenser. Preferably, a cap covering the discharge element is removed prior to rupturing the protective seal. Alternatively, the contents of the compartment are removed with the aid of a permanently attached dispenser. As regards personal hygiene, safeguards have been included which reduce the risk that liquid material contained in any previously accessed compartment will not migrate out. The condom compartment has two built-in safeguards. First, an opened condom compartment may be resealed by reattaching or closing the seal to the top wall. Second, a raised annular ring positioned on the top wall of the condom compartment provides a barrier to the migration of liquid material out of the compartment and into the heating mechanism of a warming device in which the compartment is seated. The personal lubricant compartment has built-in safeguards. First, a cap may be re-installed to the end of the discharge element. Second, the discharge element is sized to accommodate a removable dispenser that fits snugly within the element avoiding leakage. Finally, compartments comprising a container may be detached from one another. A previously accessed compartment may be detached avoiding a mess not otherwise solved.

The present invention allows a liquid material, such as personal lubricant, to be heated to a temperature that equals or exceeds body temperature. Warm personal lubricant applied to the skin results in greater pore penetration than a personal lubricant applied to the skin at a temperature well below body temperature. The application of warm personal lubricant avoids the shock associated with a personal lubricant that has not been heated to a temperature that exceeds body temperature. The temperature of the liquid material enclosed within a compartment may be monitored with the aid of a temperature sensor known in the art when the container is seated in a warming device.

Using the present invention, a user is given a choice as to how much personal lubricant to heat given his or her expectations. All of the personal lubricant contained in either a personal lubricant compartment or container may be heated in its entirety while seated within a warming device. The user may activate an attached heatable single chamber or heatable dual chamber dispenser maintaining the temperature of personal lubricant heated within a compartment or container throughout the discharging process or heating only the portion of the personal lubricant fed into a heatable chamber of the dispenser from a compartment or container and discharging that portion.

In one embodiment, the personal lubricant migrates out of a compartment or container into the dispenser's inlet, from there into a heatable pre-delivery chamber of the dispenser and out through the dispenser's spout under the influence of gravity reducing complexity of the invention.

In order to reduce waste, a combination condom and personal lubricant container may having multiple compartments adjoined to one another. The compartments may be detached from one another with the aid of perforations in the container. If either compartment has been depleted, the depleted compartment may be removed and discarded without discarding the full or partially depleted compartment. Also, the user of the invention determines the amount of liquid material to be removed or dispensed from a compartment not possible with a single use package containing a limited amount of the liquid material.

The present invention also allows a user to avoid the mess associated with removing a liquid material from a disposable package by tearing an edge. Opening such a package is often difficult particularly if the quantity of liquid material within a first package was insufficient and a second package is being opened with lubricated hands. The contents of the personal lubricant compartment are dispensed using a dispenser.

In another embodiment, the present invention provides a heatable single chamber dispenser or heatable dual chamber dispenser attached to a personal lubricant compartment or container that is disposable. Continued use of a non-disposable dispenser presents hygiene issues that are solved only by periodically cleaning the dispenser.

The present invention relates to disposable container comprising a condom compartment enclosing one or more condoms and a personal lubricant in which said one or more condoms are immersed, removably adjoined to at least one personal lubricant compartment enclosing a personal lubricant, and a kit comprising at least one condom compartment and at least one associated personal lubricant compartment, wherein the personal lubricant compartment may comprise an attached heatable single chamber dispenser or heatable dual chamber dispenser. The invention also relates to a disposable personal lubricant container comprising an attached heatable single chamber dispenser or heatable dual chamber dispenser said container not associated with a condom compartment. In lieu of personal lubricant, the compartments or the personal lubricant container may enclose a sexually stimulating lubricant. The condom compartment is constructed of a packaging material containing properties that conduct heat such as aluminum, is three-dimensional in shape including but not limited to a cylindrical or rectangular shape, is hermetically sealed, and may be associated with or removably adjoined to a personal lubricant compartment. The personal lubricant compartment is constructed of a heatable packaging material containing properties that conduct heat, is three dimensional in shape including but not limited to a funnel shape, and is associated with or removably adjoined to a condom compartment. The personal lubricant container is constructed of packaging heatable materials containing properties that conduct heat and is three-dimensional in shape. The contents of the condom compartment are manually accessed by removing or opening a seal positioned atop the compartment. The seal may be re-attached or closed to avoid spillage or waste. The condom compartment may comprise a raised annular ring positioned on the top of the compartment providing an additional barrier to the migration of liquid material. The contents of the personal lubricant compartment are accessed by rupturing a protective seal within a discharge element comprising the compartment. The contents are then discharged through the discharge element by activating a removable dispenser that fits snugly within the discharge element. The contents of the compartments or personal lubricant container are preferable heated prior to being removed or discharged. The temperature of the contents may be monitored with the aid of a temperature sensing aid. When the condom compartment comprises a part of a container, it is positioned at the distal end (in relation to the point of discharge of the contents from the second compartment) of the container while the personal lubricant compartment is positioned at the proximal end of the container. The container comprises perforations the means used to detach the compartments. In lieu of a single personal lubricant compartment, a container may comprise two congruent compartments, each compartment adjoined to the condom compartment and positioned on opposing ends of the container.

More specifically, the present invention provides a personal lubricant dispenser that includes an enclosure, a pre-delivery chamber disposed within the enclosure, one or more heating elements disposed within the enclosure proximate to the pre-delivery chamber, an electrical connector disposed on an exterior of the enclosure and electrically connected to the one or more heating elements, an inlet cavity disposed within the enclosure above a portion of the pre-delivery chamber, a piercing element attached to the inlet cavity and accessible from the exterior of the enclosure, a inlet valve (normally closed) disposed within the enclosure and connecting the inlet cavity to the pre-delivery chamber, a inlet actuator disposed on the exterior of the enclosure and operably connected to the inlet valve to open the inlet valve, an outlet cavity disposed within the enclosure below a portion of the pre-delivery chamber, an outlet valve (normally closed) disposed within the enclosure and connecting the outlet cavity to the pre-delivery chamber, an outlet actuator disposed on the exterior of the enclosure and operably connected to the outlet valve to open the outlet valve, and a spout disposed on or within the exterior of the enclosure and connected to the outlet cavity.

In addition, the present invention provides a system that includes a dispenser and a control unit. The dispenser includes an enclosure, a connection interface disposed on the enclosure, a pre-delivery chamber disposed within the enclosure, one or more heating elements disposed within the enclosure proximate to the pre-delivery chamber, an electrical connector disposed on or within the connection interface and electrically connected to the one or more heating elements, an inlet cavity disposed within the enclosure above a portion of the pre-delivery chamber, a piercing element disposed on or within the connection interface and attached to the inlet cavity and accessible from the exterior of the enclosure, a inlet valve (normally closed) disposed within the enclosure and connecting the inlet cavity to the pre-delivery chamber, a inlet actuator disposed on the exterior of the enclosure and operably connected to the inlet valve to open the inlet valve, an outlet cavity disposed within the enclosure below a portion of the pre-delivery chamber, an outlet valve (normally closed) disposed within the enclosure and connecting the outlet cavity to the pre-delivery chamber, an outlet actuator disposed on the exterior of the enclosure and operably connected to the outlet valve to open the outlet valve, and a spout disposed on or within the exterior of the enclosure and connected to the outlet cavity. The control device is removeably connected to the connection interface of the dispenser. The control device includes a power source, an electrical circuit electrically connected to the power source and the electrical connector to control a temperature of a personal lubricant within at least the pre-delivery chamber of the dispenser, a personal lubricant container having a discharge element such that the piercing element of the dispenser is shaped to receive the discharge element and break a seal protecting the personal lubricant within the personal lubricant container and the personal lubricant flows through the piercing element into the inlet cavity of the dispenser. The control device can be a condom warming device, a personal lubricant warming device, or a combination condom and personal lubricant device.

BRIEF DESCRIPTION OF THE DRAWINGS

The above and further advantages of the invention may be better understood by referring to the following description in conjunction with the accompanying drawings, in which:

FIG. 26 shows a cross-sectional view of a heatable dual chamber pump dispenser;

DETAILED DESCRIPTION OF THE INVENTION

Figure 1:
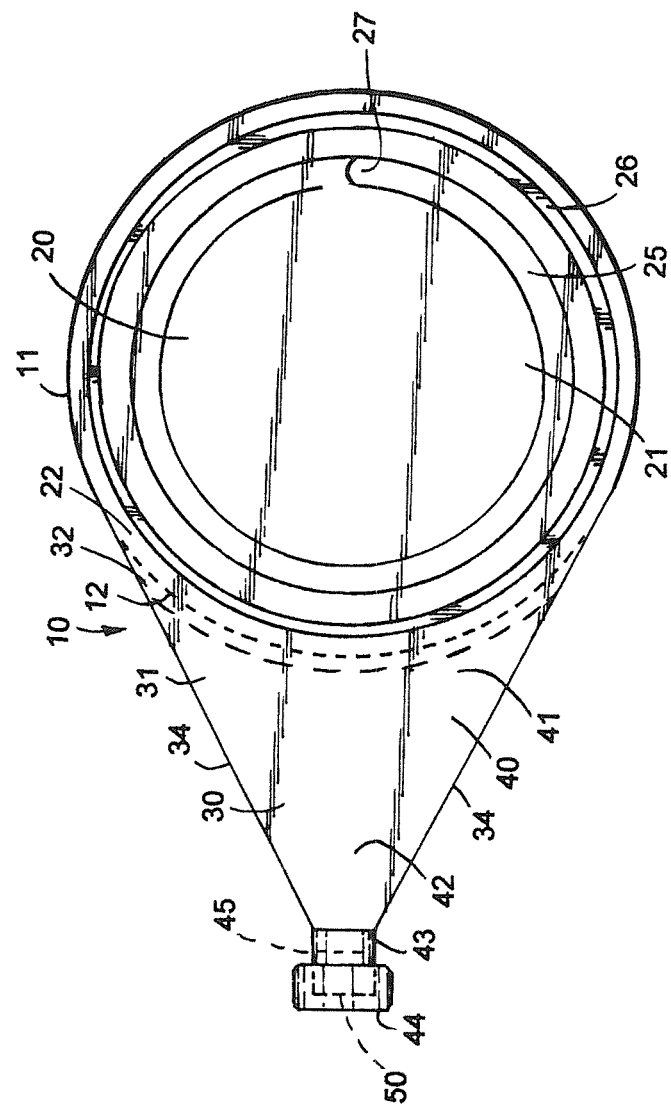
FIG. 1 shows the first of three top views of a first embodiment of a combination condom and personal lubricant container.

The present invention relates to disposable container comprising a condom compartment enclosing one or more condoms and a personal lubricant in which said one or more condoms are immersed, removably adjoined to at least one personal lubricant compartment enclosing a personal lubricant, and a kit comprising at least one condom compartment and at least one associated personal lubricant compartment, wherein the personal lubricant compartment may comprise an attached heatable single chamber dispenser or heatable dual chamber dispenser. The invention also relates to a disposable personal lubricant container comprising an attached heatable single chamber dispenser or heatable dual chamber dispenser said container not associated with a condom compartment. In lieu of personal lubricant, the compartments or the personal lubricant container may enclose a sexually stimulating lubricant. The condom compartment is constructed of a packaging material containing properties that conduct heat such as aluminum, is three-dimensional in shape including but not limited to a cylindrical or rectangular shape, is hermetically sealed, and may be associated with or removably adjoined to a personal lubricant compartment. The personal lubricant compartment is constructed of a heatable packaging material containing properties that conduct heat, is three dimensional in shape including but not limited to a funnel shape, and is associated with or removably adjoined to a condom compartment. The personal lubricant container is constructed of packaging heatable materials containing properties that conduct heat and is three-dimensional in shape. The contents of the condom compartment are manually accessed by removing or opening a seal positioned atop the compartment. The seal may be re-attached or closed to avoid spillage or waste. The condom compartment may comprise a raised annular ring positioned on the top of the compartment providing an additional barrier to the migration of liquid material. The contents of the personal lubricant compartment are accessed by rupturing a protective seal within a discharge element comprising the compartment. The contents are then discharged through the discharge element by activating a removable dispenser that fits snugly within the discharge element. The contents of the compartments or personal lubricant container are preferable heated prior to being removed or discharged. The temperature of the contents may be monitored with the aid of a temperature sensing aid. When the condom compartment comprises a part of a container, it is positioned at the distal end (in relation to the point of discharge of the contents from the second compartment) of the container while the personal lubricant compartment is positioned at the proximal end of the container. The container comprises perforations the means used to detach the compartments. In lieu of a single personal lubricant compartment, a container may comprise two congruent compartments, each compartment adjoined to the condom compartment and positioned on opposing ends of the container.

First Embodiment of Combination Condom and Personal Lubricant Container—FIGS. 1, 2, 3, 4, 5, 6.

FIGS. 1-6 show various views of a first embodiment of article of manufacture comprising a condom compartment 20 removably adjoined to a personal lubricant compartment 30 hereinafter referred to as a combination condom and personal lubricant container 10. The container 10 is disposable. The compartments 20, 30 comprising the container 10 are constructed of a flexible, semi-rigid, or rigid packaging material 11 comprising properties that conduct heat, such as aluminum. The compartments are adjoined to one another at a protruding curved edge of the top wall of each compartment 22, 32 forming a common border. The compartments 20, 30 may be permanently separated from one another with the aid of perforations in the top of the container 12 arranged in a curved pattern along the common border.

Figure 2:
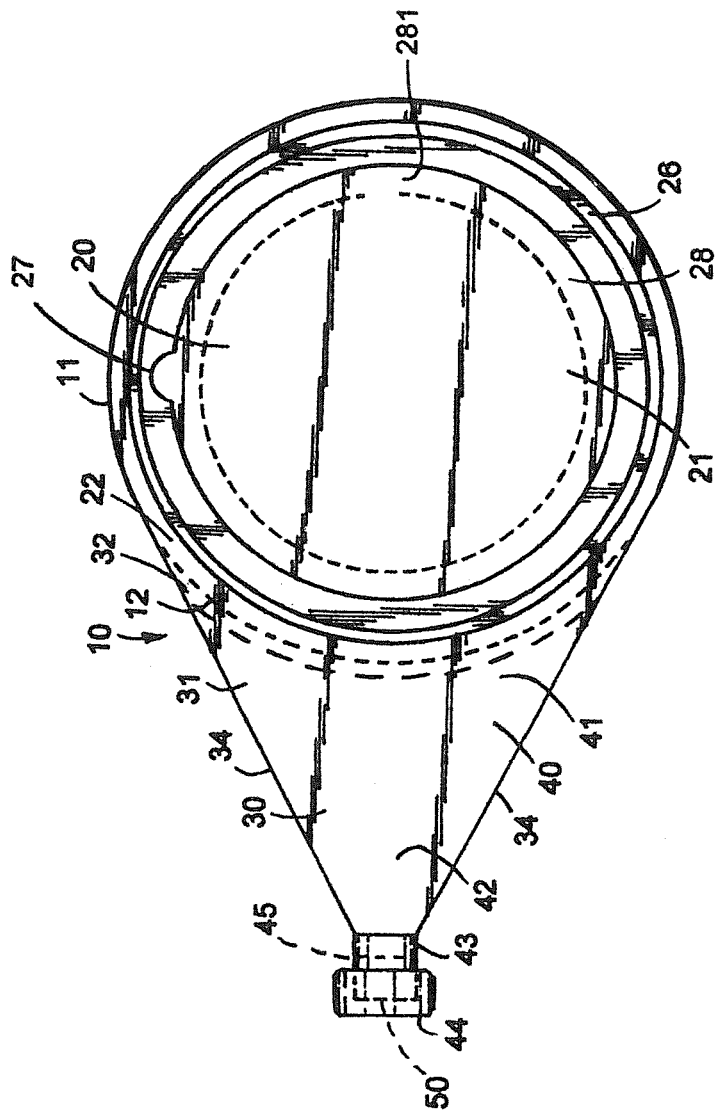
FIG. 2 shows the second of three top views of a first embodiment of a condom and personal lubricant container.
Figure 3:
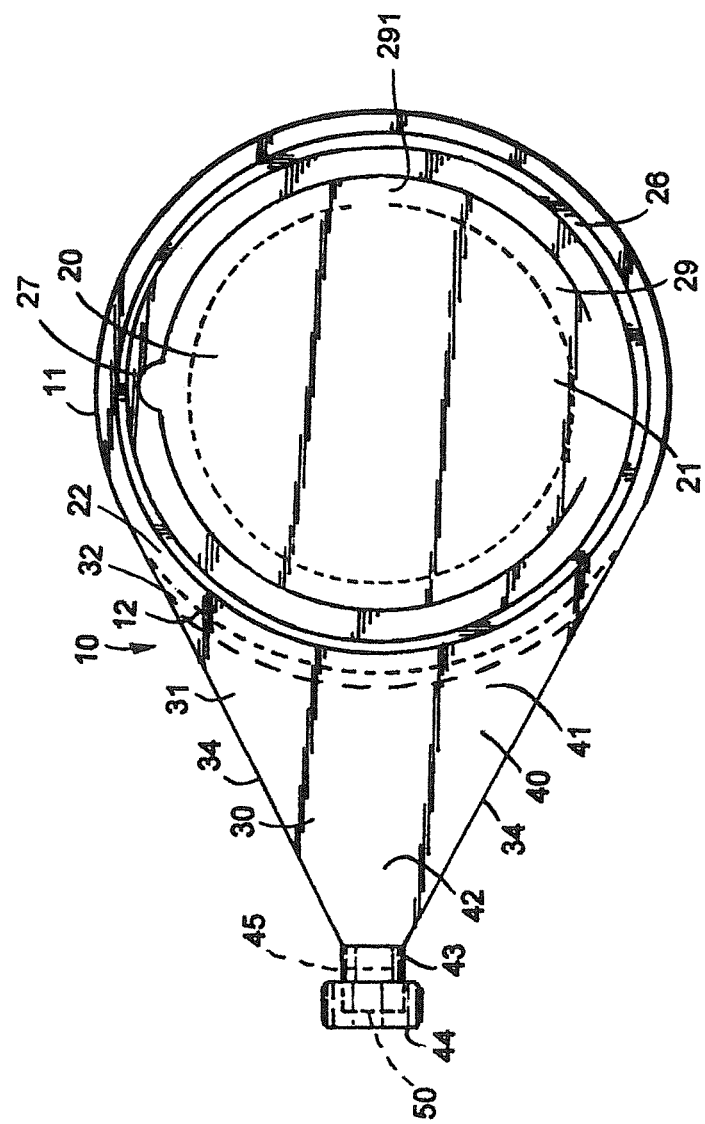
FIG. 3 shows the third of three top views of a first embodiment of a condom and personal lubricant container.

FIGS. 1, 2 and 3 discussed below each show a top view of the first embodiment of the combination condom and personal lubricant container 10. In each drawing the top wall of the condom compartment 21 is shown to comprise a different seal, in design and function. Descriptions of the first embodiment of the combination condom and personal lubricant container 10 shown in FIGS. 2 and 3 are limited to descriptions of the particular seal 28, 29.

FIG. 1 shows the first of three top views of the first embodiment of the combination condom and personal lubricant container 10. The condom compartment 20 is positioned at the distal end (in relation to the point of discharge 50 of the contents in the personal lubricant compartment 30) of the container 10. The top view shows the top wall of the condom compartment 21 to be oval shaped. The top wall 21 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. The top wall of the condom compartment 21 also comprises a protruding curved edge 22 extending out the entire perimeter of the top wall 21. Preferably, the top wall of the condom compartment 21 also comprises a raised annular ring 26. The raised annular ring 26 is positioned between the perimeter of the top wall of the compartment 21 and the removable seal 25. The raised annular ring 26 provides a barrier to the migration of liquid material contained in an open condom compartment 20 when the container 10 is seated in a device used to heat its contents. The raised annular ring 26 helps prevent liquid material from entering the part of a device that heats the contents of the compartments 20, 30.

The personal lubricant compartment 30 is positioned at the proximal end of the container 10. The personal lubricant compartment 30 is in the shape of a funnel 40. The top wall 31 of the personal lubricant compartment 30 comprises a protruding curved edge 32 extending away from a curved interior side wall 35 (shown by a dashed line). The protruding curved edge 32, two side walls 34 (top edge only shown) separated by a discharge element 43 and the discharge element 43 mark the perimeter of the top of the compartment 30. The top wall 31 of the compartment 30 is tapered sloping downward away from the curved interior side wall 35, the broad end of the funnel 41, and terminating at the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 30. Personal lubricant discharged is, for the most part, gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably with a piercing element of a removable dispenser. The discharge element 43 may also comprise a cap 44 that must be removed from the end of the element 43 before rupturing the protective seal 45.

FIG. 2 shows the second of three top views of the first embodiment of the combination condom and personal lubricant container 10. The discussion set forth in this paragraph is limited to the design of the seal. The top wall of the condom compartment 21 comprises a removable re-attachable seal 28 comprising a tab 27 and a circular support for a re-attachable seal 281, in lieu of a removable seal 25 that is not re-attachable. The drawing depicts an oval-shaped seal 28. By pulling the tab 27 and removing the seal 28, the contents of the compartment 20 are accessed and may be manually removed. The seal 28 may be re-attached to the top wall of the compartment 21 by pressing the seal against the circular support for a re-attachable seal 281. By re-attaching the seal 28, the remaining contents of the compartment 20 are hygienically secured avoiding spillage. The underside of a re-attachable seal 28 and top of a circular support for a re-attachable seal 281 comprise an adhesive to secure one to the other; however, other securing means known in the art may be used.

FIG. 3 shows the third of three top views of the first embodiment of the combination condom and personal lubricant container 10. The discussion set forth in this paragraph is limited to the design of the seal. The top wall of the condom compartment 21 comprises a partially affixed seal 29 comprising a tab 27 and a circular support for a partially affixed seal 291, in lieu of a removable seal 25 that is not re-attachable. The drawing depicts an oval-shaped seal 29. The partially affixed seal 29 is opened and closed without removing the seal 29 from the top wall of the compartment 21. By pulling the tab 27 and opening the seal 29, the contents of the compartment 20 are accessed and may be manually removed. The seal 29 may be closed by pressing the seal 29 against the circular support for a partially affixed seal 291. By closing the seal 29, the remaining contents of the compartment 20 are hygienically secured avoiding spillage. The underside of a partially affixed seal 29 and top of the circular support for a partially affixed seal 291 comprise an adhesive to secure one to the other; however, other securing means known in the art may be used.

Figure 4:
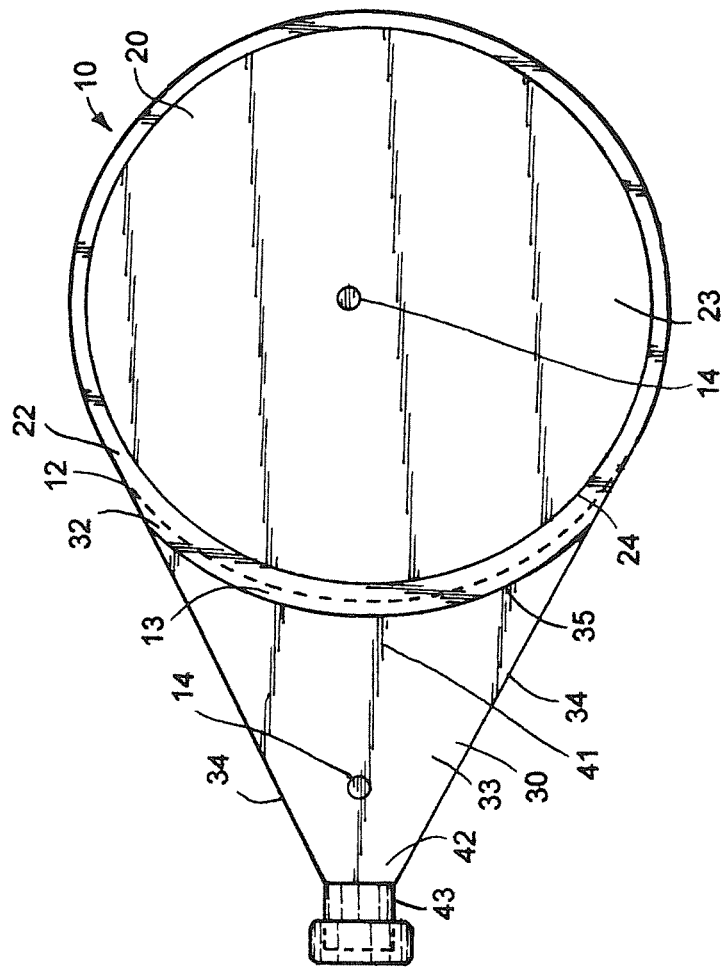
FIG. 4 shows a bottom view of a first embodiment of a combination condom and personal lubricant container.

FIG. 4 shows a bottom view of the first embodiment of a combination condom and personal lubricant container 10. The perforations in the top of the container 12 and the protruding curved edge of the top wall of each compartment 22, 32 are in view.

The condom compartment 20 is positioned at the distal end of the container 10. A cylindrical wall 24 (bottom edge only shown) marks the perimeter of a bottom wall of the compartment 23. A portion of the cylindrical wall 24 faces a curved interior side wall of the personal lubricant compartment 35 (bottom edge only shown). The bottom wall of the condom compartment 23 is substantially flat. The bottom wall of the compartment 23 may comprise a temperature sensing aid 14. The temperature sensing aid 14 allows the temperature of the contents enclosed within the compartment 20 to be monitored when the contents of the compartment 20 are heated by a device in which the container 10 is seated. The temperature sensing aid 14 may be a temperature sensor known in the art or a component known in the art that makes contact with a temperature sensor a part of the heating device.

The personal lubricant compartment 30 is positioned at the proximal end of the container 10. The curved interior side wall 35 (bottom edge only shown), two side walls 34 (bottom edge only shown) separated by the discharge element 43, and the discharge element 43 mark the perimeter of the bottom of the compartment 30. The curved interior side wall of the compartment 35 faces the cylindrical wall of the condom compartment 24. The bottom wall of the compartment 33 is tapered and horizontally positioned in the container 10 and extends away from the bottom horizontal edge of the curved interior side wall 35, the broad end of the funnel 41, toward the discharge element 43, the narrow end of the funnel 42. The bottom wall of the compartment 33 may comprise a temperature sensing aid 14. The temperature sensing aid 14 allows the temperature of the contents enclosed within the compartment 30 to be monitored when the contents of the compartment 30 are heated by a device in which the container 10 is seated. The temperature sensing aid 14 may be a temperature sensor known in the art or a component known in the art that makes contact with a temperature sensor a part of the heating device. The drawing discloses a curved space 13 between the cylindrical wall of the condom compartment 24 and the curved interior side wall of the personal lubricant compartment 35 which may accommodate a heating element of the warming device.

Figure 5:
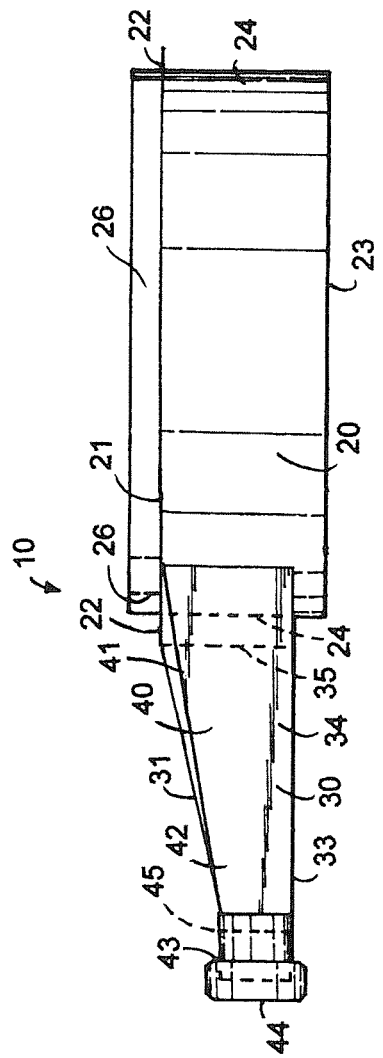
FIG. 5 shows a side view of a first embodiment of a combination condom and personal lubricant container.

FIG. 5 shows a side view of the first embodiment of the combination condom and personal lubricant container 10. The drawing favors the length of the container 10.

The condom compartment 20 is positioned at the distal end of the container 10. The condom compartment 20 comprises a substantially flat top wall 21 (edge only shown) and bottom wall 23 (edge only shown) parallel to one another and a cylindrical wall 24 perpendicular to the top wall 21 and bottom wall 23 said walls hermetically sealed to form an airtight enclosure in which the contents reside. The cylindrical wall 24 faces the curved interior side wall of the personal lubricant compartment 35. The top wall of the compartment 21 comprises the protruding curved edge 22 and, preferably, the raised annular ring 26. The cylinder-shaped condom compartment 20 is deep enough to accommodate one or more condoms and a personal lubricant or sexually stimulating lubricant in which said one or more condoms are immersed.

The personal lubricant compartment 30 is positioned at the proximal end of the container 10. The drawing favors the length of the container 10. The compartment 30 is in the shape of a funnel 40. The top wall of the compartment 31 comprises a protruding curved edge 32 extending away from the curved interior side wall 35. The compartment comprises a sloping top wall 31, a horizontally positioned bottom wall 33 (side edge only shown), two tapered side walls 34 (only one wall shown), and the discharge element 43, the taper terminus for said walls. The compartment 30 also comprises a curved interior side wall 35 marking the broad end of the funnel 41. The curved interior side wall 35 is joined to the top wall 31, bottom wall 33, and each side wall 34 at its top horizontal edge, bottom horizontal edge, and vertical edge, respectively. Said walls and discharge element 43 are hermetically sealed to form an airtight enclosure in which the contents reside. The top wall of the compartment 31 slopes downward diagonally away from the top horizontal edge of the curved interior side wall 35, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 30. Personal lubricant discharged is gravity fed. The discharge element 43 is open-ended and designed to receive a removable dispenser. Before discharging the contents, a protective seal 45 within the discharge element 43 is ruptured presumably with a piercing element of a removable dispenser. The discharge element 43 may also comprise a cap 44 that must be removed from the end of the element 43 before rupturing the protective seal 45.

Figure 6:
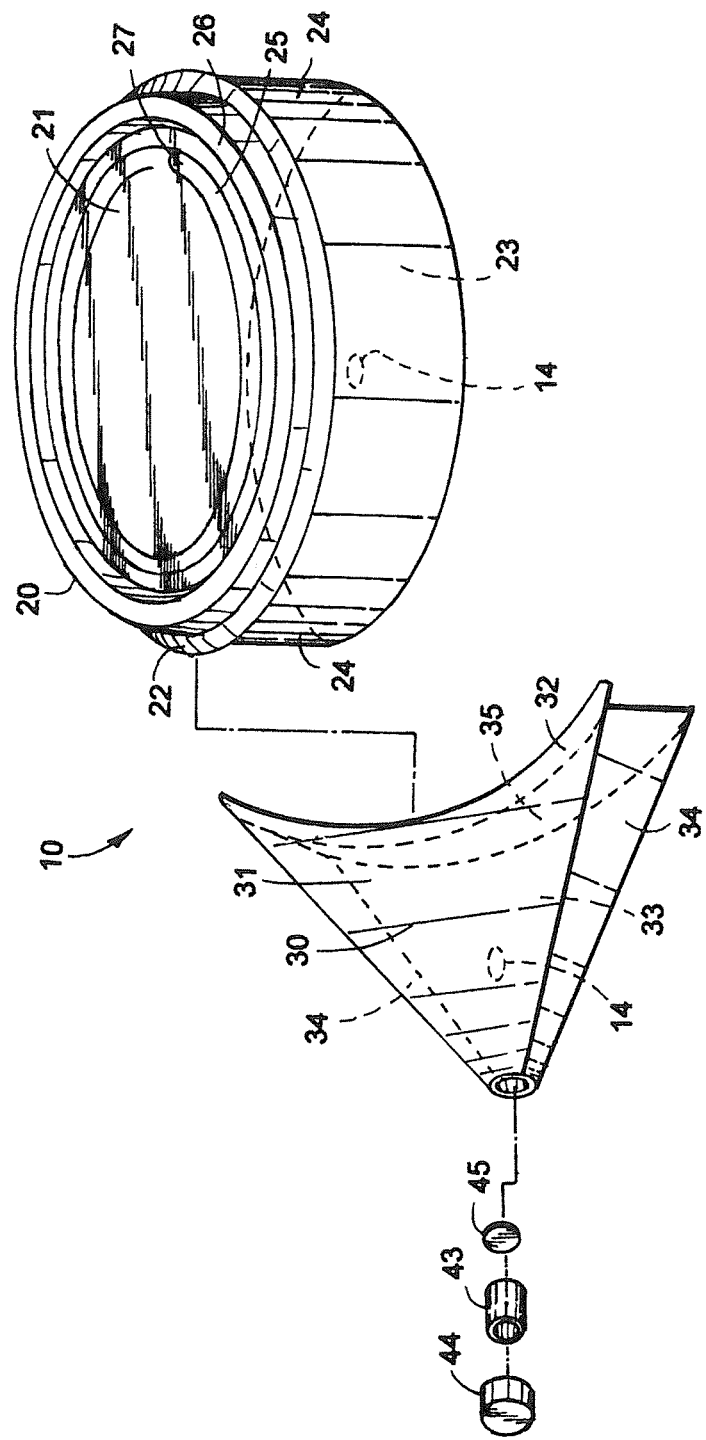
FIG. 6 shows an exploded view of a first embodiment of a combination condom and personal lubricant container.

FIG. 6 shows an exploded view of the first embodiment of the combination condom and personal lubricant container 10. The condom compartment 20 and personal lubricant compartment 30 are separated from another with the aid of perforations in the container 12. The condom compartment 20 is shown to comprise a top wall 21 comprising a removable seal 25 in the shape of an annular strip with a tab 27, a protruding curved edge 22 and a raised annular ring 26 positioned between the seal 25 and the protruding curved edge 22 and a cylindrical wall 24. A bottom wall 23 is hidden but the temperature sensing aid 14 comprising the bottom wall 23 is shown by a dashed oval. In lieu of a removable seal 25, the top wall of the compartment may comprise a removable re-attachable seal 28 (not shown) or a partially affixed seal 29 (not shown). Although the drawing depicts the top wall 21 comprising the raised annular ring 26 and the hidden bottom wall comprising a temperature sensing aid 14, these elements are only preferred. The personal lubricant compartment 30 is shown to comprise a discharge element 43 which is separated from the compartment 30 at the narrow end of the funnel 42. A cap 44 and protective seal 45 are separated from the discharge element 43. The discharge element 43 is an open-ended fitting shown to be cylindrical in shape. The three dimensional shape of the condom compartment 20 and personal lubricant compartment 30 defines the volume of the contents contained therein.

Second Embodiment of a Combination Condom and Personal Lubricant Container—FIGS. 7, 8, 9, 10.

FIGS. 7-10 show various views of an article of manufacture comprising a condom compartment 20 removably adjoined to congruent personal lubricant compartments 130, 150 hereafter referred to as a combination condom and personal lubricant container 110. The container 110 is disposable. The compartments 20, 130, 150 comprising the container 110 are constructed of a flexible, semi-rigid, or rigid packaging material 11 comprising properties that conduct heat such as aluminum. The condom compartment 20 positioned in the center of the container 110 is removably adjoined to congruent personal lubricant compartments 130, 150 flanking the condom compartment at a protruding curved edge of the top wall of each compartment 22, 132, 152 forming a common border. The congruent compartments 130, 150 may be detached from the condom compartment 20 with the aid of perforations in the top of the container 112 arranged in two curved patterns along the common border.

Figure 7:
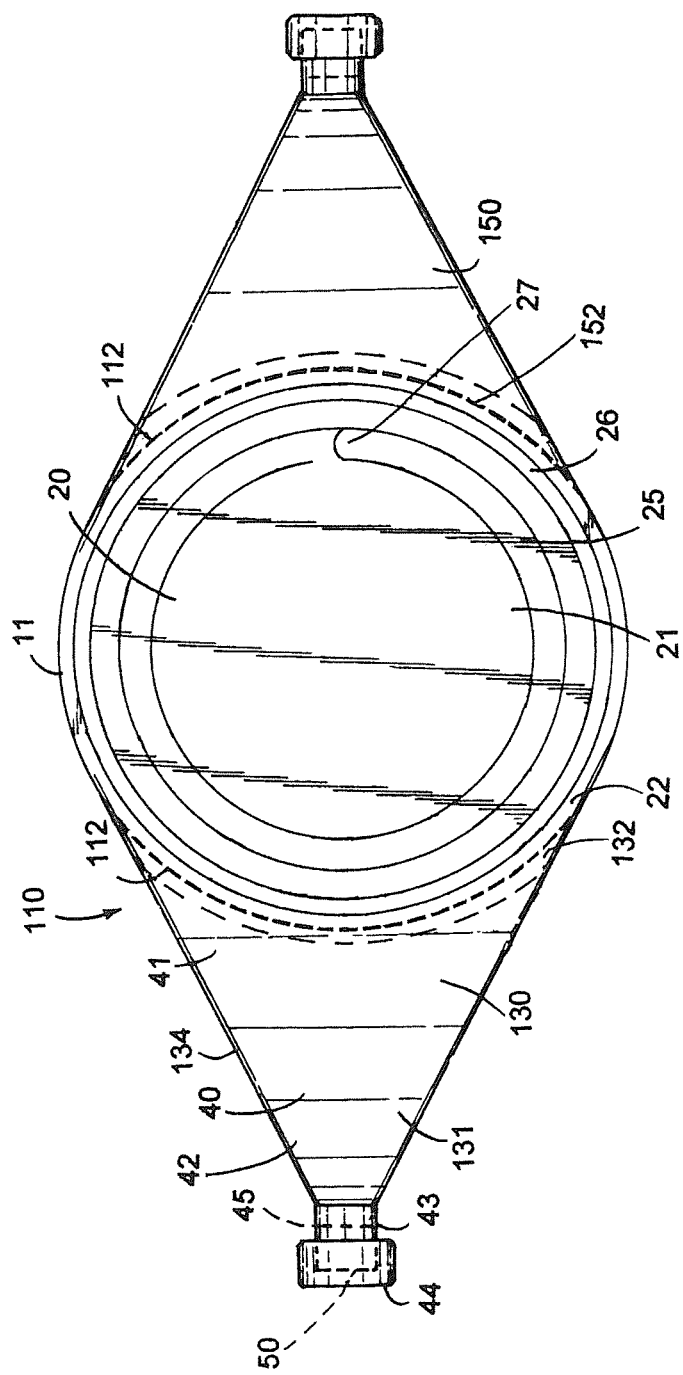
FIG. 7 shows a top view of a second embodiment of a combination condom and personal lubricant container.

FIG. 7 shows a top view of the second embodiment of the combination condom and personal lubricant container 110. The condom compartment 20 is positioned at or near the center of the container 110. The protruding curved edge of the top wall 22 marks the perimeter of the top wall of the compartment 21. The top wall of the condom compartment 21 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. In lieu of a removable seal 25, the top wall of the condom compartment 21 may comprise a removable re-attachable seal 28 or partially affixed seal 29. Refer to FIG. 2 and the description above for a drawing and discussion of the removable re-attachable seal. Refer to FIG. 3 and the description above for a drawing and discussion of the partially affixed seal. The top wall of the condom compartment 21 also comprises a raised annular ring 26. The raised annular ring 26 is positioned between the protruding curved edge of the top wall of the compartment 22 and the removable seal 25. The raised annular ring 26 provides a barrier to the migration of liquid material contained in an open condom compartment 20 when the container 110 is seated in a device used to heat its contents. The raised annular ring 26 helps prevent liquid material from entering the part of a device that heats the contents of the compartments 20, 130, 150.

In lieu of a single personal lubricant compartment 30, two congruent personal lubricant compartments contain personal lubricant or sexually stimulating lubricant hereinafter referred to as PLC-A 130 and PLC-B 150. PLC-A 130 and PLC-B 150 are positioned on opposing ends of the container 110 removably adjoined to the condom compartment 20 at a protruding curved edge of the top wall of each compartment 22, 132, 152. Inasmuch as PLC-A 130 and PLC-B 150 are congruent, only PLC-A 130 is described further.

PLC-A 130 is in the shape of a funnel 40. The protruding curved edge of the top wall of PLC-A 132, two side walls 134 (top edge only shown) separated by a discharge element 43, and the discharge element 43 mark the perimeter of the top of PLC-A 130. The top wall of PLC-A 131 is tapered sloping downward away from a curved interior side wall 135, the broad end of the funnel 41, and terminating at the discharge element 43, the narrow end of the funnel 42, therefore; the broader end 41 is higher than the narrower end of the funnel 42. The downward slope facilitates the flow of personal lubricant and, concomitantly, the emptying of PLC-A 130. Personal lubricant discharged is gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably by a piercing element of the removable dispenser. The discharge element 43 may also comprise a cap 44 that must be removed from the end of the element 43 before rupturing the protective seal 45.

Figure 8:
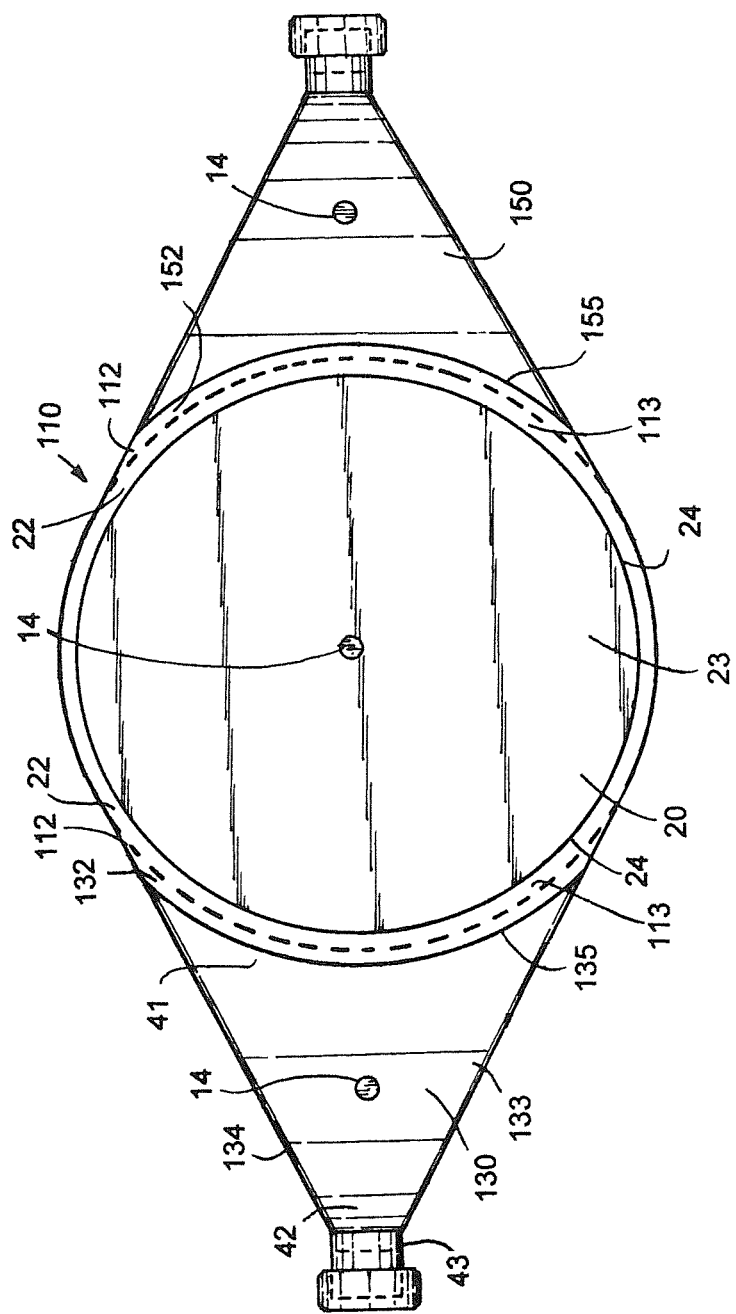
FIG. 8 shows a bottom view of a second embodiment of a combination condom and personal lubricant container.

FIG. 8 shows a bottom view of the second embodiment of the combination condom and personal lubricant container 110. The perforations in the top of the container 112 and the curved edge of the top wall of each compartment 22, 132, 152 are in view.

The condom compartment 20 is positioned at or near the center of the container 110. A bottom wall of the condom compartment 23 is substantially flat. A cylindrical wall 24 (bottom edge only shown) marks the perimeter of the bottom wall of the compartment 23 and faces a curved interior wall of each congruent compartment 135, 155 (bottom edge only shown). The bottom wall of the compartment 23 may comprise a temperature sensing aid 14. The temperature sensing aid 14 allows the temperature of the contents enclosed within the compartment 20 to be monitored when the contents of the compartment 20 are heated by a device in which the container 110 is seated. The temperature sensing aid 14 may be a temperature sensor known in the art or a component known in the art that makes contact with a temperature sensor a part of the heating apparatus.

PLC-A 130 is positioned at an end of the container 110 flanking the condom compartment 20. The curved interior wall 135 (bottom edge only shown), two side walls 134 (bottom edge only shown) separated by a discharge element 43, and the discharge element 43 mark the perimeter of the bottom of PLC-A 130. The curved interior wall of PLC-A 135 faces the cylindrical wall of the condom compartment 24. The bottom wall of the compartment 133 is tapered and horizontally positioned in the container 110 and extends away from the bottom horizontal edge of the curved interior wall 135, the broad end of the funnel 41, toward the discharge element 43, the narrow end of the funnel 42. The bottom wall of the compartment 133 may comprise a temperature sensing aid 14. The temperature sensing aid 14 allows the temperature of the contents enclosed within PLC-A 130 to be monitored when the contents of PLC-A 130 are heated by a device in which the container 110 is seated. The temperature sensing aid 14 may be a temperature sensor known in the art or a component known in the art that makes contact with a temperature sensor a part of the heating device. The drawing discloses two curved spaces 113 between the cylindrical wall of the condom compartment 24 and a curved interior wall of each congruent compartment 135, 155 which may accommodate a heating element of the device.

Figure 9:
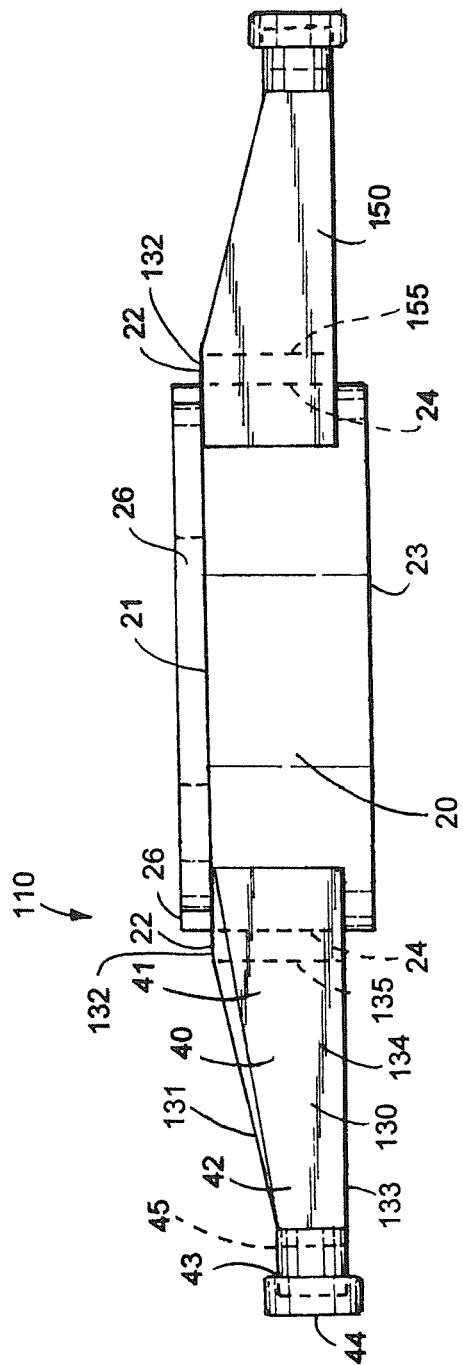
FIG. 9 shows a side view of a second embodiment of a combination condom and personal lubricant container.

FIG. 9 shows a side view of the second embodiment of the combination condom and personal lubricant container 110. The drawing favors the length of the container 110.

The condom compartment 20 is positioned at the distal end of the container 110. The condom compartment 20 comprises a substantially flat top wall 21 (edge only shown) and bottom wall 23 (edge only shown) substantially parallel to one another and a cylindrical wall 24 substantially perpendicular to the top wall 21 and bottom wall 23 hermetically sealed to form an airtight enclosure in which the contents reside. The top wall 21 comprises a protruding curved edge 22. The cylindrical wall 24 faces the curved interior wall of the personal lubricant compartment 35. Preferably, the raised annular ring 26 is positioned on the top wall of the condom compartment 21. The cylinder shaped condom compartment 20 is deep enough to accommodate one or more condoms and a personal lubricant or sexually stimulating lubricant in which said one or more condoms are immersed.

The personal lubricant compartment 130 is positioned at the proximal end of the container 10. The compartment 130 is in the shape of a funnel 40. The compartment comprises a sloping top wall 131, a horizontally positioned bottom wall 133 (side edge only shown), two tapered side walls 134 (only one wall shown), and the discharge element 43, the taper terminus for said walls. The compartment 130 also comprises a curved interior wall 135 marking the broad end of the funnel 41. The curved interior side wall 135 is joined to the top wall 131, bottom wall 133, and each side wall 134 at its top horizontal edge, bottom horizontal edge, and vertical edge, respectively. Said walls and discharge element 43 are hermetically sealed to form an airtight enclosure in which the contents reside. The top wall of the compartment 131 slopes downward diagonally away from the top horizontal edge of the curved interior side wall 135, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 130. Personal lubricant discharged is, for the most part, gravity fed. The narrow end of the funnel 42 comprises an open-ended discharge element 43 or fitting designed to receive a removable dispenser. Before discharging the contents, a protective seal 45 within the discharge element 43 is ruptured presumably with a piercing element of the removable dispenser. The discharge element 43 may also comprise a cap 44 that must be removed from the end of the element 43 before rupturing the protective seal 45.

Figure 10:
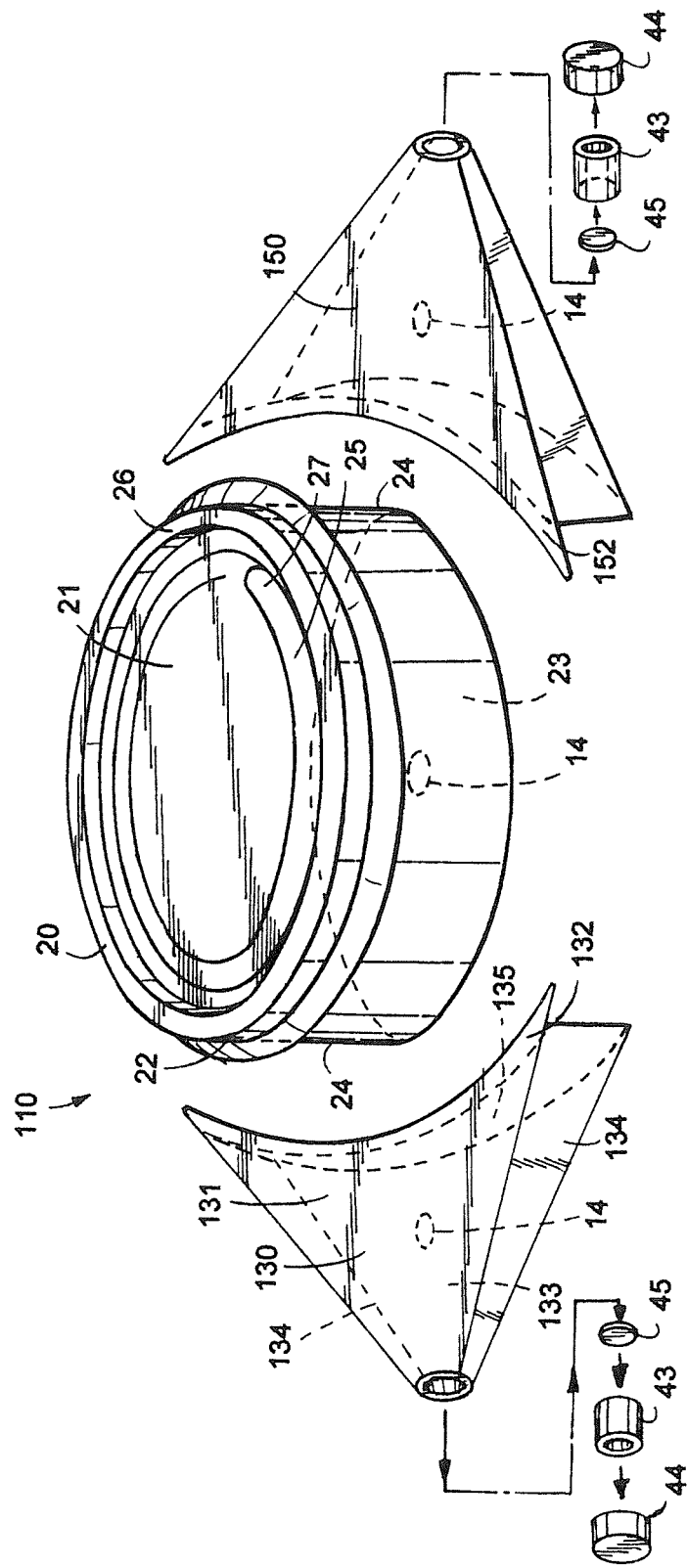
FIG. 10 shows an exploded view of a second embodiment of a combination condom and personal lubricant container.

FIG. 10 shows an exploded view of the second embodiment of the combination condom and personal lubricant container 110. The condom compartment 20 and the congruent personal lubricant compartments 130, 150 are separated from another with the aid of perforations in the container 112. The condom compartment 20 is shown to comprise a top wall 21 comprising a removable seal 25 in the shape of an annular strip with a tab 27, a protruding curved edge 22 and a raised annular ring 26 positioned between the seal 25 and the protruding curved edge 22 and a cylindrical wall 24. A bottom wall 23 is hidden but the temperature sensing aid 14 comprising the bottom wall 23 is shown by a dashed oval. In lieu of a removable seal 25, the top wall of the compartment may comprise a removable re-m, attachable seal 28 (not shown) or a partially affixed seal 29 (not shown). Although the drawing depicts the top wall 21 comprising the raised annular ring 26 and the hidden bottom wall comprising a temperature sensing aid 14, these elements are only preferred. Each congruent personal lubricant compartment 130, 150 is shown to comprise a discharge element 43 which is separated from the compartment 130 at the narrow end of the funnel 42. A cap 44 and protective seal 45 are separated from the discharge element 43. The discharge element 43 is open-ended fitting shown to be cylindrical in shape. The three dimensional shape of the condom compartment 20 and the congruent personal lubricant compartments 130, 150 defines the volume of the contents contained therein.

Third Embodiment of a Combination Condom and Personal Lubricant Container—FIGS. 11, 12, 13, 14.

FIGS. 11-14 show various views of an article of manufacture comprising a condom compartment 220 removably adjoined to a personal lubricant compartments 230 hereinafter referred to as a combination condom and personal lubricant container 210. The container 210 is in the shape of a pentagon. The container 210 is disposable. The compartments 220, 230 comprising the container 210 are constructed of a flexible, semi-rigid, or rigid packaging material 11 comprising properties that conduct heat such as aluminum. The condom compartment 220 is removably adjoined to a personal lubricant compartment 230 at a protruding straight edge of the top wall of each compartment 222, 232 forming a common border. The compartments 220, 230 may be detached from one another with the aid of perforations in the top of the container 212 arranged in a straight pattern along the common border.

Figure 11:
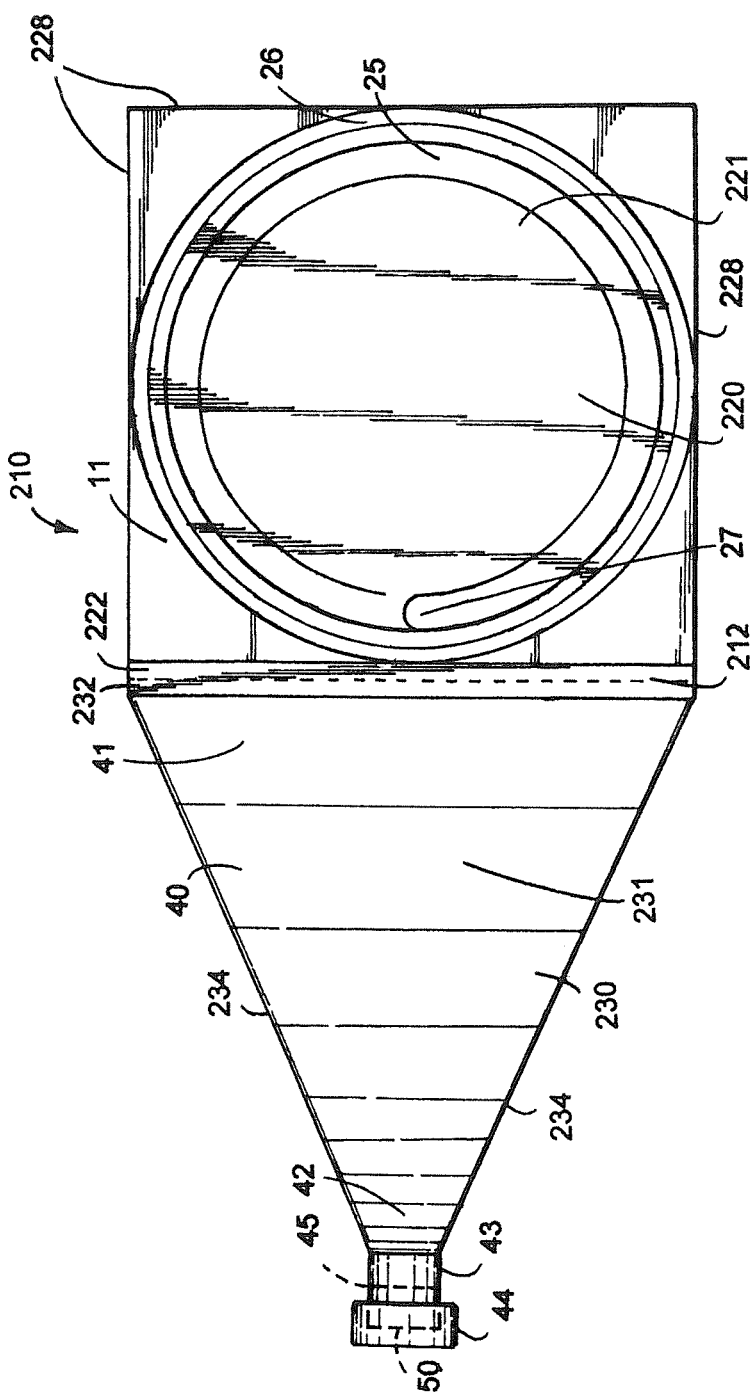
FIG. 11 shows a top view of a third embodiment of a combination condom and personal lubricant container.

FIG. 11 shows a top view of a third embodiment of the combination condom and personal lubricant container 210.

The condom compartment 220 is positioned at the distal end (in relation to the point of discharge 50 of the contents in the personal lubricant compartment 230) of the container 210. The top view shows the top wall of the condom compartment 221 to be rectangular in shape. The top wall 221 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. The top wall of the condom compartment 221 may comprise a removable re-attachable seal 28 or partially affixed seal 29 in lieu of a removable seal 25. Refer to FIG. 2 and the description above for a drawing and discussion of the removable re-attachable seal. Refer to FIG. 3 and the description above for a drawing and discussion of the partially affixed seal. The top wall of the condom compartment 221 also comprises a protruding straight edge 222 extending out from a rectangular side wall 229. Three rectangular side walls 228 (top edge only shown) and the protruding straight edge of the top wall of the compartment 222 mark the perimeter of the top wall of the compartment 221. Preferably, the top wall of the condom compartment 221 also comprises a raised annular ring 26. The raised annular ring 26 is positioned between the perimeter of the top wall of the compartment 221 and the removable seal 25. The raised annular ring 26 provides a barrier to the migration of liquid material contained in an open condom compartment 220 when the container 210 is seated in a device used to heat its contents. The raised annular ring 26 helps prevent liquid material from entering the part of a device that heats the contents of the compartments 220, 230.

The proximal end of the container 210 comprises a personal lubricant compartment 230. The personal lubricant compartment 230 is in the shape of a funnel 40. The top wall of the personal lubricant compartment 231 comprises a protruding straight edge 232 extending away from a rectangular side wall 235 (shown by a dashed line). The protruding straight edge 232, two side walls 234 (top edge only shown) separated by a discharge element 43 and the discharge element 43 mark the perimeter of the top of the personal lubricant compartment 230. The top wall of the compartment 231 is tapered sloping downward from the rectangular side wall 232, the broad end of the funnel 41, and terminating at the discharge element 43, the narrow end of the funnel, therefore, the broader end 41 is higher than the narrower end of the funnel 42. The downward slope facilitates the flow of personal lubricant and, concomitantly, the emptying of the personal lubricant compartment 230. Personal lubricant discharged is gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably with a piercing element of a removable dispenser. The discharge element 43 may also comprise a cap 44 that must be removed from the end of the element 43 before rupturing the protective seal 45.

Figure 12:
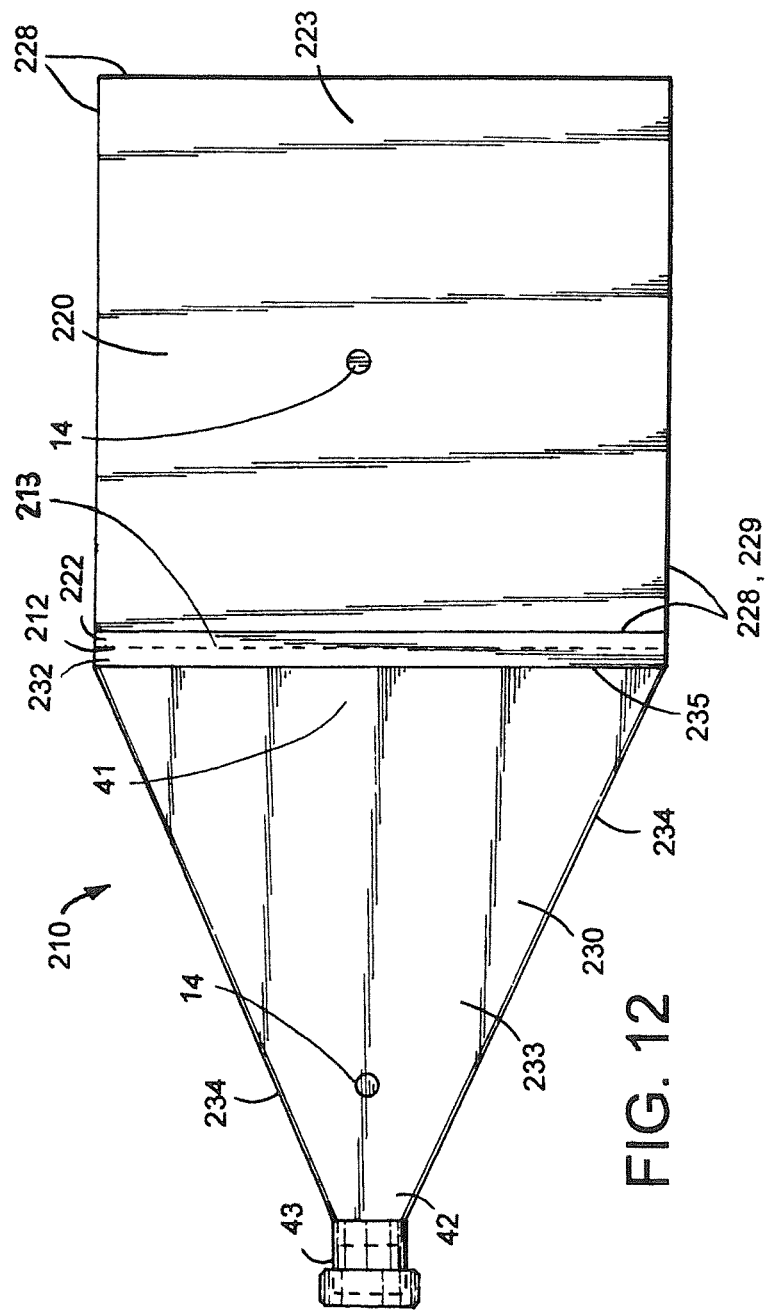
FIG. 12 shows a bottom view of a third embodiment of a combination condom and personal lubricant container.

FIG. 12 shows a bottom view of the third embodiment of the combination condom and personal lubricant container 210. The perforations in the top of the container 212 and the protruding straight edge of the top wall of each compartment 222, 232 are in view.

The distal end of the container 210 comprises the condom compartment 220. The bottom wall of the compartment 223 is substantially flat and rectangular in design. Four rectangular side walls 228 (bottom edge only shown) located about the condom compartment 220 mark the perimeter of the bottom wall of the compartment 223. A rectangular interior side wall 229 (bottom edge only shown) faces a rectangular interior side wall of the personal lubricant compartment 235 (bottom edge only shown) each wall substantially equal in length and equidistant from one another. The bottom wall of the compartment 223 may comprise a temperature sensing aid 14. The temperature sensing aid 14 allows the temperature of the contents enclosed within the compartment 220 to be monitored when the contents of the compartment 220 are heated by a device in which the container 210 is seated. The temperature sensing aid 14 may be a temperature sensor known in the art or a component known in the art that makes contact with a temperature sensor a part of the heating device.

The proximal end of the container 210 comprises the personal lubricant compartment 230. The bottom wall of the compartment 233 is triangular in shape. A rectangular interior side wall 235 (bottom edge only shown), two side walls 234 (bottom edge only shown) separated by the discharge element 43, and the discharge element 43 mark the perimeter of the bottom of the compartment 230. The rectangular interior side wall 235 faces the rectangular interior side wall of the condom compartment 229 said walls substantially equal in length and equidistant from one another. The bottom wall of the compartment 233 is tapered and horizontally positioned in the container 210 and extends away from the bottom horizontal edge of the rectangular side wall 235, the broad end of the funnel 41, toward the discharge element 43, the narrow end of the funnel 42. The bottom wall of the compartment 233 may comprise a temperature sensing aid 14. The temperature sensing aid 14 allows the temperature of the contents enclosed within the compartment 230 to be monitored when the contents of the compartment 230 are heated by a device in which the container 210 is seated. The temperature sensing aid 14 may be a temperature sensor known in the art or a component known in the art that makes contact with a temperature sensor a part of the heating device. The drawing discloses a straight space 213 between the opposing interior rectangular side walls of the condom compartment 229 and the personal lubricant compartment 235 which may accommodate a heating element of the device.

Figure 13:
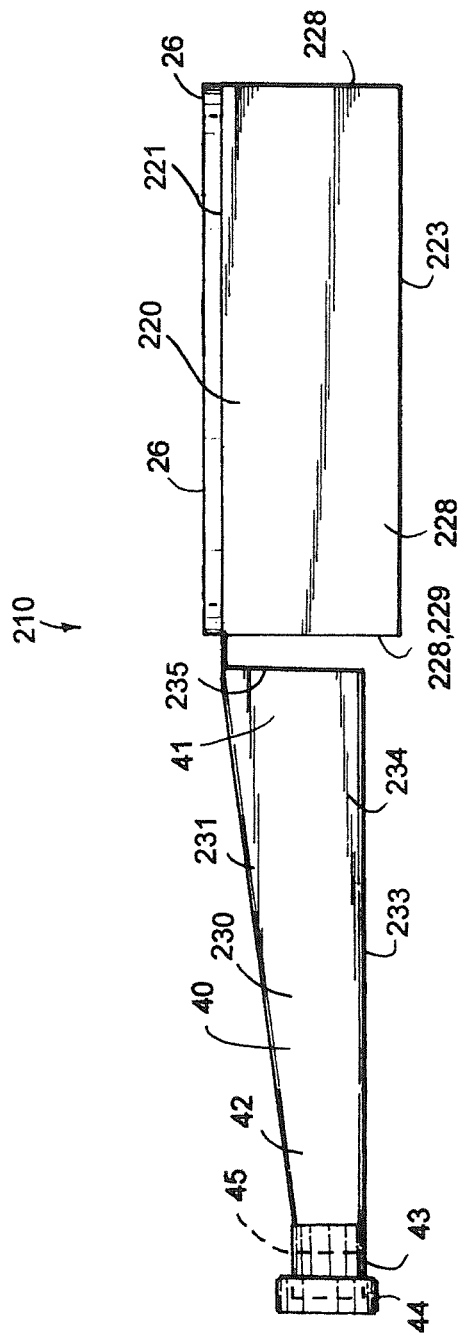
FIG. 13 shows a side view of a third embodiment of a combination condom and personal lubricant container.

FIG. 13 shows a side view of the third embodiment of the combination condom and personal lubricant container 210. The drawing favors the length of the container 210.

The distal end of the container 210 comprises the condom compartment 220. The condom compartment 220 is in the shape of a rectangular box. The walls comprising the condom compartment 220 are hermetically sealed to form an airtight enclosure in which the contents reside. The drawing shows the side of a rectangular side wall 228 comprising a substantially flat top wall 221 (top edge only shown) and bottom wall 223 (bottom edge only shown) and two rectangular side walls 228 (side edge only shown). One of the rectangular side walls 228 is a rectangular interior side wall 229 facing a rectangular interior side wall of the personal lubricant compartment 235. The raised annular ring 26 is positioned on the top wall of the condom compartment 221. The condom compartment 220 is deep enough to accommodate one or more condoms and a personal lubricant or sexually stimulating lubricant in which said one or more condoms are immersed.

The proximal end of the container 210 comprises the personal lubricant compartment 230. The personal lubricant compartment 230 is in the shape of a funnel 40. The compartment comprises a sloping top wall 231, a horizontally positioned bottom wall 233 (side edge only shown), two tapered side walls 234 (only one wall shown), and the discharge element 43, the taper terminus for said walls. The compartment 230 also comprises a rectangular interior side wall 235 marking the broad end of the funnel 41. The rectangular interior side wall 235 is joined to the top wall 231, bottom wall 233, and each side wall 234 at its top horizontal edge, bottom horizontal edge, and vertical edge, respectively. Said walls and discharge element 43 are hermetically sealed to form an airtight enclosure in which the contents reside. The top wall of the compartment 231 slopes downward diagonally away from the top horizontal edge of the rectangular interior side wall 235, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 230. Personal lubricant discharged is, for the most part, gravity fed. The narrow end of the funnel 42 comprises an open-ended discharge element 43 or fitting designed to receive a removable dispenser. Before discharging the contents, a protective seal 45 within the discharge element 43 is ruptured presumably with a piercing element of the removable dispenser. The discharge element 43 may also comprise a cap 44 that must be removed from the end of the element 43 before rupturing the protective seal 45.

Figure 14:
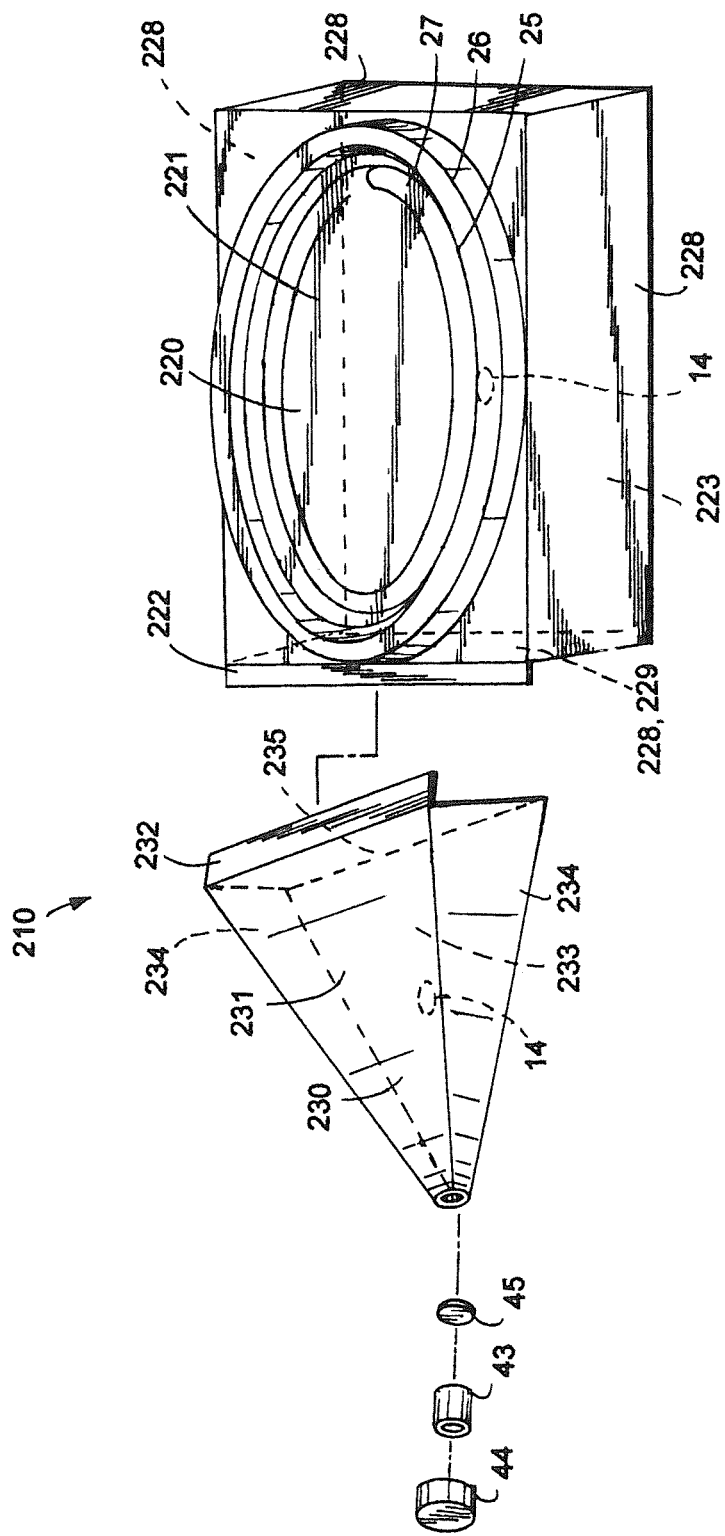
FIG. 14 shows an exploded view of a third embodiment of a combination condom and personal lubricant container.

FIG. 14 shows an exploded view of the third embodiment of the combination condom and personal lubricant container 210. The condom compartment 220 and personal lubricant compartment 230 are separated from one another with the aid of perforations in the container 212. The rectangular shaped condom compartment 220 is shown to comprise a top wall 221 comprising a removable seal 25 in the shape of an annular strip with a tab 27, a protruding straight edge 222 and a raised annular ring 26 positioned between the seal 25 and the protruding straight edge 222 and rectangular side walls 228. A rectangular side wall 228 and the bottom wall 23 are hidden; however, the temperature sensing aid 14 comprising the bottom wall 223 is shown by a dashed oval. In lieu of a removable seal 25, the top wall of the compartment may comprise a removable re-attachable seal 28 (not shown) or a partially affixed seal 29 (not shown). Although the drawing depicts the top wall 221 comprising the raised annular ring 26 and the hidden bottom wall 223 comprising a temperature sensing aid 14, these elements are only preferred. The personal lubricant compartment 230 is shown to comprise a discharge element 43 which is separated from the compartment 230 at the narrow end of the funnel 42. A cap 44 and protective seal 45 are separated from the discharge element 43. The discharge element 43 is an open-ended fitting shown to be cylindrical in shape. The three dimensional shape of the condom compartment 20 and personal lubricant compartment 30 defines the volume of the contents contained therein.

Operation—First, Second and Third Embodiments of a Combination Condom and Personal Lubricant Container 1. Assembling the Combination Condom and Personal Lubricant Container.

The first, second and third embodiments of the combination condom and personal lubricant container 10, 110, 210 comes assembled. The container 10, 110, 210 comprises a compartment 20, 220 enclosing one or more condoms and a personal lubricant or sexually stimulating lubricant in which said one or more condoms are immersed and a personal lubricant compartment 30, 130, 230 enclosing a personal lubricant. Alternatively, the personal lubricant compartment 30, 130, 230 may enclose sexually stimulating lubricant. The contents of the compartments are used in sexual activities.

The condom is preferably a male condom known in the art that is sold over the counter under various brand names. Personal lubricant includes a lubricant sold over the counter under various brand names including KY, Durex, Astroglide, and Liquid Silk and is not limited to water-based lubricants.

2. Removing or Discharging the Contents of the Combination Condom and Personal Lubricant Container.

The first, second and third embodiments of the combination condom and personal lubricant container 10, 110, 210 comprise a condom compartment and at least one personal lubricant compartment each compartment comprising the means to access and remove or dispense the contents.

The top wall of the condom compartment 21, 221 comprises one of the following seals. It comprises a removable seal 25 in the shape of an annular strip with a tab 27, a removable re-attachable seal 28 with a tab 27 or a partially affixed seal 29 with a tab 27. By pulling the tab 27 and removing or opening the seal 25, 28, 29, the contents of the compartment 20, 220 are accessed and may be removed manually. The removable seal 25 is not re-attachable to the top wall of the compartment 21, 221. The removable re-attachable seal 28 may be re-attached to the top wall 21, 221 by pressing the seal against the circular support for a re-attachable seal 281. By re-attaching the seal 28, the remaining contents of the compartment 20, 220 are hygienically secured avoiding spillage. The underside of a re-attachable seal 28 and top of a circular support for a re-attachable seal 281 comprise an adhesive to secure one to the other; however, other securing means known in the art may be used. The partially affixed seal 29 is opened and closed without removing the seal 29 from the top wall 21, 221. The seal 29 may be closed by pressing the seal 29 against the circular support for a partially affixed seal 291. By closing the seal 29, the remaining contents of the compartment 20 are hygienically secured avoiding spillage. The underside of a partially affixed seal 29 and top of a circular support for a partially affixed seal 291 comprise an adhesive to secure one to the other; however, other securing means known in the art may be used.

The contents of the personal lubricant compartment 30, 130, 230 are discharged by activating a removable dispenser. The personal lubrication compartment 30, 130, 230 comprises a funnel 40 which comprises an open-ended discharge element 43 or fitting attached to the narrow end of the funnel 42 designed to receive a removable dispenser. Before discharging personal lubricant, a protective seal 45 within the discharge element 43 is ruptured presumably with a piercing element of the dispenser. The discharge element 43 may also comprise a cap 44 that must be removed from the end of the element 43 before rupturing the protective seal 45. The dispenser may be a component of a device used to heat the contents of the compartment 30, 230.

3. Heating the Contents of the Combination Condom and Personal Lubricant Container.

The first, second and third embodiments of the combination condom and personal lubricant container 10, 110, 210 comprise a condom compartment and at least one personal lubricant compartment each compartment constructed of a flexible, semi-rigid, or rigid packaging material comprised of properties that conduct heat 11. The container 10, 110, 210 may be seated in a warming device for the purpose of heating the contents of the compartments to a desired temperature prior to removal or discharge. A condom is warmed as a result of being immersed in the liquid material that is itself warmed when the condom compartment 20, 220 is heated by a warming device. Each compartment may comprise a temperature sensing aid 14 allowing the temperature of the contents to be monitored when heated by a device in which the container 10, 110, 210 is seated. The temperature sensing aid 14 may be a temperature sensor known in the art or a component known in the art that makes contact with a temperature sensor a part of the heating device.

Figure 15:
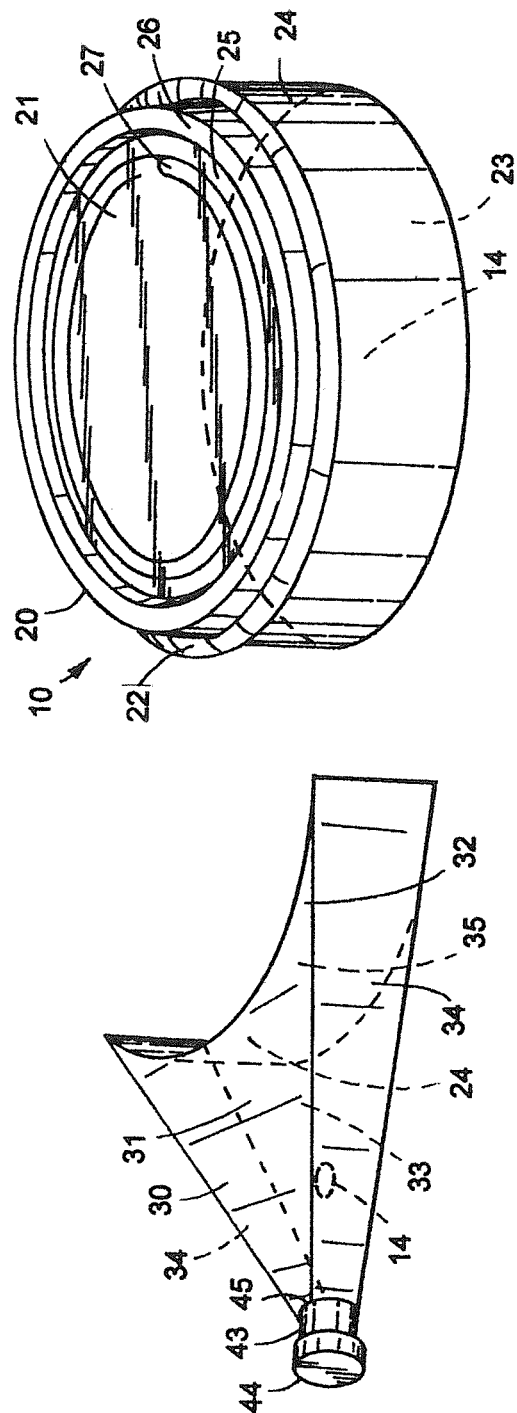
FIG. 15 shows a perspective view of a first embodiment of a combination condom compartment and personal lubricant compartment kit.

First Embodiment of a Combination Condom Compartment and Personal Lubricant Compartment Kit—FIG. 15.

FIG. 15 shows a perspective view of a first embodiment of a combination condom compartment and personal lubricant compartment kit 310. The kit 310 comprises at least one condom compartment 20 wherein said at least one condom compartment 20 is associated with at least one personal lubricant compartment 30. The elements of the kit 310, at least one condom compartment 20 and at least one personal lubricant compartment 30, are combined but not attached. The elements may come in a package, box, or other container (not shown).

Figure 16:
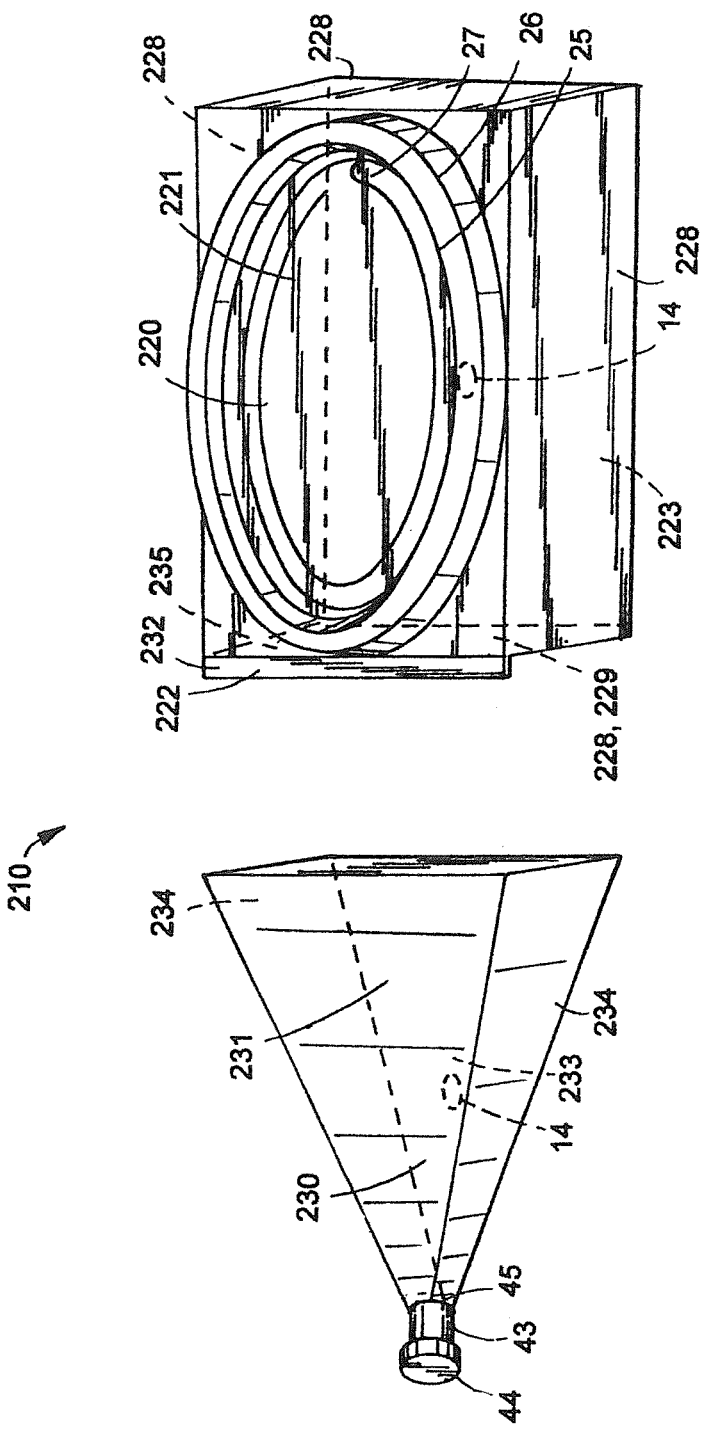
FIG. 16 shows a perspective view of a second embodiment of a combination condom compartment and personal lubricant compartment kit.

Second Embodiment of a Combination Condom Compartment and Personal Lubricant Compartment Kit—FIG. 16.

FIG. 16 shows a perspective view of a second embodiment of a combination condom compartment and personal lubricant compartment kit 410. The kit 410 comprises at least one condom compartment 220 wherein said at least one condom compartment 220 is associated with at least one personal lubricant compartment 230. The elements of the kit 410, at least one condom compartment 220 and at least one personal lubricant compartment 230, are combined but not attached. The elements may come in a package, box or other container (not shown).

Operation—First and Second Embodiments of the Combination Condom Compartment and Personal Lubricant Compartment Kit 1. Assembling the Combination Condom and Personal Lubricant Kit.

Preferably, the first and second embodiments of the combination condom compartment and personal lubricant compartment kit 310, 410 may come in a package, box or other container. The contents of the compartments 20, 30, 220, 230 comprising the kits are used in sexual activities.

The condom compartment 20, 220 encloses one or more condoms and a personal lubricant or sexually stimulating lubricant in which said one or more condoms are immersed. The condom is preferably a male condom known in the art. The personal lubricant compartment 30, 230 contains personal lubricant or, alternatively, sexually stimulating lubricant. Personal lubricant includes a lubricant sold under the brand name KY, Durex, Astroglide, Liquid Silk, among others, and is not limited to water-based lubricants.

2. Removing or Discharging the Contents of the Condom and Personal Lubricant Comprising the Kit.

Refer to the description above regarding a discussion about removing the contents from the condom compartment. Refer to the description above regarding a discussion about discharging the contents from the personal lubricant compartment.

3. Heating the Contents of the Condom Compartment and Personal Lubricant Compartment Comprising the Kit.

Refer to the description above regarding a discussion about heating the contents of the condom compartment prior to removal and use. Refer to the description above regarding a discussion about heating the contents of the personal lubricant compartment prior to discharge and use.

Figure 17:
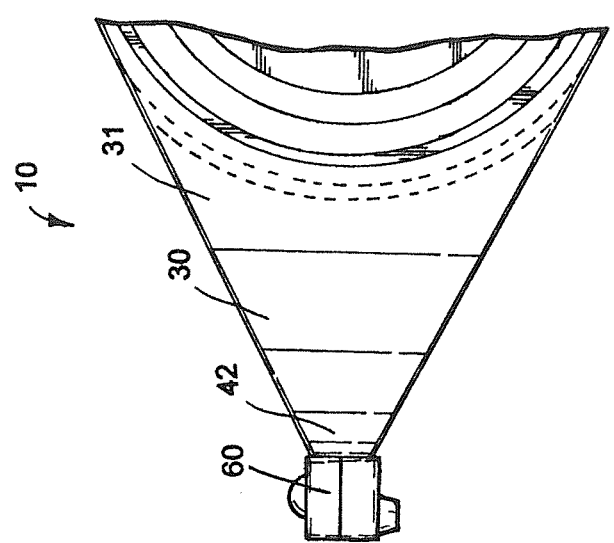
FIG. 17 shows a perspective view of a personal lubricant compartment comprising a permanently attached dispenser.

Alternate Embodiment of a Personal Lubricant Compartment Comprising a Permanently Attached Dispenser—FIG. 17.

FIG. 17 shows a perspective view of a personal lubricant compartment 30 comprising a permanently attached dispenser 60. The drawing favors the top wall of the personal lubricant compartment 31 and the portion of the compartment 30 comprising the funnel 40. The narrow end of the funnel 42 comprises a permanently attached dispenser 60. The permanently attached dispenser is one known in the art.

The other embodiments of a personal lubricant compartment 130, 230 may also comprise a permanently attached dispenser 60.

Operation—Alternate Embodiment of a Personal Lubricant Compartment Comprising a Permanently Attached Dispenser 1. Assembling of the Permanently Attached Dispenser onto the Personal Lubricant Compartment.

The alternate embodiment of the personal lubricant compartment 30 comes assembled.

2. Removing or Discharging the Contents of the Personal Lubricant Compartment.

The contents of a personal lubricant compartment 30 are discharged by activating the permanently attached dispenser 60.

Heatable Personal Lubricant Dispenser—FIGS. 18-28

Various embodiments of a heatable personal lubricant dispenser in accordance with various embodiments of the present invention will now be described in reference to FIGS. 18-28. The dispenser is preferably used with personal lubricants used in sexual activities, but it will be appreciated by those skilled in the art that the dispenser can be used with or adapted for use with other types of personal lubricants, lotions, oils, creams, etc. Moreover, the dispenser is preferably used in connection with a control device, such as a condom warming device, a personal lubricant warming device, or a combination condom and personal lubricant device. Some non-limiting examples of such a control device are described in U.S. patent application Ser. No. 12/989,647, filed on Apr. 8, 2011 and entitled "Device for Heating Products Used in Sexual Activities," which is hereby incorporated by reference in its entirety. The dispenser described herein replaces the fluid dispenser 402, 602 described in the '647 patent application.

As will be described in more detail below, the present invention provides a personal lubricant dispenser that includes an enclosure, a pre-delivery chamber disposed within the enclosure, one or more heating elements disposed within the enclosure proximate to the pre-delivery chamber, an electrical connector disposed on an exterior of the enclosure and electrically connected to the one or more heating elements, an inlet cavity disposed within the enclosure above a portion of the pre-delivery chamber, a piercing element attached to the inlet cavity and accessible from the exterior of the enclosure, a inlet valve (normally closed) disposed within the enclosure and connecting the inlet cavity to the pre-delivery chamber, a inlet actuator disposed on the exterior of the enclosure and operably connected to the inlet valve to open the inlet valve, an outlet cavity disposed within the enclosure below a portion of the pre-delivery chamber, an outlet valve (normally closed) disposed within the enclosure and connecting the outlet cavity to the pre-delivery chamber, an outlet actuator disposed on the exterior of the enclosure and operably connected to the outlet valve to open the outlet valve, and a spout disposed on or within the exterior of the enclosure and connected to the outlet cavity.

In addition, the present invention provides a system that includes a dispenser and a control unit. The dispenser includes an enclosure, a connection interface disposed on the enclosure, a pre-delivery chamber disposed within the enclosure, one or more heating elements disposed within the enclosure proximate to the pre-delivery chamber, an electrical connector disposed on or within the connection interface and electrically connected to the one or more heating elements, an inlet cavity disposed within the enclosure above a portion of the pre-delivery chamber, a piercing element disposed on or within the connection interface and attached to the inlet cavity and accessible from the exterior of the enclosure, a inlet valve (normally closed) disposed within the enclosure and connecting the inlet cavity to the pre-delivery chamber, a inlet actuator disposed on the exterior of the enclosure and operably connected to the inlet valve to open the inlet valve, an outlet cavity disposed within the enclosure below a portion of the pre-delivery chamber, an outlet valve (normally closed) disposed within the enclosure and connecting the outlet cavity to the pre-delivery chamber, an outlet actuator disposed on the exterior of the enclosure and operably connected to the outlet valve to open the outlet valve, and a spout disposed on or within the exterior of the enclosure and connected to the outlet cavity. The control device is removeably connected to the connection interface of the dispenser. The control device includes a power source, an electrical circuit electrically connected to the power source and the electrical connector to control a temperature of a personal lubricant within at least the pre-delivery chamber of the dispenser, a personal lubricant container having a discharge element such that the piercing element of the dispenser is shaped to receive the discharge element and break a seal protecting the personal lubricant within the personal lubricant container and the personal lubricant flows through the piercing element into the inlet cavity of the dispenser. The control device can be a condom warming device, a personal lubricant warming device, or a combination condom and personal lubricant device, etc. (see e.g., the '647 patent application).

Although not explicitly shown in the FIGURES, an additional electrical circuit can be installed within the enclosure and electrically connected to the electrical connector, the one or more heating elements and the temperature probe(s) to control a temperature of a personal lubricant. This circuit can be in addition to the control circuit of the control unit. Moreover, the various heated chambers are preferably made of a heat conducting material, such as aluminum, etc.

Figure 18:
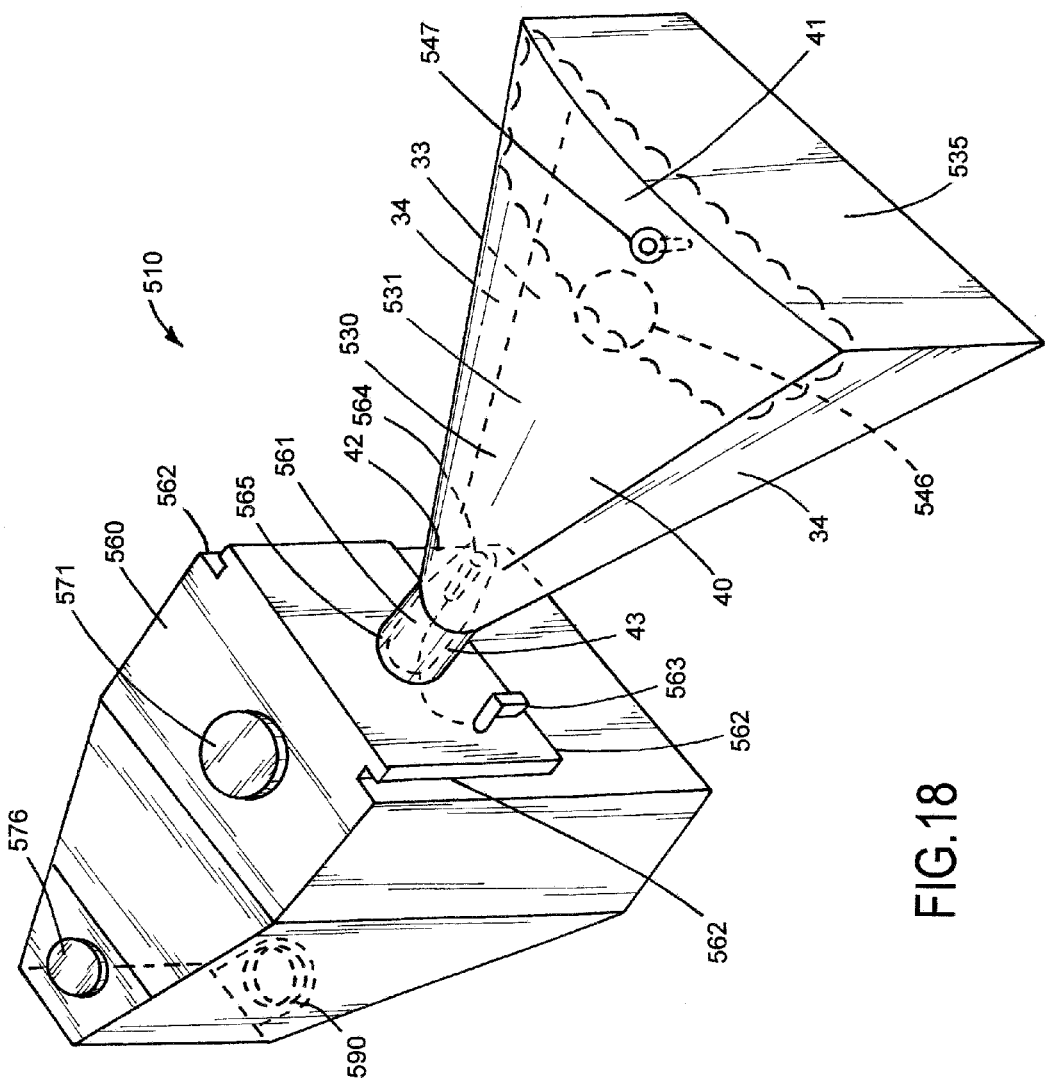
FIG. 18 shows a perspective view of a first embodiment of a personal lubricant container comprising a heatable single chamber dispenser.
Figure 19:
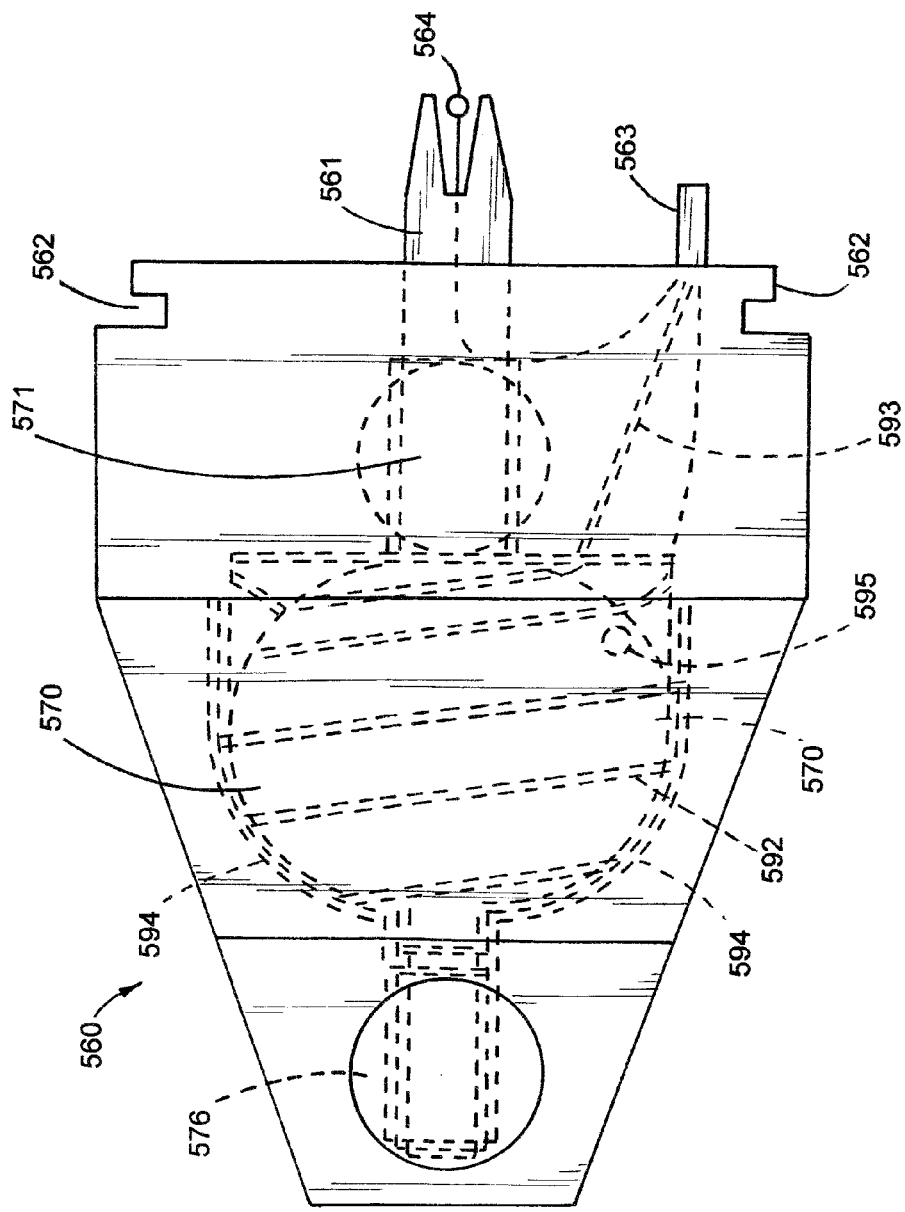
FIG. 19 shows a top view of a heatable single chamber dispenser.
Figure 20:
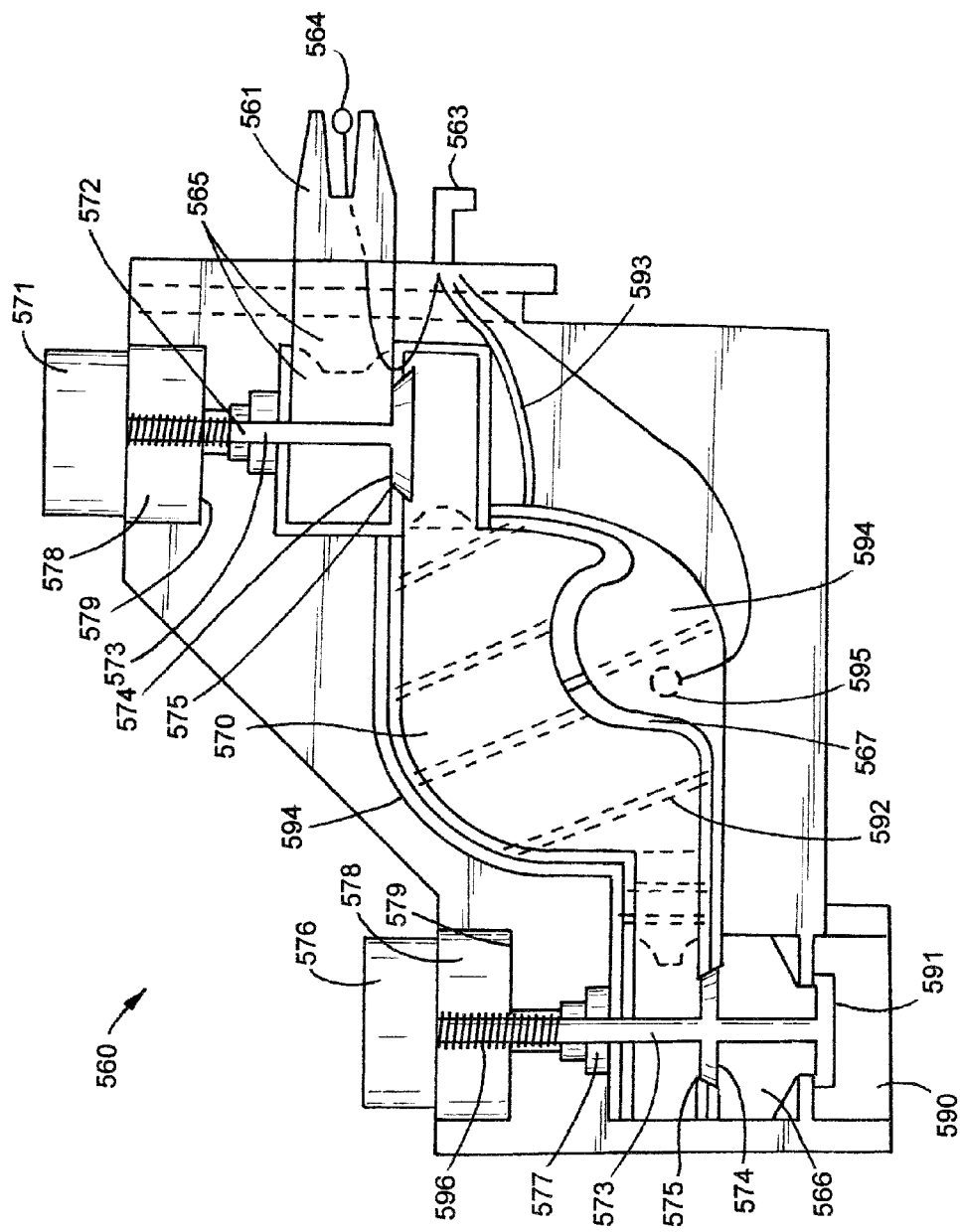
FIG. 20 shows a cross-sectional view of a heatable single chamber dispenser.

First Embodiment of a Personal Lubricant Container Comprising of a Heatable Single Chamber Dispenser—FIGS. 18, 19, 20

FIG. 18 shows a perspective view of a first embodiment of a personal lubricant container comprising a heatable single chamber dispenser 510, hereinafter referred to as "PL container/single chamber dispenser." The heatable single chamber dispenser 560, hereinafter referred to as "single chamber dispenser," is secured to the personal lubricant container 530, hereinafter referred to as "PL container," by means of inserting a piercing element 561 comprising the single chamber dispenser into a discharge element 43 comprising the PL container. Preferably, the single chamber dispenser 560 is removably secured to the PL container 530 and re-usable. Alternatively, the single chamber dispenser 560 is permanently secured to the PL container, and, accordingly, the PL container/single chamber dispenser 510 is disposable.

The chassis or enclosure of the single chamber dispenser 560 is principally constructed of a rigid material, such as molded plastic, comprising insulating or non-conducting properties. The single chamber dispenser 560 comprises a front and rear wall, a top and bottom wall and two side walls. The single chamber dispenser 560 comprises a single heatable pre-delivery chamber within which a personal lubricant is heated. The single chamber dispenser 560 functions as a heated conduit either maintaining the temperature of personal lubricant received from and previously heated within the container 530 or as a heated conduit raising the temperature of personal lubricant received from and previously unheated within the container 530.

FIG. 18 shows the single chamber dispenser 560. Various elements comprising the dispenser 560 are pictured including a piercing element 561 protruding from an inlet cavity 565 located within the front wall, a temperature probe 564 located within the hollow piercing element 561, three grooved joinders 562 two vertically positioned on the side walls nearest the front wall and one horizontally positioned below the piercing element 561 on the front wall, an electrical circuitry connector 563 located on the front wall, two actuator buttons 571, 576 located on the top wall and a spout 590, marked by dashed lines, located on the bottom wall. The spout 590 can be an opening in the enclosure (as shown) or protrude outward from the enclosure. The piercing element 561 is accessible from an exterior of the enclosure. The three grooved joinders 562 form a connection interface that provides a removeable connection to a control device, such as a condom warming device, a personal lubricant warming device, or a combination condom and personal lubricant device, etc. The piercing element 561 and electrical connector 563 are disposed on or within the connection interface.

The piercing element 561 serves to secure the single chamber dispenser 560 to the PL container 530 by inserting the piercing element 561 into the discharge element 43 comprising the PL container 530. A protective seal (not shown) within the discharge element 43 is punctured upon securing the single chamber dispenser 560 to the PL container 530. The three grooved joinders 562 (connection interface) serve to adjoin the PL container/single chamber dispenser 510 to a warming device (control unit) comprising a power supply, electrical circuitry, other electrical components and heatable space. Once adjoined, the PL container 530 is positioned within the heatable space of the warming device while the single chamber dispenser 560 is positioned without the warming device. Also, as a result of adjoining the PL container/single chamber dispenser 510 to the warming device, the electrical circuitry connector 563 mates with a corresponding electrical connector within the warming device connecting the electrical circuitry within the dispenser to that of the warming device. The temperature probe 564 is wired to the electrical circuitry connector 563 and communicates with an electrical component of the adjoined warming device sending a signal indicating the temperature of lubricant being heated within the PL container 530. The indicated temperature may be shown to the user on a display comprising the warming device. Should the indicated temperature exceed the designed temperature, the power would modulate or shut off. The two actuator buttons 571, 576 are used to operate valves located within the body of the single chamber dispenser 560. By depressing the inlet actuator button 571 a valve is opened allowing lubricant to flow into a pre-delivery chamber (not shown). By depressing the outlet actuator button 576 a valve is opened allowing heated lubricant to flow out of the pre-delivery chamber (not shown) into the outlet cavity (not shown) exiting the dispenser through the spout.

The personal lubricant compartments 30, 130, 230 previously described in the first, second and third embodiments of the combination condom and personal lubricant container 10, 110, 210 and the first and second embodiments of the combination condom and personal lubricant kit 310, 410 may comprise the single chamber dispenser 560 as shown and described herein.

The PL container 530 comprises substantially the same elements as the personal lubricant compartments 30, 130, 230 comprising the combination condom and personal lubricant container 10, 110, 210 and kit 310, 410. The PL container 530 is not associated with a condom compartment 20, 220.

FIG. 18 shows the PL container 530 having a funnel-shaped enclosure 40. The perimeter of the top wall 531 is marked by two tapered side walls 34, a flat, perpendicular rear wall 535 and a discharge element 43. The PL container 530 comprises a sloping top wall 531, a horizontally positioned bottom wall 33, two tapered side walls 34 and the discharge element 43, the taper terminus for said walls. The PL container 510 comprises a rear wall 535 marking the broad end of the funnel 41. The rear wall 535 comprises a relatively flat, perpendicular surface. The rear wall 535 is joined to the top wall 531, bottom wall 33, and each side wall 34 at its top horizontal edge, bottom horizontal edge, and vertical edge, respectively. The top wall 531 slopes diagonally away from the top horizontal edge of the rear wall 535, the broad end of the funnel 41, toward the discharge element 43, the narrow end of the funnel 42, therefore; the broader end 41 is higher than the narrower end of the funnel 42. The downward slope facilitates the flow, via gravity, of personal lubricant and, concomitantly, the emptying of the PL container 530. A protective seal (not shown) within the discharge element 43 is punctured upon securing the single chamber dispenser 560 to the PL container 530.

The three side walls and bottom wall of the PL container 530 are constructed of a flexible, semi-rigid or rigid packaging material that is heatable and promotes the transfer of heat, such as aluminum. The top wall of the PL container 531 is constructed of a transparent or translucent insulating material allowing light to penetrate such that the amount of lubricant remaining within the PL container 530 may be determined with the aid of a bead 546, preferably with iridescent qualities, encapsulated within the PL container. The bead 546 floats atop the lubricant falling down toward the discharge element 43 as the lubricant is dispensed. Otherwise, the top wall 531 is constructed of a flexible, semi-rigid or rigid packaging material that is heatable and promotes the transfer of heat.

The PL container 530 may comprise an air release element 547 known in the art, including a valve, vent or pinholes, accommodating the flow of lubricant out of the container into the dispenser 560. FIG. 18 shows a valve secured within the top wall of the container 531. The valve comprises a tube-like structure open at each end. The valve's outlet has a grommet-like design; the upper lip sits atop the top wall 531 while the lower lip abuts the bottom side of the top wall. The remainder of the valve resides within the container 530 in the air space above the lubricant. With the aid of a closing element, if lubricant should enter the inlet to the valve and attempt to exit the PL container, the valve closes. Otherwise, the PL container 530 is hermetically sealed to form an airtight enclosure.

Figure 27A:
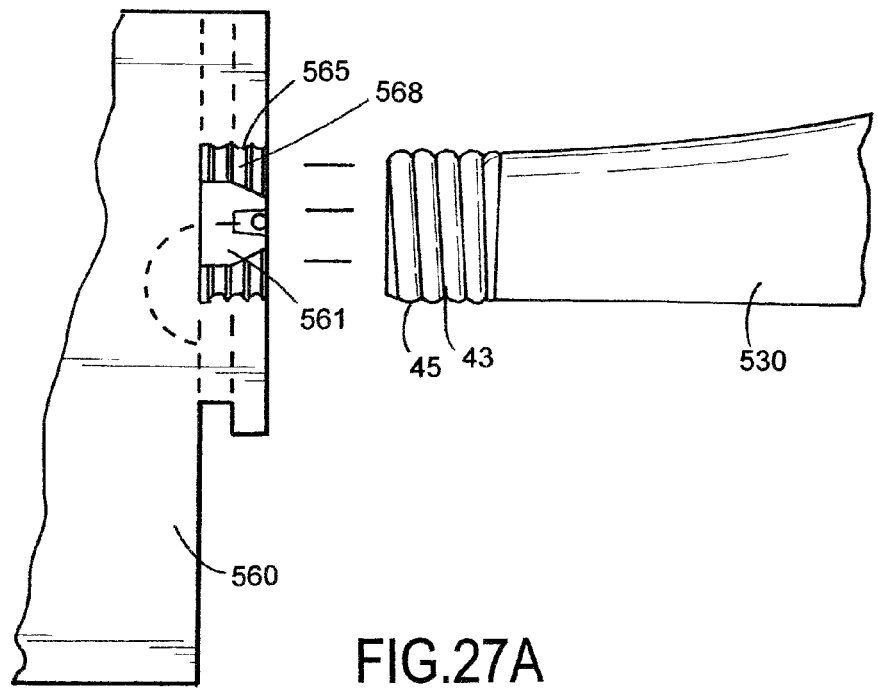
FIG. 27A shows a first alternative means of attaching a heatable single or dual chamber dispenser to a container.
Figure 27B:
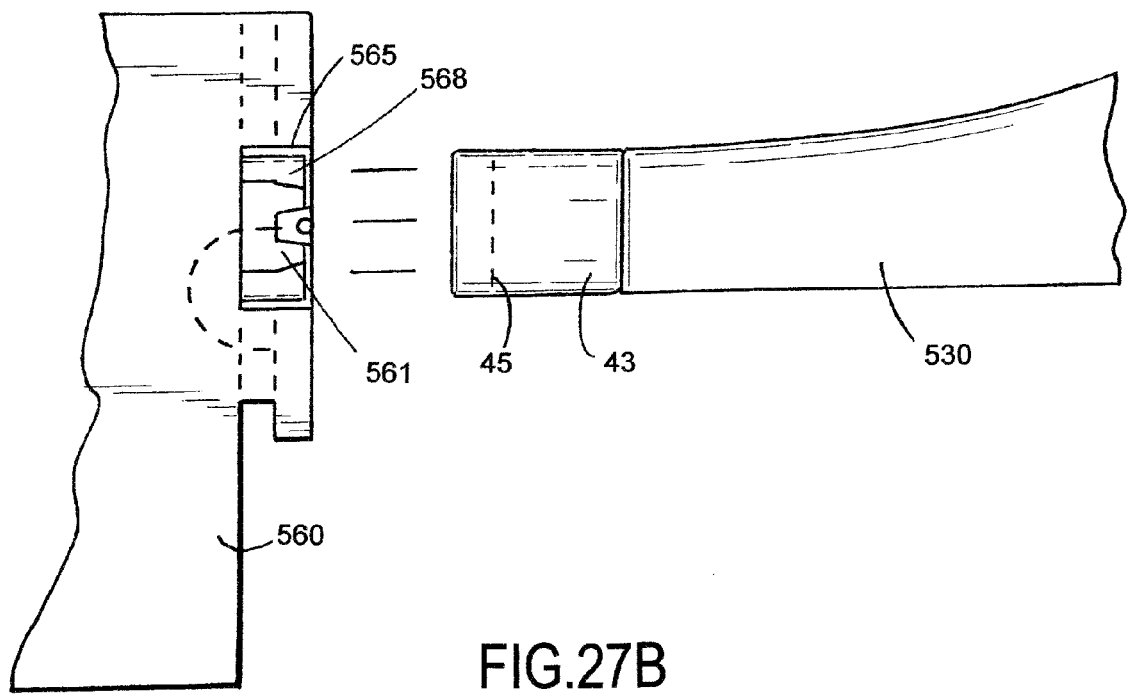
FIG. 27B shows a second alternative means of attaching a heatable single or dual chamber dispenser to a container.

Alternative securitization means may be employed. FIG. 27A pictures a discharge element 43 comprising the PL container 530 being screwed into the inlet cavity 565 comprising the dispenser 560. The exterior of the discharge element 43 and the interior of the inlet cavity 565 each comprise threads for this purpose. The piercing element 561 is positioned within the inlet cavity 565 but not protruding. Upon screwing the discharge element 43 into the inlet cavity 565, the protective seal 45 is punctured by the piercing element 561. FIG. 27B pictures a discharge element 43 comprising the PL container 530 inserted into the inlet cavity 565. The discharge element 43 and inlet cavity 565 are properly sized to create a seal with the aid of gasket 568 comprising the interior of the inlet cavity 565. The piercing element 561 is positioned within the inlet cavity 565 but not protruding. Upon inserting the discharge element 43 into the inlet cavity 565, the protective seal 45 is punctured by the piercing element 561. The interior of the inlet cavity 565 and the exterior of the discharge element 43 are sized to form a friction fit.

The personal lubricant compartments 30, 130, 230 previously described in the first, second and third embodiments of the combination condom and personal lubricant container 10, 110, 210 and the first and second embodiments of the combination condom and personal lubricant kit 310, 410 may comprise top walls constructed of a transparent or translucent insulating material, an encapsulated, floatable bead 546, preferably with iridescent qualities, an air release element 188 and alternative securitization means as shown and described herein.

FIG. 19 shows a top view of the single chamber dispenser 560. Located within the front wall of the single chamber dispenser is the piercing element 561 and electrical circuitry connector 563 both previously described. The temperature probe 564, previously described, is positioned within the hollow area of the piercing element 561 and wired to the electrical circuitry connector 563. Two vertically positioned grooved joinders 562, previously described, are positioned one on each side wall opposite one another nearest the front wall of the single chamber dispenser 560. The three grooved joinders 562 form a connection interface that provides a removeable connection to a control device, such as a condom warming device, a personal lubricant warming device, or a combination condom and personal lubricant device, etc. The piercing element 561 and electrical connector 563 are disposed on or within the connection interface.

Looking down at the top wall of the dual chamber dispenser 560, the shape of the pre-delivery chamber 570 is marked by dashed lines. The pre-delivery chamber 570 begins where the inlet actuator button 571 ends and ends where the outlet actuator button 576 begins. The course personal lubricant travels on its way out of the PL container and through the dispenser may be partially envisioned. Refer to the FIG. 20 description.

The one or more heating elements, such as heating element wire 592, marked by dashed lines, or other electrical wire is wound about the pre-delivery chamber 570 and is used to heat the chamber and its contents. The one or more heating elements 592 can also be disposed within the pre-delivery chamber 570 or integrated into one or more walls of the pre-delivery chamber 570. As shown in the drawing heating element wire is connected by wire leads 593 to the electrical circuitry connector 563. An insulating blanket 594, marked by dashed lines, encloses the heating element wire 592 and surrounds one or more portions of the pre-delivery chamber 570. A temperature probe 595 is positioned within the pre-delivery chamber 570 or operably connected to the pre-delivery chamber 570, and wired to the electrical circuitry connector 563. Refer to the FIG. 20 description.

FIG. 20 shows a cross-sectional view of the single chamber dispenser 560. The single chamber dispenser 560 is designed to accommodate both the channel through which personal lubricant travels within the body of the dispenser and the shape and location of the pre-delivery chamber 570. The channel through personal lubricant flows, via gravity, within the body of the single chamber dispenser 560 is stair-stepped. That is, the inlet cavity 565 is at a higher level than the pre-delivery chamber 570. The pre-delivery chamber 570 is at higher level than the outlet cavity 566. The outlet cavity 566 is at a higher level than the spout 590. The spout 590 can be an opening in the enclosure or protrude outward from the enclosure (as shown). The pre-delivery chamber 570 holds and heats a greater quantity of personal lubricant that could otherwise be held and heated within a channel substantially linear and uniform in shape.

Personal lubricant flows, via gravity, from the PL container into the single chamber dispenser 560. Initially, personal lubricant flows through the hollow piercing element 561 and into the inlet cavity 565. It resides within the inlet cavity 565 until an inlet valve 572 is opened by depressing an inlet actuator button 571 located on the top wall of the dispenser into an actuator button cavity 578 until the actuator button stop 579 is engaged. (External control of the inlet valve 572 avoids the unintended flow of personal lubricant from the PL container 530 into the pre-delivery chamber 570.) When the inlet valve 572 is opened, a disc 574, a part of the inlet valve 572, is pushed down away from an inverted seat 575 creating a trap door-like opening allowing personal lubricant to cascade down into the entrance to the pre-delivery chamber 570 filling the chamber. The personal lubricant resides within the pre-delivery chamber 570, until an outlet valve 577, opened by depressing the outlet actuator button 576 located on the top wall of the dispenser into an outlet actuator button cavity 578 until the outlet actuator button stop 579 is engaged. (External control of the outlet valve 577 avoids the unintended flow of personal lubricant from the pre-delivery chamber 570 into the outlet cavity 566.) When the outlet valve 577 is opened, a disc 574, a part of the outlet valve 577, is pushed down away from an inverted seat 575 allowing personal lubricant to cascade down into the outlet cavity 566 exiting the dispenser through the spout 590. The inlet and outlet valves 572, 577 are opened and closed with the aid of a spring 596 positioned about each stem 573.

FIG. 20 shows the outlet valve 577 to comprise a drip stopper 591 positioned at the end of the stem 573 blocking personal lubricant from exiting the single chamber dispenser 560 through the spout 590. The drip stopper 591 operates in tandem with the disc 574. When outlet actuator button 576 is depressed, the outlet valve 577 is opened releasing personal lubricant from the pre-delivery chamber 570 exiting the dispenser through the spout 590. When closed, the function of the drip stopper 591 is to stop drool. Other means may be used to prevent drool or no means at all.

Personal lubricant is heated within the dispenser's pre-delivery chamber 570. The pre-delivery chamber comprises a skeleton 567 made of a heatable material with heat transferring properties, such as stainless steel, copper, aluminum, etc. The shape of the chamber as shown is for illustrious purposes only. The chamber will be shaped to accommodate both volume and heating efficiency requirements. The chamber should hold about ten to fifteen grams of lubricant.

The pre-delivery chamber 570 is in thermal communication with a heating element. Heating element wire 592, marked by dashed lines, or other electrical wire is wound about the pre-delivery chamber 570 and is used to heat the chamber and its contents. The one or more heating elements 592 can also be disposed within the pre-delivery chamber 570 or integrated into one or more walls of the pre-delivery chamber 570. As shown in the drawing heating element wire is connected by wire leads 593 to the electrical circuitry connector 563. The electrical circuitry connector 563 is mated to a corresponding electrical connector within an adjoined warming device comprising a power supply, electrical circuitry and other electrical components. As a result, the heating assembly comprising the single chamber dispenser 560 is in electrical communication with components comprising the warming device. Power can then be supplied to the dispenser 560. An insulating blanket 594 encloses the heating element wire 592 and surrounds one or more portions of the pre-delivery chamber 570. A temperature probe 595 is positioned within the pre-delivery chamber 570 or operably connected to the pre-delivery chamber 570, and wired to the electrical circuitry connector 563. The temperature probe 595 communicates with an electrical component of the adjoined warming device sending a signal indicating the temperature of lubricant being heated within the pre-delivery chamber 570. The indicated temperature may be shown to the user on a display comprising the warming device. Should the indicated temperature exceed the designed temperature, the power would modulate or shut off. A temperature probe 564, previously described above, is positioned within the hollow area of the piercing element 561 and wired to the electrical circuitry connector 563.

Once the PL container/single chamber dispenser 510 is adjoined to a warming device, the single chamber dispenser 560 is positioned without the warming device while the attached container 530 is positioned within a heatable space of the warming device. Personal lubricant may be heated in situ while residing within the PL container 530 and subsequently fed into the dispenser 560 where the temperature is maintained prior to discharge. Unheated personal lubricant may also be fed into the dispenser 560 where the temperature is raised prior to discharge.

It is intended that the temperature of personal lubricant delivered to the user be at or about 100 to 110 degrees F. To achieve this result the temperature within the pre-delivery chamber may be somewhat higher, say, 110 to 120 degrees F. To insure that the temperature of the personal lubricant delivered is not substantially in excess of the desired range, power to the heating element may either discontinue or modulate when the temperature of the heating element reaches 110 to 120 degrees F. If the pre-delivery chamber contains ten grams, or one-third ounce, of personal lubricant, the contents should be heated to the desired temperature within two minutes using a rechargeable lithium battery capable of delivering approximately eight watts of power to the element. The length of time necessary to heat the personal lubricant to the desired temperature is primarily contingent on the source of power, i.e, AC/DC or DC, the type heating element and the temperature at which the element ceases to receive constant power and the configuration of pre-delivery chamber and heatable materials used to construct the pre-delivery chamber. Note that the discussion in this paragraph also applies to the other embodiments 610, 710.

Figure 21:
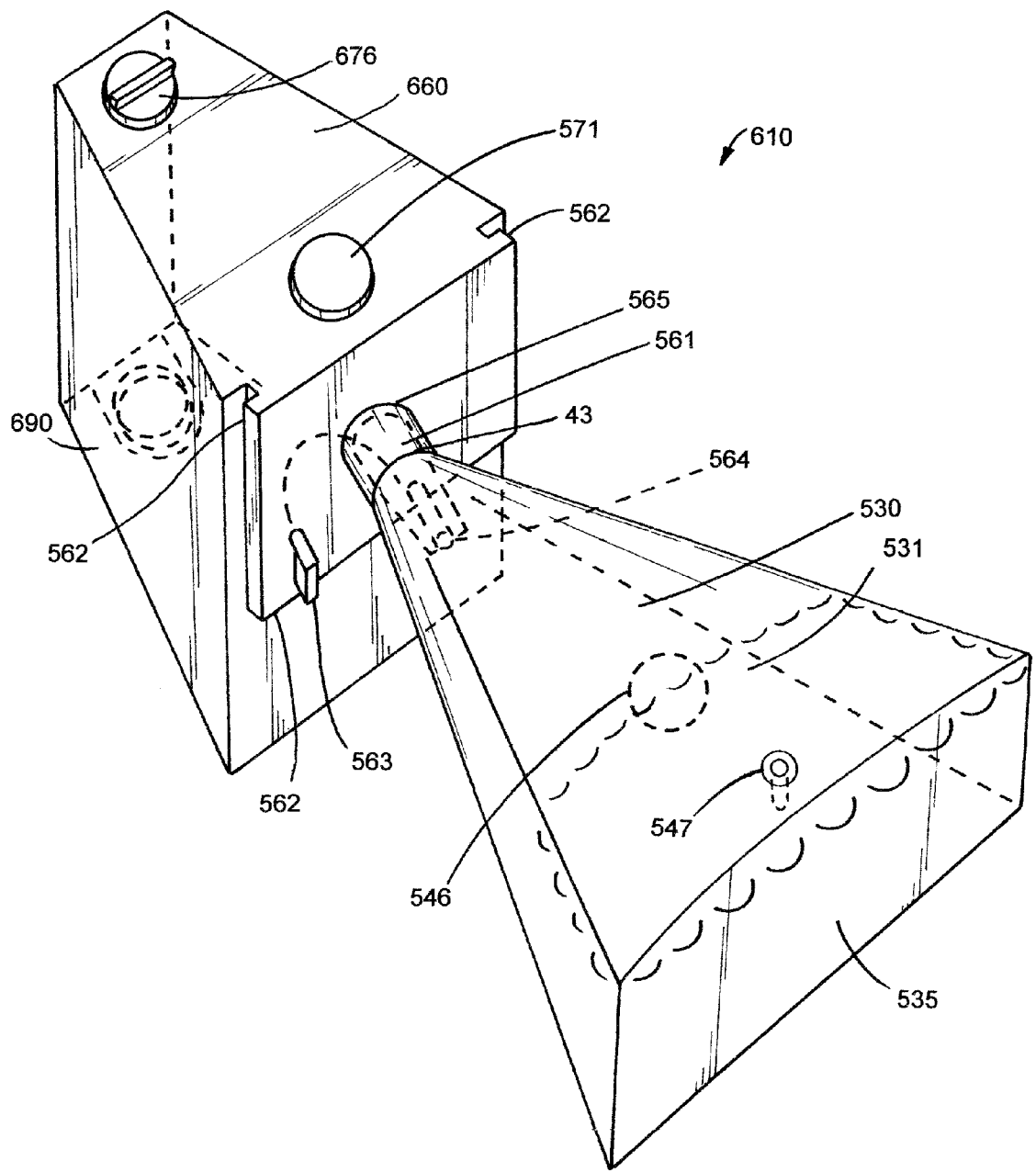
FIG. 21 shows a perspective view of a second embodiment of a personal lubricant container comprising a heatable dual chamber dispenser.
Figure 22:
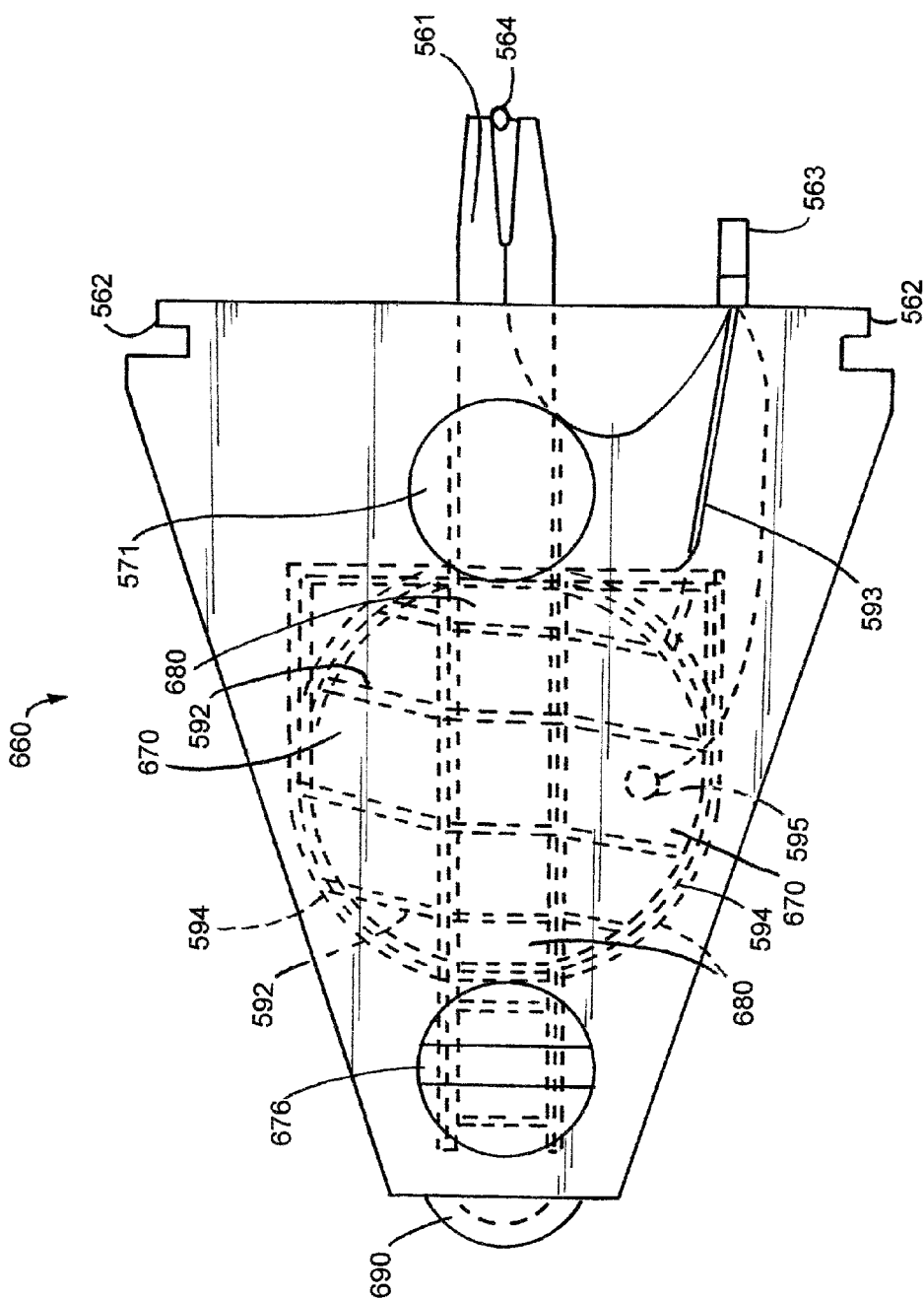
FIG. 22 shows a top view of a heatable dual chamber dispenser.
Figure 23:
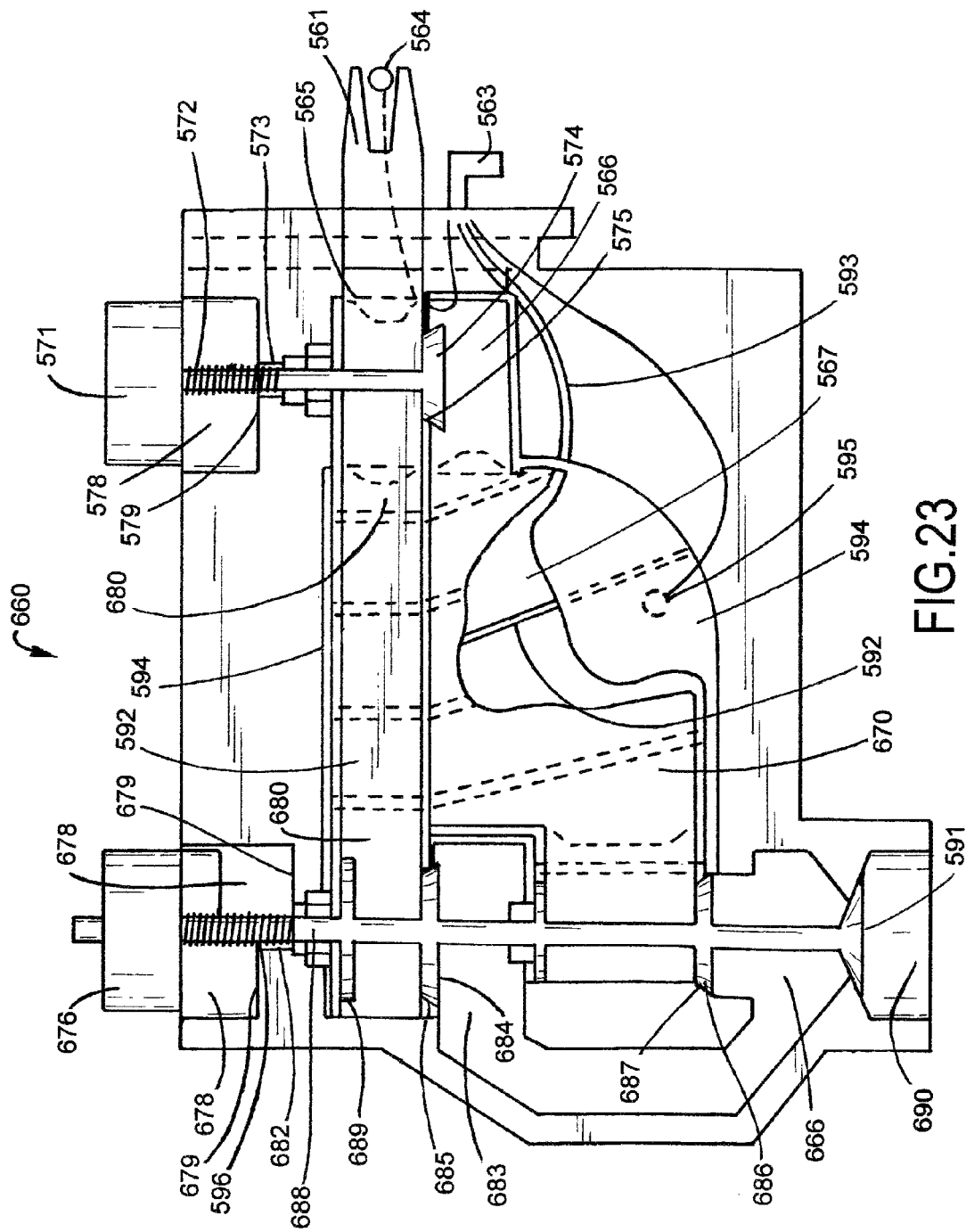
FIG. 23 shows a cross-sectional view of a heatable dual chamber dispenser.

Second Embodiment of a Personal Lubricant Container Comprising a Heatable Dual Chamber Dispenser—FIGS. 21, 22, 23

FIG. 21 shows a perspective view of a second embodiment of a personal lubricant container comprising a heatable dual chamber dispenser 610, hereinafter referred to as "PL container/dual chamber dispenser." The heatable dual chamber dispenser 660, hereinafter referred to as "dual chamber dispenser," is secured to the PL container 530 by means of inserting a piercing element 561 comprising the dual chamber dispenser 660 into a discharge element 43 comprising the PL container 530. Preferably, the dual chamber dispenser 660 is removably secured to the PL container 530 and re-usable. Alternatively, the dual chamber dispenser 660 is permanently secured to the PL container, and, accordingly, the PL container/dual chamber dispenser 610 is disposable.

The chassis or enclosure of the dual chamber dispenser 660 is principally constructed of a rigid material, such as molded plastic, comprising insulating or non-conducting properties. The dual chamber dispenser 660 comprises a front and rear wall, a top and bottom wall and two side walls. The dual chamber dispenser 660 comprises two heatable pre-delivery chambers within which a personal lubricant is heated. An upper pre-delivery chamber functions as a heated conduit principally maintaining the temperature of personal lubricant received from and previously heated within the container 530. A lower pre-delivery chamber functions as a heated conduit raising the temperature of personal lubricant received from and previously unheated within the container 530.

FIG. 21 shows the dual chamber dispenser 660 comprising a piercing element 561 protruding from the inlet cavity 565 located within the front wall, a temperature probe 564 located within the hollow piercing element 561, three grooved joinders 562 two vertically positioned on the side walls nearest the front wall and one horizontally positioned below the piercing element 561 on the front wall, an electrical circuitry connector 563 located on the front wall, two actuator buttons 571, 676 located on the top wall and a dual channel spout 690, marked by dashed lines, located on the bottom and rear walls. The three grooved joinders 562 form a connection interface that provides a removeable connection to a control device, such as a condom warming device, a personal lubricant warming device, or a combination condom and personal lubricant device, etc. The piercing element 561 and electrical connector 563 are disposed on or within the connection interface.

The piercing element 561, the temperature probe 571, the three grooved joinders 562, the electrical circuitry connector 563 and the inlet actuator button 571 are elements comprising the single chamber dispenser 560 and perform the same functions when comprising elements of the dual chamber dispenser 660. Refer to the description of FIG. 18 for a discussion of the piercing element 561.

Neither the dual chamber outlet actuator button 676 nor the dual channel spout 690 are elements of the single chamber dispenser. The top of the dual chamber outlet actuator button 676 comprises a raised element that may be turned rotating an underlying dual outlet valve controlling whether lubricant flows out of the upper pre-delivery chamber, hereinafter referred as "upper chamber," or lower pre-delivery chamber, hereinafter referred as "lower chamber." For a further description of these elements and the functions performed refer to FIG. 23.

The personal lubricant compartments 30, 130, 230 previously described in the first, second and third embodiments of the combination condom and personal lubricant container 10, 110, 210 and the first and second embodiments of the combination condom and personal lubricant kit 310, 410 may comprise the dual chamber dispenser 660 as shown and described herein.

FIG. 21 shows the PL container 530 to comprise substantially the same elements as the personal lubricant compartments 30, 130, 230 comprising the combination condom and personal lubricant container 10, 110, 210 and kit 310, 410. The PL container 530 is not associated with a condom compartment 20, 220.

The PL container 530 comprising the PL container/dual chamber dispenser 610 comprises the same elements and performs the same functions as the PL container 530 comprising the PL container/single chamber dispenser 510 and comprises a top wall 531 constructed of either a transparent or translucent insulating material or a flexible, semi-rigid or rigid heatable packaging material and may comprise an encapsulated, floatable bead 546, preferably with iridescent qualities, an air release element 547 and alternative securitization means as shown and described herein. Refer to the previous description of the PL container 530 in reference to FIGS. 18 and 27A.

FIG. 22 shows a top view of the dual chamber dispenser 660. The drawing shows the dual chamber dispenser 660 comprising the piercing element 561, the temperature probe 564 within the piercing element, two vertically positioned grooved joinders 562, the electrical circuitry connector 563, two actuator buttons 571, 676 and the dual channel spout 690. The piercing element 561, the temperature probe 564, the two vertically positioned grooved joinders 562, the electrical circuitry connector 563 and the inlet actuator button 571 are elements comprising the single chamber dispenser 560 and perform the same functions when comprising elements of the dual chamber dispenser 660. Refer to the description of FIG. 18 for a discussion of the piercing element 561. The three grooved joinders 562 form a connection interface that provides a removeable connection to a control device, such as a condom warming device, a personal lubricant warming device, or a combination condom and personal lubricant device, etc. The piercing element 561 and electrical connector 563 are disposed on or within the connection interface.

Neither the dual chamber outlet actuator button 676 nor the dual channel spout 690 are elements of the single chamber dispenser 560. For a description of these elements and the functions performed refer to FIG. 23.

Looking down at the top wall of the dual chamber dispenser 660, the shapes of the lower and upper chambers 670, 680 are marked by dashed lines. The upper chamber 680 begins where the inlet actuator button 571 ends and ends where the dual chamber outlet actuator button 676 ends. The lower chamber 670 begins where the inlet actuator button 571 ends and ends where the dual chamber outlet actuator button 676 begins. The course personal lubricant travels on its way out of the PL container and through the dispenser may be partially envisioned. Refer to the FIG. 23 description.

The one or more heating elements, such as heating element wire 592, marked by dashed lines, or other electrical wire is wound about the lower and upper pre-delivery chambers 670, 680 and is used to heat the chambers and their contents. The one or more heating elements 592 can also be disposed within the lower and upper pre-delivery chambers 670, 680 or integrated into one or more walls of the lower and upper pre-delivery chambers 670, 680. As shown in the drawing heating element wire is connected by wire leads 593 to the electrical circuitry connector 563. An insulating blanket 594, marked by dashed lines, encloses the heating element wire 592 and surrounds one or more portions of the lower and upper chambers 670, 680. A temperature probe 595 is positioned within the lower chamber 670 or operably connected to the lower chamber 670, and wired to the electrical circuitry connector 563. Refer to the FIG. 23 description.

FIG. 23 shows a cross-sectional view of the dual chamber dispenser 660. It is designed to accommodate two channels, the first comprising the upper chamber 680 and the second comprising the lower chamber 670, through which personal lubricant flows, via gravity, within the body of the dispenser. Both channels are stair-stepped. Regarding the first channel, the upper chamber 680, running horizontal, is at a higher level than the upper outlet cavity 683. The upper chamber outlet cavity 683 is at a higher level than the dual channel spout 690. The spout 690 can be an opening in the enclosure or protrude outward from the enclosure (as shown). Regarding the second channel, an inlet cavity 565 is at a higher level than the lower chamber 670. The lower chamber 670 is at a higher level than the lower chamber outlet cavity 666. The lower chamber outlet cavity 666 is at a higher level than the dual channel spout 690.

Regarding the movement of personal lubricant from the PL container into the dual chamber dispenser 660, it initially flows through the hollow piercing element 561 into the upper chamber 680 without stopping in the inlet cavity 565 as there is no wall separating the inlet cavity 565 from the upper chamber 680. The lubricant resides in the upper chamber 680 until 1) the dual chamber outlet actuator button 676, properly positioned, is depressed releasing lubricant into the upper chamber outlet cavity 683 exiting the dispenser through the dual channel spout 690, 2) the inlet actuator button 571 is depressed releasing lubricant into the lower chamber 670, or 3) the lubricant flows back into the PL container 530 as there is no impediment to its return.

The upper chamber 680 is a part of the first channel comprising the dual chamber dispenser 660 and functions as a heated conduit maintaining the temperature of previously heated personal lubricant received from the PL container 530. Personal lubricant is released from the upper chamber 680 into the upper chamber outlet cavity 683 by depressing dual chamber outlet actuator button 676. However, personal lubricant within the upper chamber 680 is released only if the actuator button 676 is properly positioned. The actuator button 676 and the dual chamber outlet valve 682, controlled by the former, are designed so that personal lubricant within upper chamber 680 is not discharged at the same time as personal lubricant from the lower chamber 670 and vice versa. To achieve this result, the dual chamber outlet actuator button 676 and dual outlet valve 682 comprise unique elements.

The dual chamber outlet actuator button 676 comprises a raised element on its top side that is used to turn the actuator button 676 to the right or left rotating the dual outlet valve 682. The actuator button 676 comprises an element on its bottom side that extends downward from the base of the button. The base of the button is level with the top wall of the dual chamber dispenser 660 while the bottom side element lies beneath the top wall within the dual outlet actuator button cavity 678. When the actuator button 676 is depressed, it is forced further into the cavity 678 stopping when the bottom side element engages a dual outlet actuator button stop 679. The actuator button stop 679 comprises an upper and lower ridge within the cavity 678. Which ridge, the upper or lower, the bottom side element first engages is dependent upon whether the actuator button 676 was turned to the right or left. To open the valve, releasing lubricant within the upper chamber 680 into upper chamber outlet cavity 683, the actuator button 676 must be turned so that the bottom side element first engages the upper ridge of the actuator button stop 679.

The dual outlet valve 682 comprises an elongated stem 688 that is attached to the bottom of the dual chamber outlet actuator button 676 extending down through the upper chamber 680, the upper chamber outlet cavity 683, the lower chamber 670 and the lower chamber outlet cavity 666 and into the dual channel spout 690. The elongated stem 688 comprises a flow inhibitor 689, an upper chamber disc 684 positioned within an inverted upper seat 685 (valve closed), a lower chamber disc 686 positioned within an inverted lower seat 687 (valve closed) and a drip stopper 591. The drip stopper 591 operates in tandem with other elements comprising the stem 688. When actuator button 676 is depressed, the dual outlet valve 682 is opened. In tandem, the drip stopper 591 moves away from an opening leading into the dual channel spout 690 allowing personal lubricant to exit the dispenser through the spout 690. When the dual outlet valve 682 is closed, the drip stopper 591 impedes any dripping or drool. The dual outlet valve 682 is opened and closed with the aid of a spring 596 positioned about the stem 688.

Personal lubricant within the upper chamber 680 is discharged if bottom side element comprising the dual outlet actuator button 676 first engages the upper ridge of the actuator button stop 679. The upper chamber disc 684 moves away from the inverted upper chamber seat 685 but not to the floor of the upper chamber outlet cavity 683 opening the valve. The flow inhibitor 689 moves away from the ceiling of the upper chamber 680 but not to the floor of the chamber 680 keeping the valve open.

Personal lubricant within the upper chamber 680 is not discharged if bottom side element comprising the dual outlet actuator button 676 first engages the lower ridge of the actuator button stop 679. Although the upper disc 684 moves away from the upper seat 685 to the floor of the upper chamber outlet cavity 683 opening the valve, the flow inhibitor 689 simultaneously moves away from the ceiling of the upper chamber 680 to the floor of the chamber 680 closing the valve.

The lower chamber 670 is a part of the second channel comprising the dual chamber dispenser 660 and functions as a heated conduit raising the temperature of previously unheated personal lubricant received from the attached container. The path taken by personal lubricant through the second channel is as follows. Lubricant flows through the hollow piercing element 561 into the inlet cavity 565 and the upper chamber 680 where it resides until an inlet valve 572 is opened by depressing the inlet actuator button 571 forcing the button into an inlet actuator button cavity 578 stopping when the inlet actuator button stop 579 is engaged. (External control of the inlet valve 572 avoids the unintended flow of lubricant from the attached container into the lower chamber 670.) When the inlet valve 572 is opened, a disc 574 comprising a stem 573, a part of the inlet valve 572, is pushed down away from an inverted seat 575 creating a trap door-like opening allowing personal lubricant to cascade down into the entrance to the lower chamber 670 filling the chamber.

Personal lubricant resides within the lower chamber 670 until the dual chamber outlet valve 682 is opened by depressing the dual chamber outlet actuator button 676 into the lower chamber outlet cavity 666 stopping when the dual chamber actuator button stop 679 is engaged. However, personal lubricant is released from the lower chamber 670 into the lower chamber outlet cavity 666 only if the actuator button 676 is properly positioned.

As previously described, the dual chamber outlet actuator button 676 comprises an element on its top side that is used to turn the button 676 to the right or left rotating the dual outlet valve 682. The actuator button 676 also comprises an element on its bottom side that extends downward from the base of the button. To open the valve, releasing lubricant from the lower chamber 670 into lower chamber outlet cavity 666, the actuator button 676 must be turned so that the bottom side element first engages the lower ridge of the actuator button stop 679. As a result of properly positioning the actuator button 676, the lower chamber disc 686 moves away from the inverted lower chamber seat 687 opening the valve and personal lubricant is released from the lower chamber 670 into the lower chamber outlet cavity 666 exiting the dispenser through the dual channel spout 690.

Personal lubricant within the lower chamber 670 is not discharged if bottom side element comprising the actuator button 676 first engages the upper ridge of the actuator button stop 679. Although the lower chamber disc 686 moves away from the lower chamber seat 687, the distance traveled downward is insufficient to clear the walls of the lower outlet cavity 666 keeping the valve closed. (Keep in mind any lubricant released would be heated.)

The lower and upper chambers 670, 680 comprise a skeleton 567 made of a heatable material with heat transferring properties, such as stainless steel, copper, aluminum, etc. The shapes of the chambers as shown are for illustrious purposes only. The lower chamber 670 will be shaped to accommodate both volume and heating efficiency requirements. The chamber should hold ten to fifteen grams of lubricant.

The lower and upper chambers 670, 680 are in thermal communication with one or more heating elements. The one or more heating elements, such as heating element wire 592, marked by dashed lines, or other electrical wire is wound about the lower and upper chambers 670, 680 and used to heat the chambers and their contents. The one or more heating elements 592 can also be disposed within the lower and upper pre-delivery chambers 670, 680 or integrated into one or more walls of the lower and upper pre-delivery chambers 670, 680. As shown in the drawing heating element wire is connected by wire leads 593 to the electrical circuitry connector 563. The electrical circuitry connector 563 is mated to a corresponding electrical connector within an adjoined warming device comprising a power supply, electrical circuitry and other electrical components. As a result, the heating assembly comprising the dual chamber dispenser 660 is in electrical communication with components comprising the warming device. Power can then be supplied to the dispenser 660. An insulating blanket 594 encloses the heating element wire 592 and surrounds one or more portions of the lower and upper chambers 670, 680. A temperature probe 595 is positioned within the lower chamber 670 or operably connected to the lower chamber 670, and wired to the electrical circuitry connector 563. (A temperature probe may be positioned within the upper chamber.) As a result, the temperature probe 595 communicates with an electrical component of the adjoined warming device sending a signal indicating the temperature of lubricant being heated within the lower chamber 670. The indicated temperature may be shown to the user on a display comprising the warming device. Should the indicated temperature exceed the designed temperature, the power would modulate or shut off. A temperature probe 564, previously described, is positioned within the hollow area of the piercing element 561 and wired to the electrical circuitry connector 563.

Once the PL container/dual chamber dispenser 610 is adjoined to a warming device, the dual chamber dispenser 660 is positioned without the warming device while the attached container 530 is positioned within a heatable space of the warming device. Personal lubricant may be heated in situ while residing within the PL container 530 and subsequently fed into the dispenser 660 where the temperature is maintained prior to discharge. Unheated personal lubricant may also be fed into the dispenser 660 where the temperature is raised prior to discharge.

Figure 28:
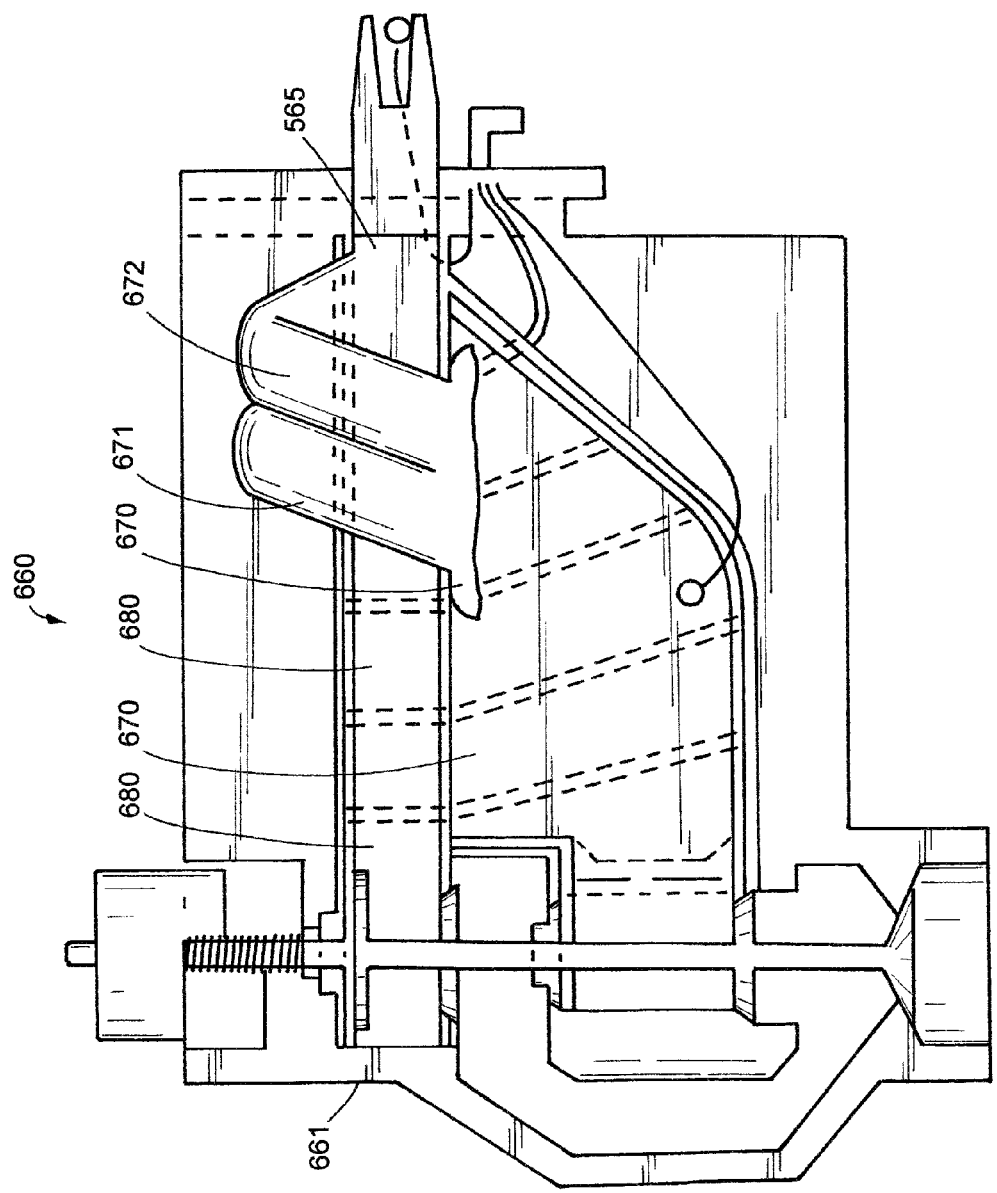
FIG. 28 shows a cross-sectional view of an alternative means used to fill the lower pre-delivery chamber with personal lubricant.

FIG. 28 shows a cross-sectional view of the dual chamber dispenser 660 depicting an alternative means used to fill the lower chamber 670 with personal lubricant. Personal lubricant entering the dispenser 660 from the PL container 530 fills the lower chamber 670 without need of an inlet actuator button or inlet valve. Lubricant flows from the upper chamber 680 into the lower chamber 670 via a product duct 671 connecting the topside of the upper chamber 680 to the topside of the lower chamber 670. As a result of feeding product into the lower chamber 670 from the upper chamber 680, air within the lower chamber is displaced. The displaced air is forced through an air duct 672 connecting the topside of the lower chamber 670 to the topside of the upper chamber 680. The air duct 672 abuts the product duct 671 and is located nearer the inlet cavity 565. The lower chamber 670 is filled with lubricant in the following manner. The dual chamber dispenser 660 is positioned with the rear wall 661 facing down. Lubricant flows from PL container into the inlet cavity 565 and fills the upper chamber 680. When the column of personal lubricant reaches the inlet to the product duct 671, the product will flow into the product duct 671 and fill the lower chamber 670. Air within the lower chamber 670 is displaced and forced through the air duct 672. The air flows or bubbles out of the dispenser 660 via the inlet cavity 565 and into the PL container comprising an air release element. The product duct 671 and air duct 672 are made of material comprising heatable properties. The dual chamber pump dispenser (see below) may comprise the air duct 672 (but not product duct) as a means of allowing displaced air to escape the lower chamber when filling the chamber with flowable product. The displaced air flows or bubbles out of the dispenser via the inlet cavity into the container comprising an air release element.

Figure 24:
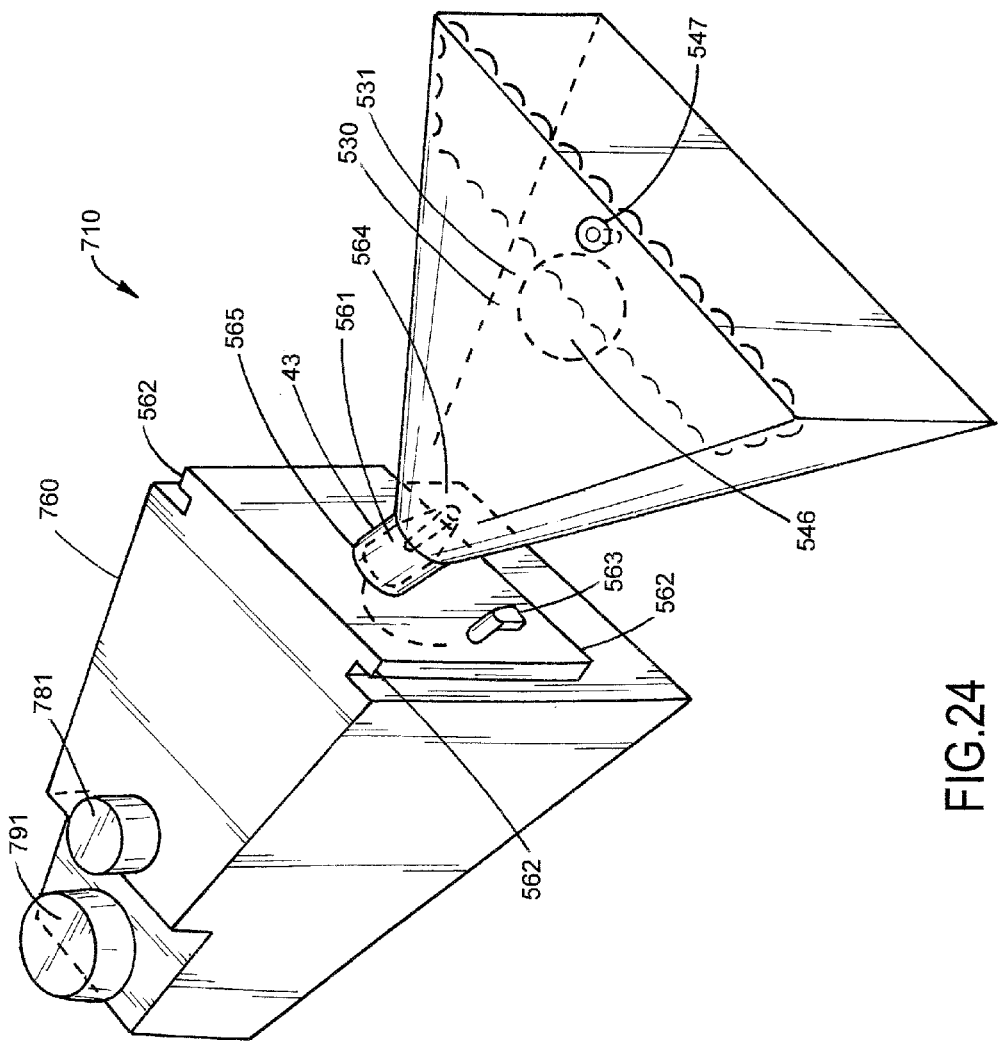
FIG. 24 shows a perspective view of a third embodiment of a personal lubricant container comprising a heatable dual chamber pump dispenser.
Figure 25:
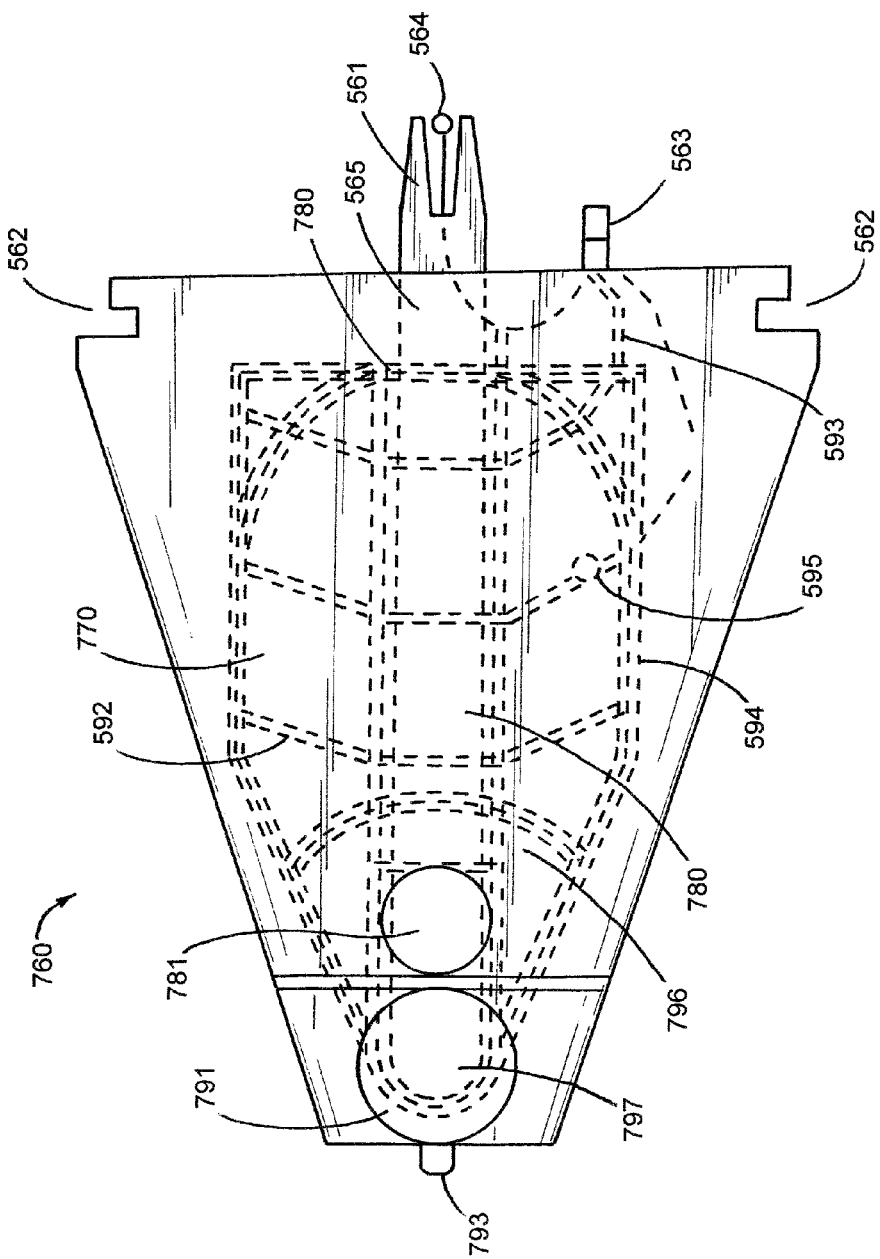
FIG. 25 shows a top view a heatable dual chamber pump dispenser.

Third Embodiment of a Heatable Dual Pre-Delivery Chamber Dispenser—FIGS. 24, 25, 26

FIG. 24 shows a perspective view of a third embodiment of the PL container comprising a heatable dual chamber pre-delivery dispenser with pump 710, hereinafter referred to as "PL container/dual chamber pump dispenser." The heatable dual chamber pre-delivery dispenser with pump 760, hereinafter referred to as "dual chamber pump dispenser," is secured to the PL container 530 by means of inserting a piercing element 561 comprising the dual chamber pump dispenser 760 into a discharge element 43 comprising the PL container 530. Preferably, the dual chamber dispenser 760 is removably secured to the PL container 530 and re-usable.

Alternatively, the dual chamber dispenser 760 is permanently secured to the PL container, and, accordingly, the PL container/dual chamber pump dispenser 710 is disposable.

The chassis or enclosure of the dual chamber pump dispenser 760 is principally constructed of a rigid material, such as molded plastic, comprising insulating or non-conducting properties. The dual chamber pump dispenser 760 comprises a front and rear wall, a top and bottom wall and two side walls. The dual chamber pump dispenser 760 comprises two heatable pre-delivery chambers and two heatable cavities within which personal lubricant is heated. An upper pre-delivery chamber functions as a heated conduit principally maintaining the temperature of personal lubricant received and previously heated within the PL container 530. A lower pre-delivery chamber functions as a heated conduit principally raising the temperature of personal lubricant received and previously unheated within the PL container 530. A dual chamber discharge cavity and dual chamber outlet cavity function as heated conduits maintaining and raising the temperature of personal lubricant received.

Various elements comprising the dual chamber pump dispenser 760 are pictured in FIG. 24 including a piercing element 561 protruding from an inlet cavity 565 located within the front wall, a temperature probe 564 located within the piercing element 561, three grooved joinders 562 two vertically positioned on the side walls nearest the front wall and one positioned below the piercing element on the front wall, an electrical circuitry connector 563 located on the front wall, an upper chamber actuator button 781 located on the top wall and an actuator pump button 791 located on the top wall. The three grooved joinders 562 form a connection interface that provides a removeable connection to a control device, such as a condom warming device, a personal lubricant warming device, or a combination condom and personal lubricant device, etc. The piercing element 561 and electrical connector 563 are disposed on or within the connection interface.

The piercing element 561 serves to attach the PL container 530 to the dual chamber pump dispenser 760 by inserting the piercing element 561 comprising the dispenser into a discharge element 43 comprising the PL container. The three grooved joinders 562 (connection interface) serve to adjoin the PL container/dual chamber pump dispenser 710 to a warming device (control unit) comprising a power supply, electrical circuitry, other electrical components and heatable space. Once adjoined, the dispenser 760 is positioned without the warming device while the attached PL container 530 is positioned within the heatable space of the warming device.

Also, as a result of adjoining the dispenser 760 to the warming device, the electrical circuitry connector 563 mates with a corresponding electrical connector within the warming device connecting the electrical circuitry within the dispenser to that of the warming device. Power can then be supplied to the dispenser 760. Lubricant flowing from the container into the dual chamber pump dispenser 760 is heated either by raising or maintaining its temperature. The temperature probe 564 is wired to the electrical circuitry connector 563 and communicates with an electrical component of the adjoined warming device sending a signal indicating the temperature of the personal lubricant being heated within the container. The indicated temperature may be shown to the user on a display comprising the warming device. Should the indicated temperature exceed the designed temperature, the power would modulate or shut off. The upper chamber actuator button 781 is used to operate a valve located within the body of the dual chamber pump dispenser 760. By depressing the actuator button 781 a valve is opened allowing lubricant to flow out of the upper pre-delivery chamber. The actuator pump button 791 is used to operate a pump which siphons personal lubricant out of dual chamber outlet cavity (not shown) and discharges the lubricant through the spout.

The PL container 530 comprising the PL container/dual chamber pump dispenser 710 comprises the same elements and performs the same functions as the PL container 530 comprising the PL container/single chamber dispenser 510 and comprises a top wall 531 constructed of either a transparent or translucent insulating material or a flexible, semi-rigid or rigid heatable packaging material and may comprise an encapsulated, floatable bead 546, preferably with iridescent qualities, an air release element 547 and alternative securitization means as shown and described herein. Refer to the previous description of the PL container 530 in reference to FIGS. 18 and 27A.

FIG. 25 shows a top view of the dual chamber pump dispenser 760. The drawing shows the dual chamber pump dispenser 760 comprising the piercing element 561, the temperature probe 564, two grooved joinders 562, the electrical circuitry connector 563, the upper chamber actuator button 781, the actuator pump button 791 and the spout 793. The piercing element 561, the temperature probe 564, the two grooved joinders 562 and the electrical circuitry connector 563 are elements comprising the PL container/single chamber dispenser 510 and perform the same functions when comprising elements of the PL container/dual chamber pump dispenser 710. Refer to the description of these elements in reference to FIG. 18. For a more extensive description of the upper chamber actuator button 781, the actuator pump button 791 and the spout 793 refer to the description under FIG. 26.

Looking down at the top wall of the dual chamber pump dispenser 760, the shapes of the upper pre-delivery chamber 780, hereinafter referred to as "upper chamber," lower pre-delivery chamber 770, hereinafter referred to as "lower chamber," dual chamber outlet cavity 796 and dual chamber discharge cavity 797 are marked in dashed lines. The upper chamber 780 begins where the inlet cavity 565 ends and ends where upper chamber actuator button 781 ends. The lower chamber 770 begins where the inlet cavity 565 ends and ends where the upper chamber actuator button 781 begins. The dual chamber outlet cavity 796 begins with the curved dashed lines preceding the upper chamber actuator button 781 and ends under the actuator pump button 791. The dual chamber discharge cavity 797 begins and ends under the actuator pump button 791. The course personal lubricant travels through the dispenser may be partially envisioned. Refer to the FIG. 26 description.

The one or more heating elements, such as heating element wire 592, marked by dashed lines, or other electrical wire is wound about the lower chamber 770, upper chamber 780, dual chamber outlet cavity 796 and dual chamber discharge cavity 797 and is used to heat the chambers and cavities and their contents. The one or more heating elements 592 can also be disposed within the lower chamber 770, upper chamber 780, dual chamber outlet cavity 796 and dual chamber discharge cavity 797 or integrated into one or more walls of the lower chamber 770, upper chamber 780, dual chamber outlet cavity 796 and dual chamber discharge cavity 797. As shown in the drawing heating element wire is connected by wire leads 593 to the electrical circuitry connector 563. An insulating blanket 594, marked by dashed lines, encloses the heating element wire 592 and surrounds one or more portions of the lower chamber 770, upper chamber 780, dual chamber outlet cavity 796 and dual chamber discharge cavity 797. Temperature probes 595 may be positioned within the lower and upper chambers 770, 780 or operably connected to the lower and upper chambers 770, 780, and wired to the electrical circuitry connector 563. FIG. 25 shows a temperature probe positioned within the lower chamber 770. Refer to the description relating to FIG. 26 for an explanation of the function of the temperature probe 595.

FIG. 26 shows a cross-sectional view of the dual chamber pump dispenser 760. It is designed to accommodate two channels, the first comprising the upper chamber 780 and the second comprising the lower chamber 770, into and through which personal lubricant flows within the body of the dispenser. The upper chamber 780 principally functions as a heated conduit maintaining the temperature of previously heated personal lubricant received from the PL container. The lower chamber 770 principally functions as a heated conduit raising the temperature of previously unheated personal lubricant received from the PL container.

The first channel comprises 1) the inlet cavity 565, 2) the upper chamber 780 in the shape of an inverted L comprising a horizontal shaft running from the inlet cavity 565 and a vertical shaft extending downward, 3) a dual chamber outlet cavity 796 positioned below the vertical shaft of the upper chamber 780, 4) a dual chamber discharge cavity 797 comprising a vertical shaft extending up from the dual chamber outlet cavity 796 and 5) a spout 793.

The second channel comprises 1) the lower chamber 770 positioned below and abutting the horizontal and vertical shafts of the upper chamber 780, 2) the dual chamber outlet cavity 796 positioned below the lower chamber 770 as well as the upper chamber 780, 3) the dual chamber discharge cavity 797 comprising a vertical shaft extending up from the dual chamber outlet cavity 796 and 4) the spout 793.

Regarding the movement of lubricant out of the PL container and through the two channels, it initially flows through the hollow piercing element 561 into the upper chamber 780 without stopping in the inlet cavity 565 as there is no wall separating the inlet cavity 565 from the upper chamber 780. The personal lubricant resides horizontally and vertically within the upper chamber 780. It resides within the upper chamber 780 until upper chamber actuator button 781 is depressed releasing product into the dual chamber outlet cavity 796. Once the dual chamber outlet cavity 796 is filled, additional lubricant released from the upper chamber 780 is forced into the lower chamber 770 and dual chamber discharge cavity 797. When the lower chamber 770 and the dual chamber discharge cavity 797 are filled to capacity, lubricant from PL container will discontinue flowing. The highest level achieved by lubricant migrating into either vessel 770, 797 should be less than the highest level of the horizontal shaft of the upper chamber 780. The dual chamber pump dispenser 760 may comprise an air duct as a means of allowing displaced air to escape the lower chamber 770 when filling the chamber with flowable product. The displaced air flows or bubbles out of the dispenser 760 via the inlet cavity 565 into the container comprising an air release element. Refer to the discussion relating to FIG. 28 for a description of the air duct 672 shown in FIG. 28.

As previously described, personal lubricant resides in the upper chamber 780 until the upper chamber actuator button 781 is depressed releasing lubricant into the dual chamber outlet cavity 796. When the upper chamber actuator button 781 is depressed, it is forced down into the actuator button cavity 783 stopping when it engages the actuator button stop 784. The actuator button 781 controls the upper chamber outlet valve 782. The upper chamber outlet valve 782 comprises a stem 785 that is attached to the bottom of the actuator button 781 and extends down through the vertical shaft of the upper chamber 780. The stem 785 comprises an upper chamber disc 786 positioned within an inverted upper chamber seat 787 (valve closed). Depressing the actuator button 781, opens the valve. The disc 786 moves down away from the seat 787 when the valve is opened.

Personal lubricant released into the dual chamber outlet cavity 796 from the upper chamber 780 may be heated or unheated. If the personal lubricant was previously heated within the PL container, its temperature will be maintained while residing within the upper chamber 780, lower chamber 770, dual chamber outlet cavity 796 and dual chamber discharge cavity 797. If the personal lubricant was unheated, its temperature will be raised while residing within the lower chamber 770, dual chamber outlet cavity 796 and dual chamber discharge cavity 797. Heated personal lubricant resides within the lower chamber 770, dual chamber outlet cavity 796 and dual chamber discharge cavity 797 until it is drawn through the dual chamber discharge cavity 797 by depressing the pump actuator button 791 activating a pumping mechanism, shown in FIG. 26 to be a lotion pump 790. The pumping mechanism, positioned at the top of the dual chamber discharge cavity 797, discharges product through the spout 793. The spout 793 can be an opening in the enclosure (as shown) or protrude outward from the enclosure. The pump comprises a dip tube 792. But for the tail-end of personal lubricant fed into the dispenser 760 from the container, the dip tube 792 may be unnecessary given the upward migration of product out of the dual chamber outlet cavity 796 into the dual chamber discharge cavity 797. The lotion pump 790 may be removable to facilitate the cleaning of the pump and/or dispenser 760. Other types of pumps may be employed.

The lower chamber 770, upper chamber 780, dual chamber outlet cavity 796 and dual chamber discharge cavity 797 comprise a skeleton 567 made of a heatable material with heat transferring properties, such as stainless steel, copper, aluminum, etc. The shapes of the chambers as shown are for illustrious purposes only. The lower chamber 770 will be shaped to accommodate both volume and heating efficiency requirements. The chamber should hold ten to fifteen grams of lubricant.

The one or more heating elements, such as heating element wire 592, marked by dashed lines, or other electrical wire is wound about the upper chamber 780, lower chamber 770, dual chamber outlet cavity 796 and dual chamber discharge cavity 797 and used to heat the chambers 770, 780 and cavities 796, 797 and their contents. The one or more heating elements 592 can also be disposed within the upper chamber 780, lower chamber 770, dual chamber outlet cavity 796 and dual chamber discharge cavity 797 or integrated into one or more walls of the upper chamber 780, lower chamber 770, dual chamber outlet cavity 796 and dual chamber discharge cavity 797. As shown in the drawing heating element wire is connected by wire leads 593 to the electrical circuitry connector 563. The electrical circuitry connector 563 is mated to a corresponding electrical connector within an adjoined warming device comprising a power supply, electrical circuitry and other electrical components. Power can then be supplied to the dispenser 760. The heating element wire 592 is in electrical communication with components within the warming station which control the temperature of the heater. Once adjoined, the dual chamber pump dispenser 760 is positioned without the warming device while the PL container 530 is positioned within the heatable space of the warming device. Lubricant flowing from the PL container 530 into the dual chamber pump dispenser 760 is heated either by raising or maintaining its temperature. An insulating blanket 594 encloses the heating element wire 592 and surrounds one or more portions of the upper chamber 780, lower chamber 770, dual chamber outlet cavity 796 and dual chamber discharge cavity 797. A temperature probe 595 is positioned within the lower chamber 770 or operably connected to the lower chamber 770, and wired to the electrical circuitry connector 563. (A temperature probe 595 may be positioned within the upper chamber 780.) As a result, the temperature probe 595 communicates with an electrical component of the adjoined warming device sending a signal indicating the temperature of lubricant being heated within the lower chamber 770. The indicated temperature may be shown to the user on a display comprising the warming device. Should the indicated temperature exceed the designed temperature, the power would modulate or shut off. A temperature probe 564, previously described, is positioned within the hollow area of the piercing element 561 and wired to the electrical circuitry connector 563.

CONCLUSION, RAMIFICATIONS, AND SCOPE

The invention is intended to encourage the use of condoms and personal lubricant in sexual activities thereby reducing the spread of disease, including the human immunodeficiency virus (HIV), which may result in AIDS, and reducing the risk of pregnancy. Apart from its social purpose the invention also is intended enhance the sexual experience of adults, particularly post-menopausal women. The invention should achieve these purposes.

Although the description above contains much specificity, it should not be construed as limiting the scope of the invention but merely providing illustrations of some of the embodiments of this invention. For example, the design and shape of any container or compartment and the design, shape, type and location of their components, including the various seals, valves, pre-delivery chambers, discharge element, temperature sensing aid or raised annular ring, are not limited to the designs, shapes, types and locations shown in the drawings. For example, the depth of the condom compartment is depicted in the drawings as greater than that of the personal lubricant compartment. In fact, each compartment may be of equal depth or the personal lubricant compartment may be of greater depth than the condom compartment. The condom compartment may be of a shape other than cylindrical or rectangular. The top wall of the compartment may be in the shape of a half moon with a semi-cylindrical wall or other shape. A temperature sensing aid may comprise any type of temperature sensor including but not limited to a thermistor, temperature probe or thermocouple or any other type of component as an aid in determining the temperature of the liquid material enclosed in a compartment when the container is seated in a warming device comprising a temperature sensor.

The scope of the invention should be determined by the appended claims and legal equivalents, rather than by the examples given.

What is claimed is:

1. A personal lubricant dispenser comprising:
an enclosure;
a pre-delivery chamber disposed within the enclosure;
one or more heating elements disposed within the enclosure proximate to the pre-delivery chamber;
an electrical connector disposed on an exterior of the enclosure and electrically connected to the one or more heating elements;
an inlet cavity disposed within the enclosure above a portion of the pre-delivery chamber;
a piercing element attached to the inlet cavity and accessible from the exterior of the enclosure;
an inlet valve disposed within the enclosure and connecting the inlet cavity to the pre-delivery chamber, wherein the inlet valve is normally closed;
an inlet actuator disposed on the exterior of the enclosure and operably connected to the inlet valve to open the inlet valve;
an outlet cavity disposed within the enclosure below a portion of the pre-delivery chamber;
an outlet valve disposed within the enclosure and connecting the outlet cavity to the pre-delivery chamber, wherein the outlet valve is normally closed;
an outlet actuator disposed on the exterior of the enclosure and operably connected to the outlet valve to open the outlet valve; and
a spout disposed on or within the exterior of the enclosure and connected to the outlet cavity.

2. The dispenser as recited in claim 1, wherein the one or more heating elements are disposed within the pre-delivery chamber or integrated into one or more walls of the pre-delivery chamber or disposed outside the pre-delivery chamber.

3. The dispenser as recited in claim 1, further comprising a first temperature probe disposed within the piercing element.

4. The dispenser as recited in claim 3, further comprising an electrical circuit electrically connected to the electrical connector, the one or more heating elements and the first temperature probe to control a temperature of a personal lubricant within at least the pre-delivery chamber.

5. The dispenser as recited in claim 1, further comprising a second temperature probe proximate to the pre-delivery chamber.

6. The dispenser as recited in claim 5, wherein the second temperature probe is disposed within the pre-delivery chamber, or operably connected to the pre-delivery chamber.

7. The dispenser as recited in claim 5, further comprising an electrical circuit electrically connected to the electrical connector, the one or more heating elements and the second temperature probe to control a temperature of a personal lubricant within the at least pre-delivery chamber.

8. The dispenser as recited in claim 1, wherein the pre-delivery chamber comprises a heat conducting material.

9. The dispenser as recited in claim 1, further comprising an insulating blanket surrounding one or more portions of the pre-delivery chamber.

10. The dispenser as recited in claim 1, further comprising an upper pre-delivery chamber disposed above the pre-delivery chamber and connected between the inlet cavity and the inlet valve.

11. The dispenser as recited in claim 10, further comprising:
an upper chamber outlet cavity disposed within the enclosure and connected to the outlet cavity;
the upper pre-delivery chamber is further connected to the outlet valve; and
the outlet valve comprises a dual outlet valve that connects the outlet cavity to the pre-delivery chamber and connects the upper pre-delivery chamber to the upper chamber outlet cavity, wherein the dual outlet valve is normally closed.

12. The dispenser as recited in claim 10, further comprising an air duct connecting a top of the pre-delivery chamber to a top of the upper pre-delivery chamber.

13. The dispenser as recited in claim 10, wherein the one or more heating elements are disposed within the upper pre-delivery chamber or integrated into one or more walls of the upper pre-delivery chamber or disposed outside the upper pre-delivery chamber.

14. The dispenser as recited in claim 10, wherein the upper pre-delivery chamber comprises a heat conducting material.

15. The dispenser as recited in claim 10, further comprising an insulating blanket surrounding one or more portions of the upper pre-delivery chamber.

16. The dispenser as recited in claim 1, wherein the spout comprises an opening in the enclosure.

17. The dispenser as recited in claim 1, wherein a personal lubricant discharged from the spout is gravity fed.

18. The dispenser as recited in claim 1, wherein the dispenser is disposable.

19. The dispenser as recited in claim 1, wherein the outlet valve comprises a pump.

20. The dispenser as recited in claim 1, wherein the piercing element is shaped to receive a discharge element of a container such that the piercing element breaks a seal protecting a personal lubricant within the container and the personal lubricant flows through the piercing element into the inlet cavity.

21. The dispenser as recited in claim 20, wherein the container comprises a funnel-shaped enclosure.

22. The dispenser as recited in claim 21, further comprising:
a bead freely disposed within the funnel-shaped enclosure; and
an air release element disposed within a top portion of the funnel-shaped enclosure.

23. The dispenser as recited in claim 1, wherein the piercing element protrudes from the exterior of the enclosure.

24. The dispenser as recited in claim 1, wherein the piercing element is recessed within at least a portion of the inlet cavity and the inlet cavity is shaped to receive a discharge element of a container such that the piercing element breaks a seal protecting a personal lubricant within the container.

25. The dispenser as recited in claim 24, further comprising a gasket disposed within the inlet cavity that removeably secures the discharge element of the container.

26. The dispenser as recited in claim 25, wherein the gasket contacts an exterior of the discharge element or an interior of the discharge element.

27. The dispenser as recited in claim 24, wherein an interior of the inlet cavity is threaded and an exterior of the discharge element is threaded.

28. The dispenser as recited in claim 24, wherein an interior of the inlet cavity and the exterior of the discharge element are sized to form a friction fit.

29. The dispenser as recited in claim 1, further comprising:
a connection interface disposed on the enclosure that provides a removeable connection to a control device; and
wherein the piercing element and the electrical connector are disposed on or within the connection interface.

30. The dispenser as recited in claim 29, wherein the control device further comprises a personal lubricant container having a discharge element such that the piercing element is shaped to receive the discharge element and break a seal protecting a personal lubricant within the container and the personal lubricant flows through the piercing element into the inlet cavity.

31. The dispenser as recited in claim 30, wherein the personal lubricant container is removeable from the control device.

32. The dispenser as recited in claim 29, wherein the control device further comprises:
a power source; and
an electrical circuit electrically connected to the power source and the electrical connector to control a temperature of a personal lubricant within the pre-delivery chamber of the dispenser.

33. The dispenser as recited in claim 29, wherein the control device comprises a condom warming device, a personal lubricant warming device, or a combination condom and personal lubricant device.

34. A system comprising:
a dispenser comprising an enclosure, a connection interface disposed on the enclosure, a pre-delivery chamber disposed within the enclosure, one or more heating elements disposed within the enclosure proximate to the pre-delivery chamber, an electrical connector disposed on or within the connection interface and electrically connected to the one or more heating elements, an inlet cavity disposed within the enclosure above a portion of the pre-delivery chamber, a piercing element disposed on or within the connection interface and attached to the inlet cavity and accessible from the exterior of the enclosure, an inlet valve disposed within the enclosure that is normally closed and connects the inlet cavity to the pre-delivery chamber, an inlet actuator disposed on the exterior of the enclosure and operably connected to the inlet valve to open the inlet valve, an outlet cavity disposed within the enclosure below a portion of the pre-delivery chamber, an outlet valve disposed within the enclosure that is normally closed connects the outlet cavity to the pre-delivery chamber, wherein the outlet valve is normally closed, an outlet actuator disposed on the exterior of the enclosure and operably connected to the outlet valve to open the outlet valve, and a spout disposed on or within the exterior of the enclosure and connected to the outlet cavity; and
a control device removeably connected to the connection interface of the dispenser, the control device comprising a power source, an electrical circuit electrically connected to the power source and the electrical connector to control a temperature of a personal lubricant within at least the pre-delivery chamber of the dispenser, a personal lubricant container having a discharge element such that the piercing element of the dispenser is shaped to receive the discharge element and break a seal protecting the personal lubricant within the personal lubricant container and the personal lubricant flows through the piercing element into the inlet cavity of the dispenser.

35. The system as recited in claim 34, wherein the one or more heating elements are disposed within the pre-delivery chamber or integrated into one or more walls of the pre-delivery chamber or disposed outside the pre-delivery chamber.

36. The system as recited in claim 34, further comprising a first temperature probe disposed within the piercing element.

37. The system as recited in claim 34, further comprising a second temperature probe proximate to the pre-delivery chamber.

38. The system as recited in claim 37, wherein the second temperature probe is disposed within the pre-delivery chamber, or operably connected to the pre-delivery chamber.

39. The system as recited in claim 37, wherein the pre-delivery chamber comprises a heat conducting material.

40. The system as recited in claim 37, further comprising an insulating blanket surrounding one or more portions of the pre-delivery chamber.

41. The system as recited in claim 37, further comprising an upper pre-delivery chamber disposed above the pre-delivery chamber and connected between the inlet cavity and the inlet valve.

42. The system as recited in claim 41, further comprising:
an upper chamber outlet cavity disposed within the enclosure and connected to the outlet cavity;
the upper pre-delivery chamber is further connected to the outlet valve; and
the outlet valve comprises a dual outlet valve that connects the outlet cavity to the pre-delivery chamber and connects the upper pre-delivery chamber to the upper chamber outlet cavity, wherein the dual outlet valve is normally closed.

43. The system as recited in claim 41, further comprising an air duct connecting a top of the pre-delivery chamber to a top of the upper pre-delivery chamber.

44. The system as recited in claim 41, wherein the one or more heating elements are disposed within the upper pre-delivery chamber or integrated into one or more walls of the upper pre-delivery chamber or disposed outside the upper pre-delivery chamber.

45. The system as recited in claim 41, wherein the upper pre-delivery chamber comprises a heat conducting material.

46. The system as recited in claim 41, further comprising an insulating blanket surrounding one or more portions of the upper pre-delivery chamber.

47. The system as recited in claim 34, wherein the spout comprises an opening in the enclosure.

48. The system as recited in claim 34, wherein a personal lubricant discharged from the spout is gravity fed.

49. The system as recited in claim 34, wherein the dispenser is disposable.

50. The system as recited in claim 34, wherein the outlet valve comprises a pump.

51. The system as recited in claim 34, wherein the personal lubricant container comprises a funnel-shaped enclosure.

52. The system as recited in claim 51, further comprising:
a bead freely disposed within the funnel-shaped enclosure; and
an air release element disposed within a top portion of the funnel-shaped enclosure.

53. The dispenser as recited in claim 34, wherein the piercing element protrudes from the exterior of the enclosure.

54. The system as recited in claim 34, wherein the piercing element is recessed within at least a portion of the inlet cavity and the inlet cavity is shaped to receive the discharge element of the personal lubricant container.

55. The system as recited in claim 54, further comprising a gasket disposed within the inlet cavity that removeably secures the discharge element of the container.

56. The system as recited in claim 55, wherein the gasket contacts an exterior of the discharge element or an interior of the discharge element.

57. The dispenser as recited in claim 34, wherein an interior of the inlet cavity is threaded and an exterior of the discharge element is threaded.

58. The system as recited in claim 34, wherein an interior of the inlet cavity and the exterior of the discharge element are sized to form a friction fit.

59. The system as recited in claim 34, wherein the personal lubricant container is removeable from the control device.

60. The system as recited in claim 34, wherein the control device comprises a condom warming device, a personal lubricant warming device, or a combination condom and personal lubricant device.

* * * * *